(12) United States Patent
Ferrie et al.

(10) Patent No.: US 9,434,701 B2
(45) Date of Patent: Sep. 6, 2016

(54) AMINOQUINOXALINE DERIVATIVES FOR TREATMENT OF NEURODEGENERATIVE DISEASES

(75) Inventors: Laurent Ferrie, Palaiseau (FR); Bruno Figadere, Saint Cheron (FR); Gaël Le Douaron, Verriere le Buisson (FR); Rita Raisman-Vozari, Paris (FR); Fanny Schmidt, Chatenay Malabry (FR)

(73) Assignees: CENTRE NATIONAL DE LA RECHERCHE SCIENTIFIQUE (CNRS), Paris (FR); UNIVERSITE PARIS—SUD 11, Orsay (FR)

( * ) Notice: Subject to any disclaimer, the term of this patent is extended or adjusted under 35 U.S.C. 154(b) by 274 days.

(21) Appl. No.: 14/008,189

(22) PCT Filed: Mar. 30, 2012

(86) PCT No.: PCT/EP2012/055903
§ 371 (c)(1),
(2), (4) Date: Jan. 7, 2014

(87) PCT Pub. No.: WO2012/131080
PCT Pub. Date: Oct. 4, 2012

(65) Prior Publication Data
US 2014/0113903 A1    Apr. 24, 2014

(30) Foreign Application Priority Data

Mar. 30, 2011 (FR) ...................... 11 52645

(51) Int. Cl.
*A61K 31/498* (2006.01)
*C07D 241/42* (2006.01)

(52) U.S. Cl.
CPC ............ *C07D 241/42* (2013.01); *A61K 31/498* (2013.01)

(58) Field of Classification Search
CPC .................................................. A61K 31/498
See application file for complete search history.

(56) References Cited

U.S. PATENT DOCUMENTS

| 5,480,883 A | 1/1996 | Spada et al. |
| 2004/0102360 A1 | 5/2004 | Barnett et al. |
| 2011/0118270 A1 | 5/2011 | Schmidt |

FOREIGN PATENT DOCUMENTS

| EP | 1 479 384 A1 | 11/2004 |
| WO | WO-2004/030635 A2 | 4/2004 |
| WO | WO-2010/007179 A1 | 1/2010 |
| WO | WO-2010/151799 A2 | 12/2010 |
| WO | WO-2011/044229 A1 | 4/2011 |

OTHER PUBLICATIONS

Barton et al., "Biphenylenes-xxxi: Condensation of benzocyclobutene-1,2-dione with aliphatic and heterocyclic 1,2-diamines and the synthesis of cis-2-cyano-3-(2'-cyanovinyl)-1,4-diazabip henylene," Tetrahedron. vol. 35, 1979, pp. 241-247.
Elmes et al., "Quartenerarized pdppz; Synthesis, DNA-binding and biological studies of a nevel dppz derivative that causes cellular death upon light irradiation," Chem. Commun., vol. 47, No. 2, 2011, pp. 686-688.
International Search Report for International Application No. PCT/EP2012/055903 mailed May 31, 2012.
Kasai et al., "Synthesis of 2-Amino-3,8-Dimethylimidazo[4,5-f]Quinoxaline (Me-IQx), A Potent Mutagen Isolated from Fried Beef," Chemistry Letters © The Chemical Society of Japan, 1981, pp. 675-678.
Mourlevat et al., "Prevention of Dopaminergic Neuronal Death by Cyclic AMP in Mixed Neuronal/Glial Mesencephalic Cultures Requires the Repression of Presumptive Astrocytes," Molecular Pharmacology, vol. 64, 2003, pp. 578-586.
Nasielski et al., "A Liposoluble Cationic Complex of Ru(II) Based on 1,4,5,8-Tetra-Azaphenanthrene," Bull. Soc. Chim. Belg., vol. 97, No. 10, 1988, pp. 743-750.
Nasielski et al., Bull. Soc. Chim. Belg., "1,4,5,8-Tetraazaphenanthrene complexes of copper (I) and silver(I)," 1998, vol. 97, No. 11-12, pp. 983-992.
Nasielski-Hinkens et al., "Fragmentation of 1,4,5,8-Tetraazaphenanthrenes Upon Electron Impact: a New Example of Structural Integrity of Gas Phase Heteroaromatic Cations," Organic Mass Spectrometry, vol. 20, No. 12, 1985, pp. 733-737.
Poradowski Henryka Chemical Abstract, 1988, 1 page.
Schmidt et al., "Chemicals Possessing a Neurotrophin-Like Activity on Dopaminergic Neurons in Primary Culture," PLos ONE, 2009, vol. 4, No. 7, article e6215, pp. 1-9.
Wuts et al., "Greene's Protective Groups in Organic Synthesis," John Wiley & Sons, Inc., New York, 1981, pp. 494-653.
Zhang et al., "Quinozalinylurea derivatives as a novel class of JSP-1 inhibitors," Biorganic & Medicinal Chemistry Letters, vol. 17, 2007, pp. 2118-2122.

*Primary Examiner* — Sahar Javanmard
(74) *Attorney, Agent, or Firm* — Foley & Lardner LLP

(57) ABSTRACT

The present invention relates to compounds of formula (I) below: for which: —X represents a hydrogen atom, a halogen atom, a group $NO_2$ or $NH_2$, —$R_0$ represents H or —$CH_2$—C≡CH, and —$R_1$ and $R_2$ each represent, independently of one another, a hydrogen atom; a saturated or unsaturated, linear or branched hydrocarbon-based chain comprising from 1 to 10 carbon atoms; or an optionally substituted aryl group, and also the pharmaceutically acceptable salts thereof, the stereoisomers thereof or mixtures of stereoisomers thereof in any proportion, in particular for use thereof as a medicament, in particular in the treatment or prevention of neurodegenerative diseases, and also the processes for the preparation thereof and the pharmaceutical compositions comprising same.

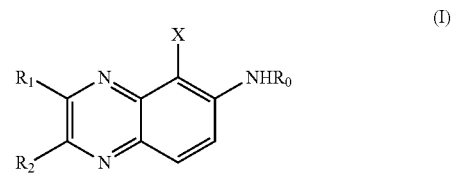

22 Claims, 8 Drawing Sheets

AMINOQUINOXALINE DERIVATIVES FOR TREATMENT OF NEURODEGENERATIVE DISEASES

The present invention relates to aminoquinoxaline derivatives, as well as their preparation methods, pharmaceutical compositions containing them and their use, especially for the treatment of neurodegenerative diseases.

With longer life expectancy, an increasing number of people suffer from neurodegenerative diseases such as Alzheimer's disease or Parkinson's disease.

A neurodegenerative disease is a disease that progressively affects the function of the nervous system, and in particular the brain; the disease can progress quickly or slowly (several weeks to several years), and often irreversibly. Thus, the function of nerve cells, especially neurons, is deteriorated, which can lead to cell death. Depending on the region of the nervous system affected by the disease, various functions may be affected, such as motor function, language, memory, perception or even cognition. The most common neurodegenerative diseases particularly include Alzheimer's disease and Parkinson's disease.

Alzheimer's disease, which affects around 24 million people worldwide, is a brain tissue disease that leads to progressive and irreversible loss of mental function. The first symptom is loss of the memory of recent events (amnesia), then the cognitive deficit extends to the regions of language (aphasia), organization of movement (apraxia), visual recognition (agnosia) and executive functions (such as decision making and planning).

Parkinson's disease affects the central nervous system and induces progressive motor function problems, especially body tremors.

Currently, the medications prescribed for these two diseases only delay the progression of the disease. There is nothing that can cure the disease or stop its progress, so there is a need for new, more active compounds for the treatment of these neurodegenerative diseases.

The inventors of the present invention have already demonstrated the potential of chimeric compounds with a quinoxaline nucleus substituted by an aliphatic hydrophobic chain in the treatment of neurodegenerative diseases (WO 2010/007179).

However, the inventors have surprisingly discovered that quinoxaline derivatives retained their activity and were still able to pass the blood-brain barrier in the absence of substitution with a hydrophobic chain, which had seemed to be essential to passing the blood-brain barrier.

Accordingly, the subject of the present invention is a compound of the following formula (I):

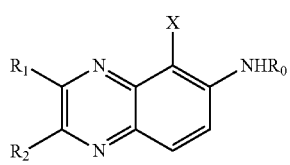

(I)

in which:
X represents a hydrogen atom, a halogen atom such as bromine or chlorine, or an $NO_2$ or $NH_2$ group,
$R_0$ represents H or —$CH_2$—C≡H, especially H, and
$R_1$ and $R_2$ each represent, independently of one another, a hydrogen atom, a saturated or unsaturated, linear or branched hydrocarbon chain comprising 1 to 10, preferably 1 to 6, carbon atoms; or an optionally substituted aryl group, as well as the pharmaceutically acceptable salts thereof, stereoisomers or mixtures of stereoisomers thereof, in any proportions, particularly a mixture of enantiomers, and especially a racemic mixture, for its use as a medicament, especially as a neutrophic or neuroprotective medicament.

In the present invention "halogen" means a bromine, chlorine, iodine or fluorine atom, and especially a bromine atom.

In the present invention, "$(C_1$-$C_6)$alkyl" means any saturated linear or branched hydrocarbon group with 1 to 6 carbon atoms, in particular methyl, ethyl, n-propyl, isopropyl n-butyl, isobutyl, sec-butyl, tert-butyl, n-pentyl and n-hexyl groups.

In the present invention, "$(C_1$-$C_6)$alkoxy" group means a $(C_1$-$C_6)$alkyl group such as defined above linked to the rest of the molecule by means of an oxygen atom and in particular, methoxy, ethoxy, n-propoxy, isopropoxy, n-butoxy, isobutoxy, sec-butoxy, tert-butoxy, n-pentoxy and n-hexoxy groups.

In the present invention, "aryl" group means an aromatic hydrocarbon group, preferably containing 6 to 10 carbon atoms and comprising one or more fused rings, such as, for example, a phenyl or naphthyl group. Advantageously, it is a phenyl group.

When the aryl group is substituted, it can advantageously be substituted with one or more groups chosen from among a halogen atom, a $(C_1$-$C_6)$alkyl, $(C_1$-$C_6)$alkoxy, aryl, $N_3$, $NO_2$, $NH_2$, or —NH—$((C_1$-$C_6)$alkyl) group; preferably chosen from among a halogen atom, a $(C_1$-$C_6)$alkyl, $(C_1$-$C_6)$ alkoxy or aryl group.

In the present invention, "unsaturated" means that the hydrocarbon chain can have one or more unsaturations.

In the present invention, "unsaturation" means a double or triple bond.

In the present invention, "pharmaceutically acceptable" means what is used in the preparation of a pharmaceutical compound, which is generally safe, nontoxic and not biologically or otherwise undesirable and which is acceptable for both veterinary and human pharmaceutical use.

In the present invention, "N-protective group" means any substituent that protects the $NH_2$ group against undesirable reactions, such as the N-protective groups described in Greene, "Protective Groups in Organic Synthesis", (John Wiley & Sons, New York (1981)) and Harrison et al. "Compendium of Synthetic Organic Methods", Vols. 1 to 8 (J. Wiley & Sons, 1971 to 1996). N-protective groups comprise, including the protected amine function, carbamates, amides, N-alkyl derivatives, amino acetal derivatives, N-benzyl derivatives, imine derivatives, enamine derivatives, mono- or dialkylamino propargylamine derivatives and N-heteroatom derivatives. In particular, the N-protective group includes formyl, acetyl, benzoyl, pivaloyl, phenylsulfonyl, benzyl (Bn), t-butyloxycarbonyl (Boc), benzyloxycarbonyl (Cbz), p-methoxybenzyloxycarbonyl, p-nitrobenzyl-oxycarbonyl, trichloroethoxycarbonyl (TROC), allyloxycarbonyl (Alloc), 9-fluorenylmethoxycarbonyl (Fmoc), trifluoro-acetyl, dimethylaminopropargyl, benzyl carbamates (optionally substituted), and the like.

In the present invention, "pharmaceutically-acceptable salts" of a compound mean salts that are pharmaceutically acceptable, such as defined here, that have the desired pharmacological activity of the parent compound. Such salts include:

(1) Hydrates and solvates,
(2) Acid addition salts formed with inorganic acids such as hydrochloric acid, hydrobromic acid, sulfuric acid, nitric acid, phosphoric acid and the like, or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethane sulfonic acid, lactic acid, maleic acid, malic acid, mandelic acid, methanesulfonic acid, muconic acid, 2-naphthalene sulfonic acid, propionic acid, salicylic acid, succinic acid, dibenzoyl-L-tartaric acid, tartaric acid, p-toluenesulfonic acid, trimethylacetic acid, trifluoroacetic acid and the like; and
(3) The salts formed when an acid proton present in the parent compound is replaced by a metal ion, for example an alkaline metal ion ($Na^+$, $K^+$ or $Li^+$ for example), or an alkaline-earth metal ion (such as $Ca^{2+}$ or $Mg^{2+}$) or an aluminum ion; or is coordinated with an organic or inorganic base. Acceptable organic bases include diethanolamine, ethanolamine, N-methylglucamine, triethanolamine, tromethamine and the like Acceptable inorganic bases include aluminum hydroxide, calcium hydroxide, potassium hydroxide, sodium carbonate and sodium hydroxide.

In this invention, "stereoisomer" means a geometric isomer or an optical isomer.

Geometric isomers result from the different position of substituents on a double bond that can have a Z or E configuration.

Optical isomers result from the different position in space of substituents on a carbon atom with 4 different substituents. This carbon is therefore a chiral or asymmetric center. Optical isomers include diastereoisomers and enantiomers. Optical isomers that are mirror images of one another but cannot be superimposed are called "enantiomers". Optical isomers that are not mirror images are called "diastereomers".

A mixture containing equal quantities of two individual enantiomer forms of opposite chirality is called a "racemic mixture".

According to one particular embodiment, the compound according to the invention will not be a compound of formula (I) for which X and $R_0$ each represent a hydrogen atom and $R_1$ and $R_2$ each represent, independently of one another, a hydrogen atom or an optionally substituted aryl group or one of its pharmaceutically acceptable salts.

Preferably, the compound of formula (I) according to the invention will not be 6-amino-5-bromoquinoxaline, a compound described as a modulator of alpha adrenergic receptors in WO 2011/044229.

Advantageously, X will represent a hydrogen atom, a bromine atom or an $NH_2$ or $NO_2$ group. More particularly, X can represent a hydrogen atom.

According to another embodiment, X will represent a halogen atom or an $NH_2$ or $NO_2$ group; notably a bromine atom or an $NH_2$ or $NO_2$ group.

The term "saturated or unsaturated, linear or branched hydrocarbon chain comprising 1 to 10, preferably 1 to 6, carbon atoms" will more particularly represent a saturated linear or branched hydrocarbon chain, comprising 1 to 10, preferably 1 to 6, carbon atoms in the definition of the $R_1$ and $R_2$ groups, and more particularly a $(C_1-C_6)$alkyl group such as defined above.

Advantageously, $R_1$ and $R_2$ each represent, independently of one another, a hydrogen atom, a $(C_1-C_6)$alkyl group; or an optionally substituted aryl group, especially optionally substituted by one or more groups chosen from among a halogen group, a $(C_1-C_6)$alkyl, $(C_1-C_6)$alkoxy, aryl, $N_3$, $NO_2$, $NH_2$, or $-NH-((C_1-C_6)$alkyl) group, preferably chosen from among a halogen atom, a $(C_1-C_6)$alkyl, $(C_1-C_6)$alkoxy or aryl group.

In particular, $R_1$ and $R_2$ can each represent, independently of one another, a hydrogen atom, a $(C_1-C_6)$alkyl group or an optionally substituted phenyl group, especially optionally substituted by one or more groups chosen from among a halogen atom, a $(C_1-C_6)$alkyl, $(C_1-C_6)$alkoxy, aryl, $N_3$, $NO_2$, $NH_2$, or $-NH-((C_1-C_6)$alkyl) group, preferably chosen from among a halogen atom, a $(C_1-C_6)$alkyl, $(C_1-C_6)$alkoxy or aryl group.

According to one particular embodiment, $R_1$ will represent an aryl group, especially phenyl, optionally substituted, especially by one or more groups chosen from among a halogen atom, a $(C_1-C_6)$alkyl, $(C_1-C_6)$alkoxy, aryl, $N_3$, $NO_2$, $NH_2$, or $-NH-((C_1-C_6)$alkyl) group, preferably chosen from among a halogen atom, a $(C_1-C_6)$alkyl, $(C_1-C_6)$alkoxy or aryl group.

According to another particular embodiment of the invention, $R_2$ will represent a saturated or unsaturated, linear or branched hydrocarbon chain comprising 1 to 10, preferably 1 to 6, carbon atoms; preferably a $(C_1-C_6)$alkyl group.

According to another particular embodiment of the invention:
$R_1$ will represent a saturated or unsaturated, linear or branched hydrocarbon chain comprising 1 to 10, preferably 1 to 6, carbon atoms such as a $(C_1-C_6)$alkyl group, or an optionally substituted aryl group, especially optionally substituted by one or more groups chosen from among a halogen atom, a $(C_1-C_6)$alkyl, $(C_1-C_6)$alkoxy, aryl, $N_2$, $NO_2$, $NH_2$, or $-NH-((C_1-C_6)$alkyl) group, and
$R_2$ will represent a saturated or unsaturated, linear or branched hydrocarbon chain comprising 1 to 10, preferably 1 to 6, carbon atoms; such as a $(C_1-C_6)$alkyl group.

In particular, the $R_1$ and $R_2$ radicals may be defined as follows:
$R_1$ will represent a $(C_1-C_6)$alkyl group or an optionally substituted aryl group, especially optionally substituted by one or more groups chosen from among a halogen atom, a $(C_1-C_6)$alkyl, $(C_1-C_6)$alkoxy, aryl, $N_3$, $NO_2$, $NH_2$, or $-NH-((C_1-C_6)$alkyl) group, advantageously an optionally substituted aryl group, notably optionally substituted by one or more groups chosen from among a halogen atom, a $(C_1-C_6)$alkyl, $(C_1-C_6)$alkoxy, aryl, $N_3$, $NO_2$, $NH_2$, or $-NH-((C_1-C_6)$alkyl) group, and
$R_2$ will represent a $(C_1-C_6)$alkyl group.

In the definitions of $R_1$ and $R_2$ above, the $(C_1-C_6)$alkyl group may be more particularly a methyl, n-butyl, n-hexyl, s-butyl or t-butyl group, and the optionally substituted aryl group may be more particularly a phenyl, p-methoxyphenyl, m-methoxyphenyl, 3,4-dimethoxyphenyl, 3,4,5-trimethoxyphenyl, 2-naphthyl, p-fluorophenyl, p-methylphenyl, p-chlorophenyl, 3,4-dichlorophenyl, or biphenyl group.

Compounds of formula (I) may notably be chosen from among the following compounds:

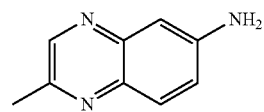

4ba

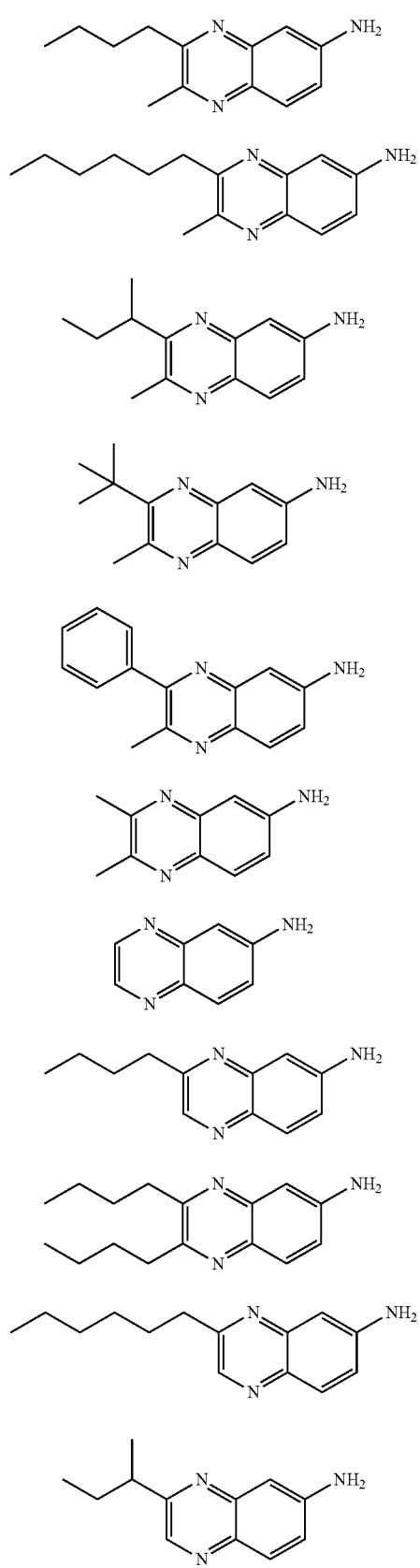
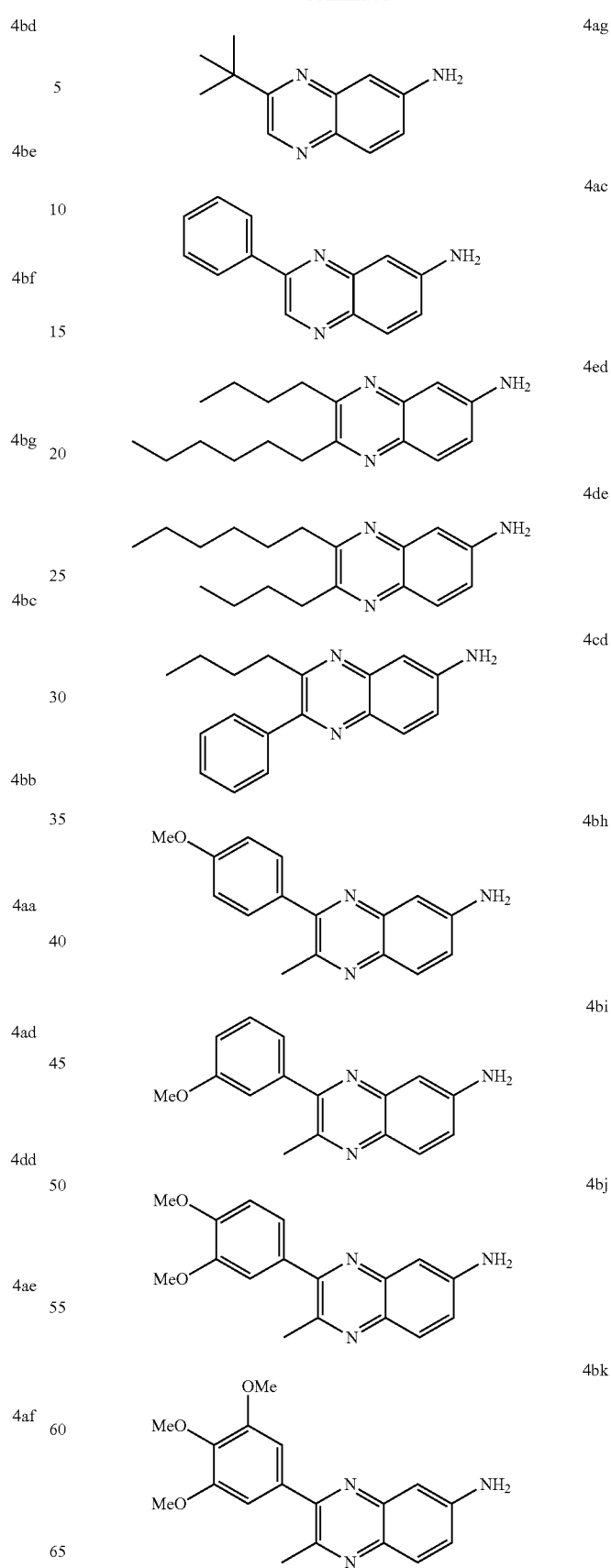

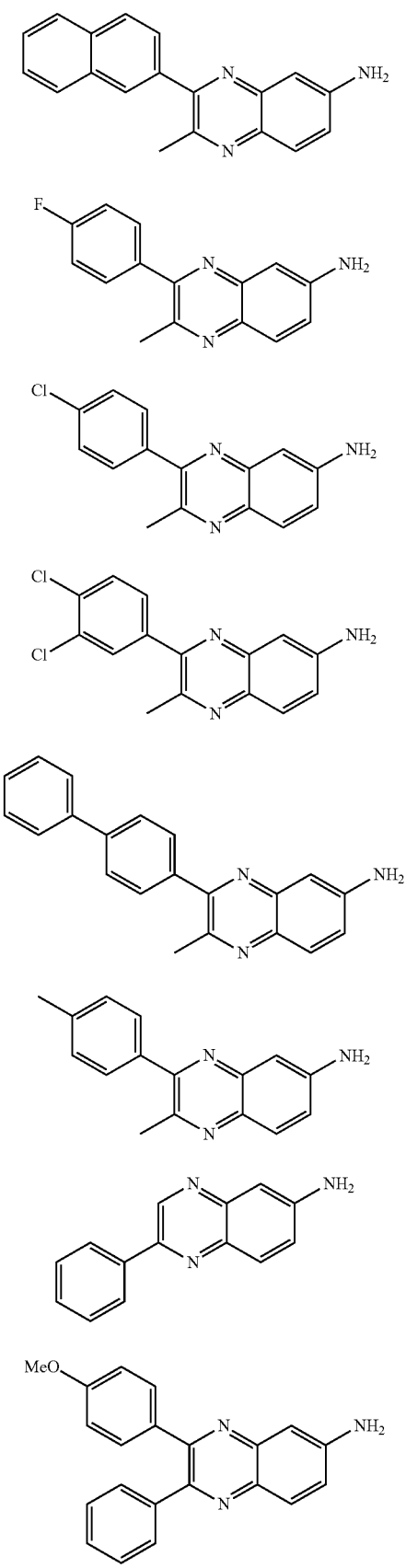
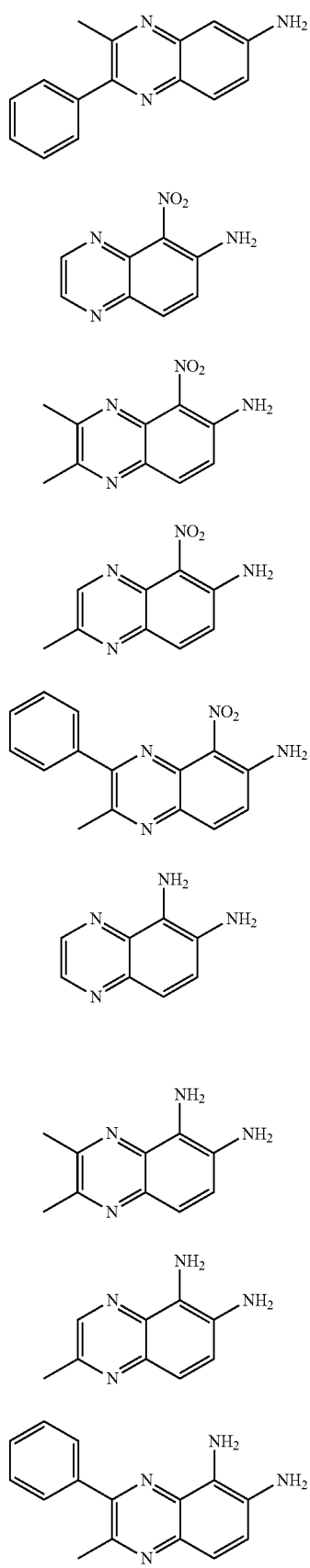

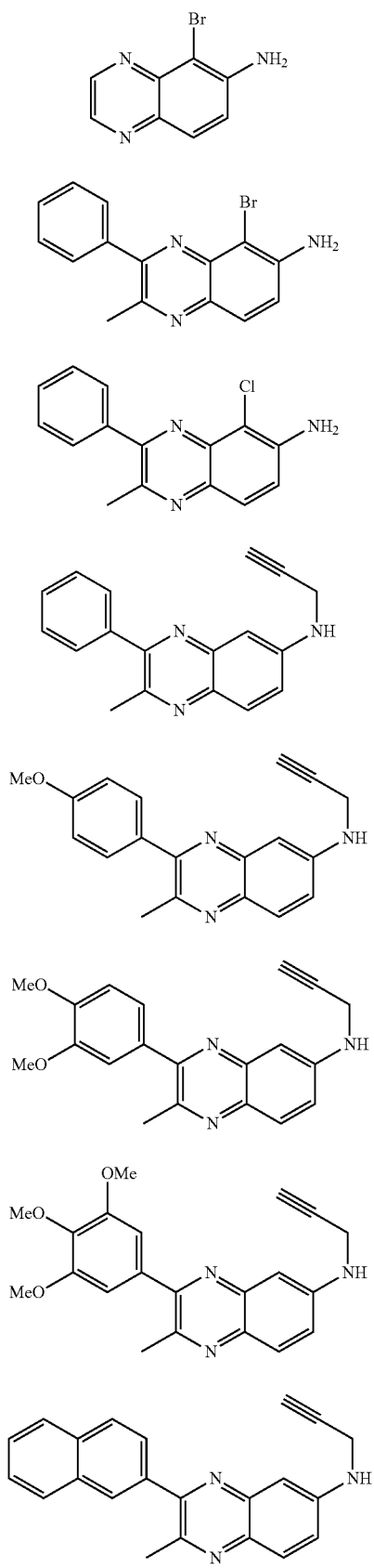
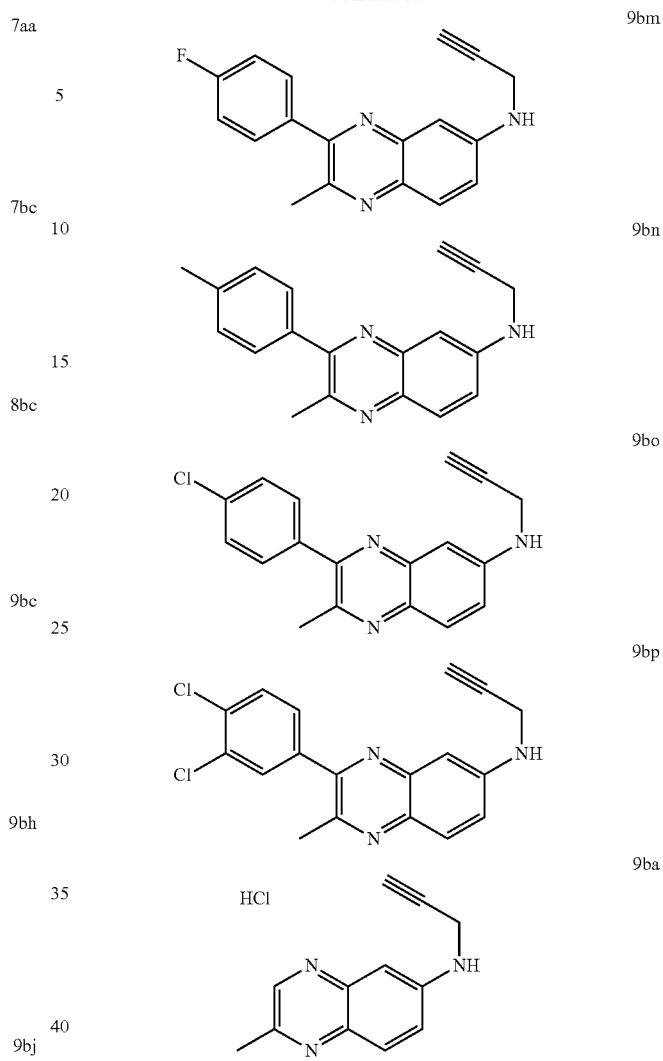

The present invention also concerns the use of a compound of formula (I) such as defined above for the production of a medicament, especially a neutrophic or neuroprotective medicament.

The present invention also has for a subject a compound of formula (I) such as defined above for use in the treatment or prevention of neurodegenerative diseases such as Alzheimer's disease, Parkinson's disease, multiple sclerosis or amyotrophic lateral sclerosis (ALS), also called Lou Gehrig's disease, and in particular Parkinson's disease.

The present invention also concerns the use of a compound of formula (I) such as defined above for the production of a medicament intended for the treatment or prevention of neurodegenerative diseases such as Alzheimer's disease, Parkinson's disease, multiple sclerosis or amyotrophic lateral sclerosis (ALS), also called Lou Gehrig's disease, in particular Parkinson's disease.

The present invention also concerns a method for the treatment or prevention of neurodegenerative diseases such as Alzheimer's disease, Parkinson's disease, multiple sclerosis or amyotrophic lateral sclerosis (ALS), also called Lou Gehrig's disease, in particular Parkinson's disease, comprising the administration of an effective quantity of a compound of formula (I) such as defined above to a patient in need thereof.

The invention also has for a subject a pharmaceutical composition containing at least one compound of formula (I) such as defined above and a pharmaceutically-acceptable carrier.

Pharmaceutical compositions according to the invention may be formulated for parenteral (for example subcutaneous, intraperitoneal, intramuscular, intravenous, intracranial, intrathecal, etc.), oral, sublingual, transdermal, local or rectal administration, intended for mammals, including humans. The dosage varies according to the treatment and according to the condition in question.

In the pharmaceutical compositions of the present invention, the active ingredient can be administered in the form of administration units, mixed with conventional pharmaceutical carriers, to animals or human beings.

Appropriate oral administration unit forms include tablets, gels, powders, granules, and oral solutions or suspensions, and parenteral administration forms, notably intraperitoneal.

When a solid composition is prepared in the form of tablets, the main active ingredient is mixed with a pharmaceutical carrier such as gelatin, starch, lactose, magnesium stearate, talc, gum arabic, or the like. The tablets can be coated with sucrose or other appropriate materials or even be treated so that they have an extended or delayed activity and that they continuously release a predetermined quantity of active ingredient.

A capsule preparation is obtained by mixing the active ingredient with a diluent and pouring the mixture obtained into hard or soft capsules.

A preparation in the form of a syrup or elixir can contain the active ingredient conjointly with a sweetener, an antiseptic and an appropriate taste enhancer and dye.

Powders or granules dispersible in water can contain the active ingredient in mixture with dispersing or wetting agents or suspending agents, and with flavor correctors or sweeteners.

For parenteral administration, aqueous suspensions, isotonic saline solutions or sterile and injectable solutions are used that contain pharmacologically-compatible dispersing agents and/or wetting agents.

The active ingredient can also be formulated in the form of microcapsules, possibly with one or more additional carriers.

The compounds of the invention can be used in doses comprised between 0.01 mg and 1000 mg per day, given in a single dose once daily or administered in several doses throughout the day, for example twice daily in equal doses. The dose administered per day is advantageously comprised between 5 mg and 500 mg, and still more advantageously between 10 mg and 200 mg. It may be necessary to use doses exceeding these ranges, which those skilled in the art will be able to realize themselves.

According to one particular embodiment, the pharmaceutical composition as defined above may further comprise another active ingredient, particularly useful in the treatment or prevention of neurodegenerative diseases, advantageously selected from acetylcholinesterase inhibitors such as donepezil, galanthamine, rivastigmine, memantine and tacrine; monoamine oxidase inhibitors such as selegiline and rasagiline, catecholamine O-methyltransferase inhibitors such as entacapone; glutamatergic inhibitors such as amantadine and baclofen; cholinergic agonists such as sabcomeline; dopamine agonists such as pergolide, cabergoline, ropinirole and pramipexole; neurotransmitter analogs or precursors such as L-3,4-dihydroxyphenylalanine; and anticholinergics such as trihexyphenidyl and tropatepine.

The subject of the invention is also a compound of the following formula (I):

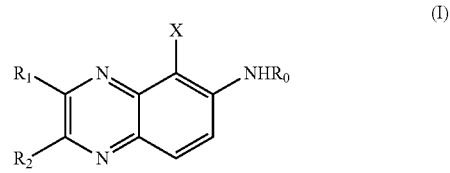

in which:
X represents a hydrogen atom, a halogen atom such as bromine or chlorine, or an $NO_2$ or $NH_2$ group,
$R_0$ represents H or —$CH_2$—C≡H, especially H, and
$R_1$ and $R_2$ each represent, independently of one another, a hydrogen atom, a saturated or unsaturated, linear or branched hydrocarbon chain comprising 1 to 10, preferably 1 to 6, carbon atoms; or an optionally substituted aryl group, as well as the pharmaceutically acceptable salts thereof, stereoisomers or mixtures of stereoisomers thereof, in any proportions, particularly a mixture of enantiomers, and especially a racemic mixture, excluding compounds for which X and $R_0$ each represent a hydrogen atom, and $R_1$ and $R_2$ each represent, independently of one another, a hydrogen atom, a saturated or unsaturated linear or branched hydrocarbon chain containing 1 to 6 carbon atoms, or an unsubstituted aryl group and pharmaceutically acceptable salts thereof.

The excluded compounds are compounds described in WO 2010/007179 as synthesis intermediates.

According to one particular embodiment, the compound according to the invention will not be a compound of formula (I) for which X and $R_0$ each represent a hydrogen atom and $R_1$ and $R_2$ each represent, independently of one another, a hydrogen atom or an optionally substituted aryl group or one of its pharmaceutically acceptable salts.

Preferably, the compound of formula (I) according to the invention will not be 6-amino-5-bromoquinoxaline, 5-nitro-6-amino-quinoxaline, 3-methyl-5-nitro-6-amino-quinoxaline, 2-methyl-5-nitro-6-amino-quinoxaline, 5,6-diamino quinoxaline, 5,6-diamino-2-methyl-quinoxaline, 5,6-diamino-2-decyl-quinoxaline and 5,6-diamino-3-decyl-quinoxaline. Such compounds are notably described in WO 2011/044229; Nasielski-Hinkens and Kaisin Organic Mass Spectrometry 1985, 20(12), 733-737; and Nasielski et al. Bull. Soc. Chim. Belg. 1988, 97(10), 743-750.

According to a first particular embodiment, X and $R_0$ each represent a hydrogen atom and at least one of the $R_1$ and $R_2$ groups represent a substituted aryl group, especially by one or more groups chosen from among a halogen group, a $(C_1-C_6)$alkyl, $(C_1-C_6)$alkoxy, aryl, $N_3$, $NO_2$, $NH_2$, or —NH—$((C_1-C_6)$alkyl) group, preferably chosen from among a halogen atom, a $(C_1-C_6)$alkyl, $(C_1-C_6)$alkoxy or aryl group.

This substituted aryl group can be a p-methoxyphenyl, m-methoxyphenyl, 3,4-dimethoxyphenyl, 3,4,5-trimethoxyphenyl, p-fluorophenyl, p-methylphenyl, p-chlorophenyl, 3,4-dichlorophenyl, or biphenyl group.

The other $R_1$ or $R_2$ group can then represent a hydrogen atom; a $(C_1-C_6)$alkyl group; or an optionally substituted aryl group, such as phenyl, especially optionally substituted by one or more groups chosen from among a halogen group, a $(C_1-C_6)$alkyl, $(C_1-C_6)$alkoxy, aryl, $N_3$, $NO_2$, $NH_2$, or —NH—(($C_1$-$C_6$)alkyl) group, preferably chosen from among a halogen atom, a ($C_1$-$C_6$)alkyl, ($C_1$-$C_6$)alkoxy or aryl group.

Advantageously, X and $R_0$ each represent a hydrogen atom, one of the $R_1$ and $R_2$ groups represent a substituted aryl group, such as phenyl, especially substituted by one or more groups chosen from among a halogen atom, a ($C_1$-$C_6$) alkyl, ($C_1$-$C_6$)alkoxy, aryl, $N_3$, $NO_2$, $NH_2$, or —NH—(($C_1$-$C_6$)alkyl) group, and the other $R_1$ or $R_2$ group represents a saturated or unsaturated, linear or branched hydrocarbon chain containing 1 to 10, preferably 1 to 6, carbon atoms, such as a ($C_1$-$C_6$)alkyl group.

Within the scope of this first particular embodiment, the ($C_1$-$C_6$)alkyl group may more particularly be a methyl, n-butyl, n-hexyl, s-butyl or t-butyl group, and the optionally substituted aryl group may more particularly be a phenyl, p-methoxyphenyl, m-methoxyphenyl, 3,4-dimethoxyphenyl, 3,4,5-trimethoxyphenyl, 2-naphthyl, p-fluorophenyl, p-methylphenyl, p-chlorophenyl, 3,4-dichlorophenyl, or biphenyl group.

Advantageously, $R_1$ will represent an aryl group, especially phenyl, optionally substituted, especially by one or more groups chosen from among a halogen atom, a ($C_1$-$C_6$) alkyl, ($C_1$-$C_6$)alkoxy, aryl, $N_3$, $NO_2$, $NH_2$, or —NH—(($C_1$-$C_6$)alkyl) group, preferably chosen from among a halogen atom, a ($C_1$-$C_6$)alkyl, ($C_1$-$C_6$)alkoxy or aryl group. This group can be particularly chosen from among phenyl, p-methoxyphenyl, m-methoxyphenyl, 3,4-dimethoxyphenyl, 3,4,5-trimethoxyphenyl, 2-naphthyl, p-fluorophenyl, p-methylphenyl, p-chlorophenyl, 3,4-dichlorophenyl, and biphenyl groups.

According to another embodiment, X represents a halogen atom or an $NO_2$ or $NH_2$ group and notably represents a bromine atom or an $NO_2$ or $NH_2$ group and/or $R_0$ represents —$CH_2$—C≡H.

$R_1$ and $R_2$ will then advantageously each represent, independently of one another, a hydrogen atom; a ($C_1$-$C_6$)alkyl group; or an optionally substituted aryl group, especially optionally substituted by one or more groups chosen from among a halogen atom, a ($C_1$-$C_6$)alkyl, ($C_1$-$C_6$)alkoxy, aryl, $N_3$, $NO_2$, $NH_2$, or —NH—(($C_1$-$C_6$)alkyl) group, preferably chosen from among a halogen atom, a ($C_1$-$C_6$)alkyl, ($C_1$-$C_6$)alkoxy or aryl group.

In particular, $R_1$ and $R_2$ can each represent, independently of one another, a hydrogen atom; a ($C_1$-$C_6$)alkyl group; or an optionally substituted phenyl group, especially optionally substituted by one or more groups chosen from among a halogen atom, a ($C_1$-$C_6$)alkyl, ($C_1$-$C_6$)alkoxy, aryl, $N_3$, $NO_2$, $NH_2$, or —NH—(($C_1$-$C_6$)alkyl) group, preferably chosen from among a halogen atom, a ($C_1$-$C_6$)alkyl, ($C_1$-$C_6$)alkoxy or aryl group.

According to one particular embodiment, $R_1$ will represent an aryl group, especially phenyl, optionally substituted, especially by one or more groups chosen from among a halogen atom, a ($C_1$-$C_6$)alkyl, ($C_1$-$C_6$)alkoxy, aryl, $N_3$, $NO_2$, $NH_2$, or —NH—(($C_1$-$C_6$)alkyl) group, preferably chosen from among a halogen atom, a ($C_1$-$C_6$)alkyl, ($C_1$-$C_6$)alkoxy or aryl group.

According to another particular embodiment, $R_2$ will represent a saturated or unsaturated, linear or branched hydrocarbon chain comprising 1 to 10, preferably 1 to 6, carbon atoms; preferably a ($C_1$-$C_6$)alkyl group According to another particular embodiment:

$R_1$ will represent a saturated or unsaturated, linear or branched hydrocarbon chain comprising 1 to 10, preferably 1 to 6, carbon atoms such as a ($C_1$-$C_6$)alkyl group; or an optionally substituted aryl group, especially optionally substituted by one or more groups chosen from among a halogen atom, a ($C_1$-$C_6$)alkyl, ($C_1$-$C_6$)alkoxy, aryl, $N_3$, $NO_2$, $NH_2$, or —NH—(($C_1$-$C_6$)alkyl) group, and $R_2$ will represent a saturated or unsaturated, linear or branched hydrocarbon chain comprising 1 to 10, preferably 1 to 6, carbon atoms; such as a ($C_1$-$C_6$)alkyl group In particular, the $R_1$ and $R_2$ radicals may be defined as follows:

$R_1$ will represent a ($C_1$-$C_6$)alkyl group or an optionally substituted aryl group, especially optionally substituted by one or more groups chosen from among a halogen atom, a ($C_1$-$C_6$)alkyl, ($C_1$-$C_6$)alkoxy, aryl, $N_3$, $NO_2$, $NH_2$, or —NH—(($C_1$-$C_6$)alkyl) group, advantageously an optionally substituted aryl group, notably optionally substituted by one or more groups chosen from among a halogen atom, a ($C_1$-$C_6$)alkyl, ($C_1$-$C_6$)alkoxy, aryl, $N_3$, $NO_2$, $NH_2$, or —NH—(($C_1$-$C_6$)alkyl) group, and $R_2$ will represent a ($C_1$-$C_6$)alkyl group.

In the definitions of $R_1$ and $R_2$ above, the ($C_1$-$C_6$)alkyl group may be more particularly a methyl, n-butyl, n-hexyl, s-butyl or t-butyl group, and the optionally substituted aryl group may be more particularly a phenyl, p-methoxyphenyl, m-methoxyphenyl, 3,4-dimethoxyphenyl, 3,4,5-trimethoxyphenyl, 2-naphthyl, p-fluorophenyl, p-methylphenyl, p-chlorophenyl, 3,4,-dichlorophenyl, or biphenyl group.

Compounds of formula (I) may notably be chosen from among the following compounds:

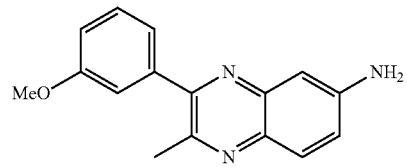

4bi

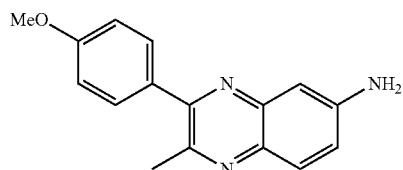

4bh

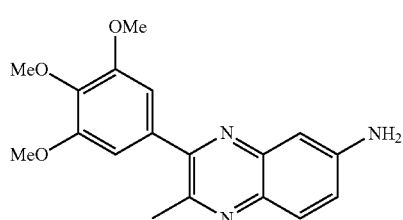

4bk

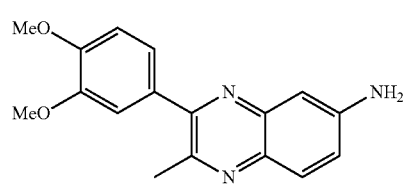

4bj

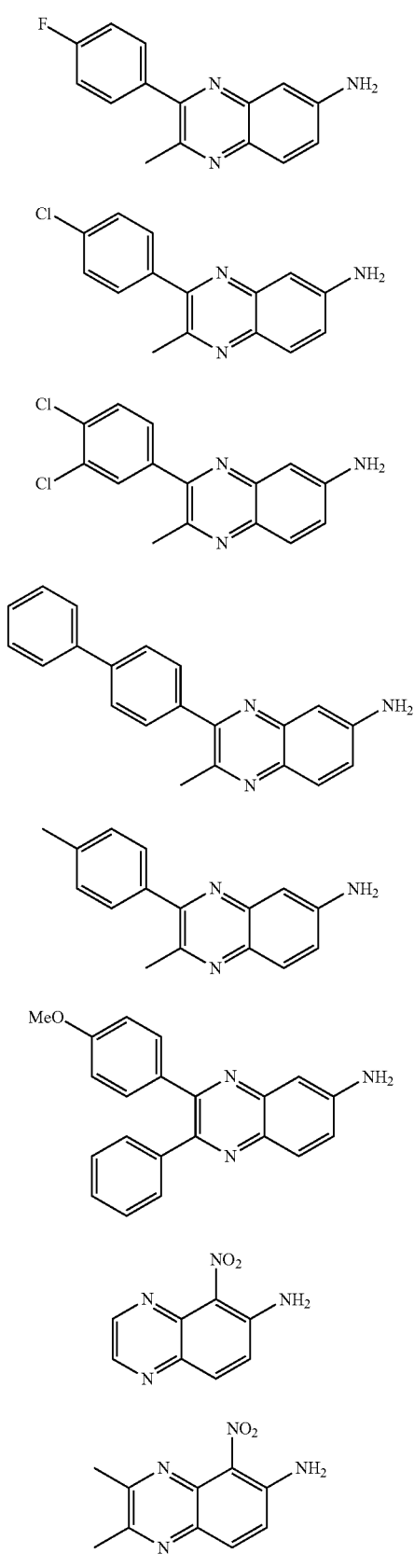
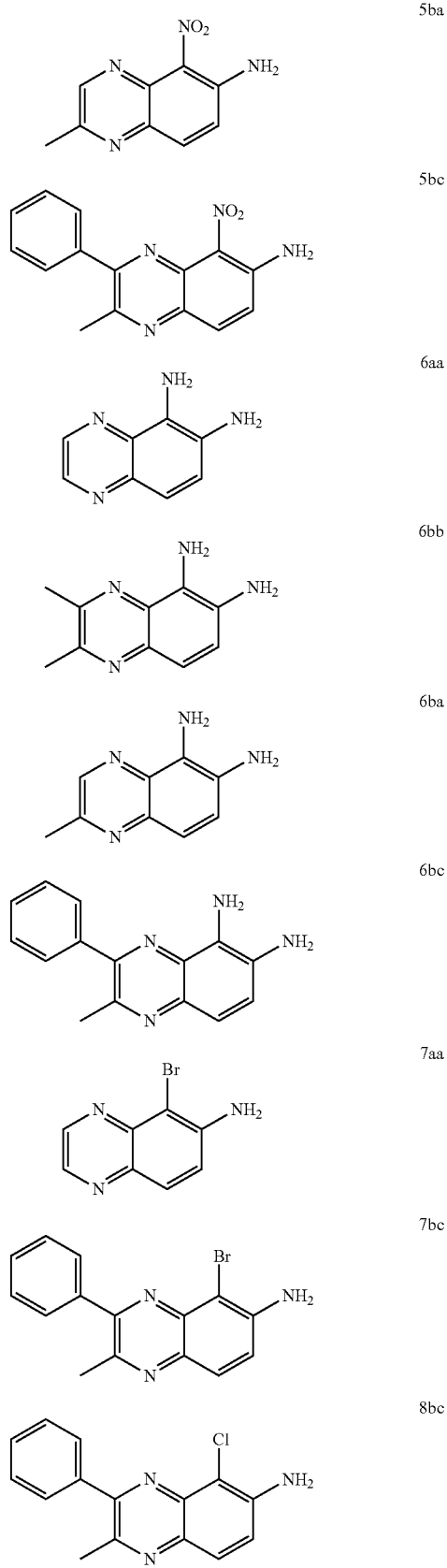

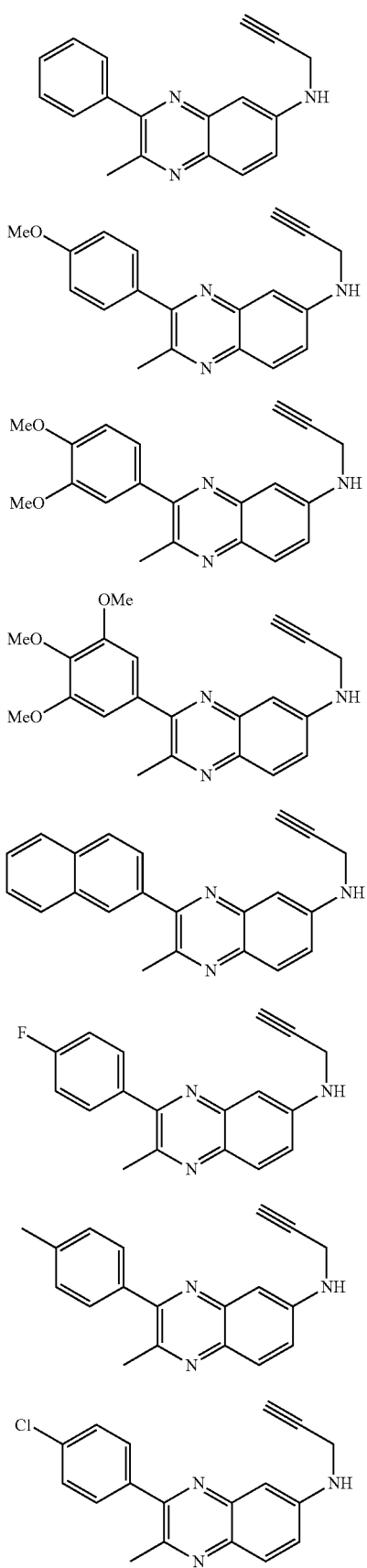

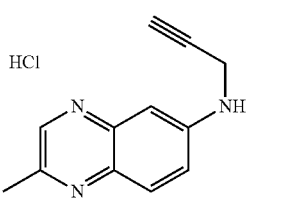

The present invention also has for a subject a method (1) for preparing a compound of formula (I) above for which X=R₀=H and at least one of the $R_1$ and $R_2$ groups represents a substituted aryl group, comprising the following successive steps:

(a1) coupling between 4-nitrophenylene-1,2-diamine and a compound of formula (II) below:

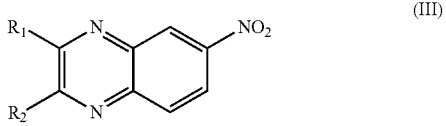

for which $R_1$ and $R_2$ are as defined previously, at least one of the $R_1$ and $R_2$ groups representing a substituted aryl group, to give a compound of formula (III) below:

$$\underset{R_2}{\overset{R_1}{\diagdown}}\!\!\begin{array}{c}N\\N\end{array}\!\!\diagup\!\!NO_2 \quad (III)$$

for which $R_1$ and $R_2$ are as defined previously, at least one of the $R_1$ and $R_2$ groups representing a substituted aryl group, and (b1) reduction of the nitro function of compound (III) obtained in previous step (a1) to give a compound of formula (I) for which X=R₀=H and at least one of the $R_1$ and $R_2$ groups represents a substituted aryl group.

Preferably, X represents a hydrogen atom, one of the $R_1$ and $R_2$ groups represents a substituted aryl group, such as phenyl, especially substituted by one or more groups chosen from among a halogen atom, a $(C_1-C_6)$alkyl, $(C_1-C_6)$alkoxy, aryl, $N_3$, $NO_2$, $NH_2$, or —NH—$((C_1-C_6)$alkyl) group, and the other $R_1$ or $R_2$ group represents a saturated or unsaturated, linear or branched hydrocarbon chain comprising 1 to 10, preferably 1 to 6, carbon atoms, such as a $(C_1-C_6)$alkyl group.

Step (a1):

The starting materials used for this step is generally commercially available or may be easily prepared by methods well known to the skilled person.

This reaction will advantageously be conducted in water as solvent, particularly under reflux.

Step (b1):

The reducing agent used in step (b1) to reduce the nitro function into an amino function will advantageously be $SnCl_2$. This reaction may be performed in ethanol, preferably absolute ethanol, and advantageously under reflux thereof.

This reduction step may also be conducted under hydrogen atmosphere, in the presence of palladium on carbon.

The compound thus obtained can be separated from the reaction medium by methods well-known to the person skilled in the art, such as, for example, by extraction, evaporation of the solvent or even by precipitation and filtration.

The compound can also be purified, if necessary, by techniques well known to the person skilled in the art, such as recrystallization if the compound is crystalline, by distillation, by silica gel column chromatography or even by high performance liquid chromatography (HPLC).

The present invention also has for a subject a method (2) for preparing a compound of formula (I) below for which $X=R_0=H$ and at least one of the $R_1$ and $R_2$ groups represents a substituted aryl group, comprising the following successive steps:

(a2) reaction of a compound of the formula $R_1Li$ for which $R_1$ is as defined previously but cannot be a hydrogen atom, with a compound of formula (Ia) below:

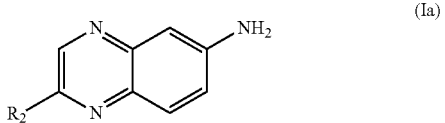

for which $R_2$ is as defined previously,
at a temperature comprised between −100 and 25° C., especially at approximately −78° C., to give a compound of formula (IV) below:

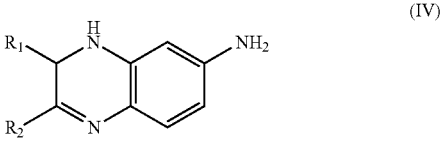

for which $R_1$ and $R_2$ are as defined previously with $R_1 \neq H$, at least one of the $R_1$ and $R_2$ groups representing a substituted aryl group, (b2) optionally, when $R_2=H$ in formula (IV) above, reaction of the compound of formula (IV) obtained in step (a2) above with a compound of formula $R_2Li$ for which $R_2$ is as defined previously but cannot be a hydrogen atom, at a temperature comprised between −78 and 25° C., especially at approximately 0° C., to give a compound of formula (V) below:

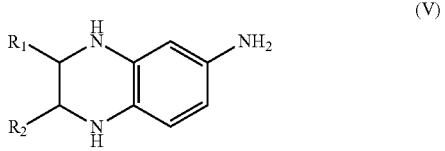

for which $R_1$ and $R_2$ are as defined previously with $R_1$ and $R_2 \neq H$, at least one of the $R_1$ and $R_2$ groups representing a substituted aryl group, and (c2) oxidation of the compound of formula (IV) or (V) obtained respectively in step (a2) or (b2) above to give a compound of formula (I) for which $R_1$ and $R_2$ are as previously defined, at least one of the $R_1$ and $R_2$ groups representing a substituted aryl group.

Preferably, X represents a hydrogen atom, one of the $R_1$ and $R_2$ groups represents a substituted aryl group, such as phenyl, especially substituted by one or more groups chosen from among a halogen atom, a $(C_1$-$C_6)$alkyl, $(C_1$-$C_6)$alkoxy, aryl, $N_3$, $NO_2$, $NH_2$, or —NH—$((C_1$-$C_6)$alkyl) group, and the other $R_1$ or $R_2$ group represents a saturated or unsaturated, linear or branched hydrocarbon chain comprising 1 to 10, preferably 1 to 6, carbon atoms, such as a $(C_1$-$C_6)$alkyl group.

Step (a2):

The compound $R_1Li$ used for this step is either commercial or easily accessible by synthesis methods well known to the skilled person.

The compounds of formula (Ia) can be prepared according to method (1) described above or by any other method known to the skilled person.

This reaction will advantageously be conducted in tetrahydrofuran as solvent.

Step (b2):

The compound $R_2Li$ used for this step is either commercial or easily accessible by synthesis methods well known to the skilled person.

This reaction will advantageously be conducted in tetrahydrofuran as solvent.

Step (c2):

This step will be conducted in the presence of an oxidant, such as $MnO_2$, allowing rearomatization of the quinoxaline nucleus.

This reaction will advantageously be conducted in chloroform used as solvent, particularly under reflux.

The compound thus obtained can be separated from the reaction medium by methods well-known to the person skilled in the art, such as, for example, by extraction, evaporation of the solvent or even by precipitation and filtration.

The compound can also be purified, if necessary, by techniques well known to the person skilled in the art, such as recrystallization if the compound is crystalline, by distillation, by silica gel column chromatography or even by high performance liquid chromatography (HPLC).

The present invention also has for a subject a method (3) for preparing a compound of formula (I) above for which $X \neq H$, comprising the following successive steps:

(a3) nitration or halogenation of a compound of formula (Ib) below:

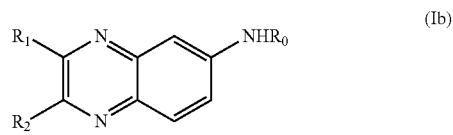

for which $R_0$, $R_1$ and $R_2$ are as defined previously to give a compound of formula (Ic) below:

(Ic)

for which $R_0$, $R_1$ and $R_2$ are as defined previously and X represents a halogen atom or a $NO_2$ group, and (b3) optionally, when X=$NO_2$ in formula (Ic) above, reduction of the compound of formula (Ic) obtained in step (a3) above to give a compound of formula (Id) below:

(Id)

for which $R_0$, $R_1$ and $R_2$ are as defined previously.

Step (a3):

The compounds of formula (Ib) can also be prepared, especially according to method (1) or (2) described above when $R_0$=H or according to method (4) below when $R_0$=$CH_2$—C≡CH.

The nitration reaction can be conducted in the presence of $KNO_3$ in sulfuric acid, especially at a temperature below 0° C., for example at approximately −10° C.

The halogenation step may be conducted with any halogenation agent known to the skilled person. In the case of bromination, bromine can be used, especially in acetic acid, for example at room temperature. In the case of chlorination, N-chlorosuccinimide can be used, especially in dichloromethane as solvent, for example at room temperature.

Step (b3):

The reducing agent used in step (b3) to reduce the nitro function into an amino function will advantageously be $SnCl_2$. This reaction may be performed in ethanol, preferably absolute ethanol, and advantageously under reflux thereof.

This reduction step may also be conducted under hydrogen atmosphere, in the presence of palladium on carbon.

Compound (Ic) or (Id) thus obtained can be separated from the reaction medium by methods well-known to the person skilled in the art, such as, for example, by extraction, evaporation of the solvent or even by precipitation and filtration.

The compound can also be purified, if necessary, by techniques well known to the person skilled in the art, such as recrystallization if the compound is crystalline, by distillation, by silica gel column chromatography or even by high performance liquid chromatography (HPLC).

Note that formulas (Ia) to (Id) previously described represent specific sub-formulas of formula (I) and should thus be considered as representing compounds of formula (I).

The present invention also has for a subject a method (4) for preparing a compound of formula (I) above for which $R_0$=$CH_2$—C≡CH, comprising the reaction of a compound of formula (Ie) below:

(Ie)

wherein:
X represents a hydrogen atom, a halogen atom such as bromine or chlorine, or an $NO_2$ group,
$R_0$ represents H, and
$R_1$ and $R_2$ each represent, independently of one another, a hydrogen atom; a saturated or unsaturated, linear or branched hydrocarbon chain comprising 1 to 10, preferably 1 to 6, carbon atoms; or an optionally substituted aryl group,
with a propargyl halide, preferably propargyl bromide.

Formula (Ie) therefore represents a specific sub-formula of formula (I) according to the invention (for which mainly $R_0$=H) and therefore should be considered as representing compounds of formula (I).

Compounds of formula (Ie) may be prepared notably according to methods (1), (2) and (3) described previously.

Compounds of formula (I) for which X=$NH_2$ cannot be used in this reaction because the propargyl moiety could also be added to this amino function. It is therefore preferable in this case to conduct the substitution reaction with a propargyl moiety from a compound for which $R_0$=H and X=$NO_2$ and then to reduce this nitro function into an amino function according to step (b3) of method (3) described above.

The reaction with propargyl halide is advantageously conducted in basic medium, especially in the presence of a base such as $K_2CO_3$. It can be conducted in the presence of iodide ions advantageously introduced by the addition of an iodide salt such as KI.

This reaction can be conducted in a solvent such as dimethylformamide, especially at a temperature of 100° C.

Additional protection/deprotection steps may optionally be necessary to protect functionalities that would be sensitive/reactive under the reaction conditions, which can be assessed by the skilled person.

The compound thus obtained can be separated from the reaction medium by methods well-known to the person skilled in the art, such as, for example, by extraction, evaporation of the solvent or even by precipitation and filtration.

The compound can also be purified, if necessary, by techniques well known to the person skilled in the art, such as recrystallization if the compound is crystalline, by distillation, by silica gel column chromatography or even by high performance liquid chromatography (HPLC).

The present invention will be understood more clearly in light of the following non-limiting examples.

FIGURES

Figure 6:
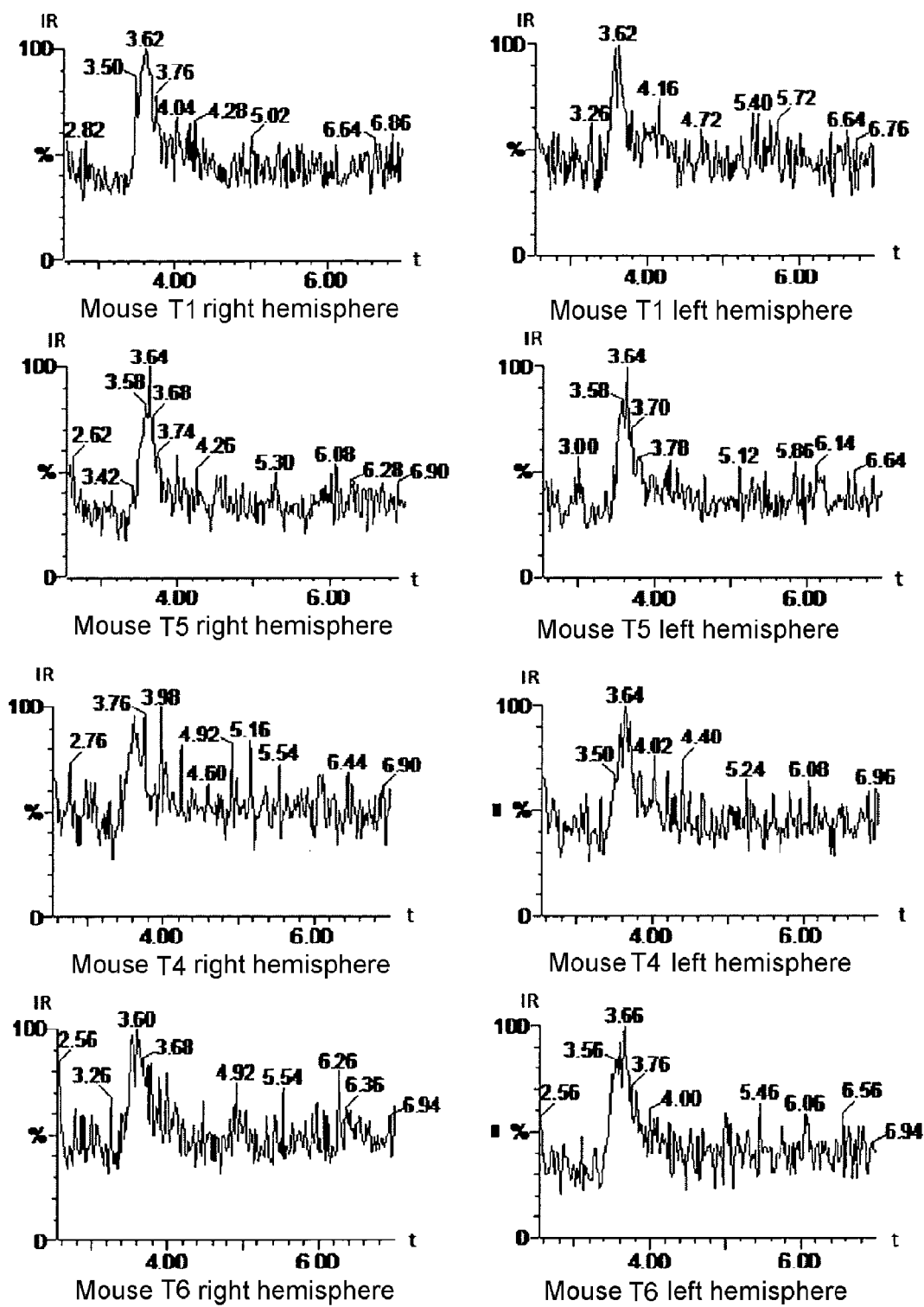

FIG. 6 shows chromatograms x-axis: time (min); y-axis: relative intensity (%)) obtained by HPLC-MS/MS from brain extracts of different mice of the IP study euthanized 4 and 6 h after the last treatment, the extracts being kept for 40 days at 4° C. before analysis to detect compound 4bc.

Figure 7:
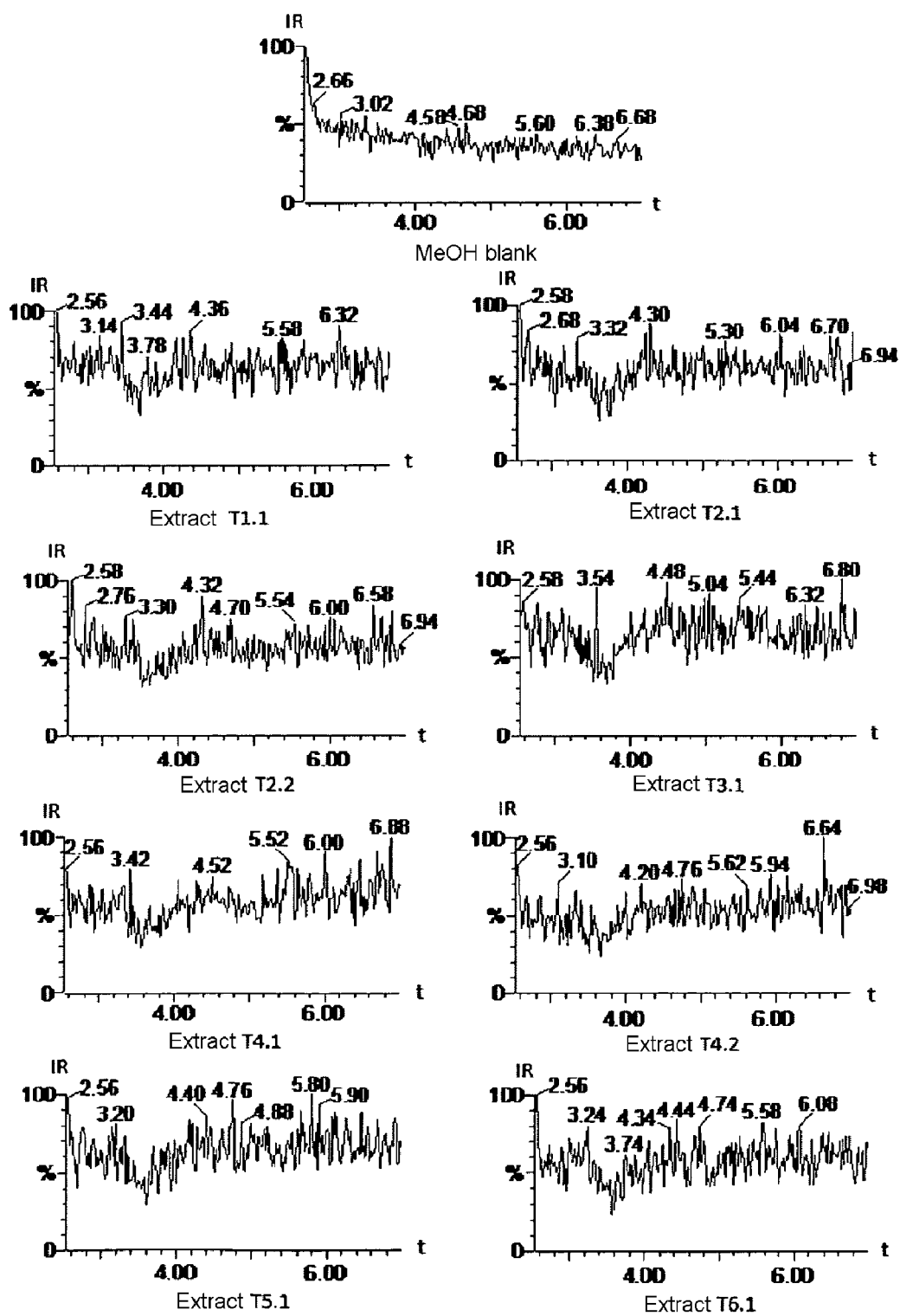

FIG. 7 shows chromatograms x-axis: time (min); y-axis: relative intensity (%)) obtained by HPLC-MS/MS from brain extracts of different mice of the per os study so as to verify the presence of compound 4bc.

Figure 8:
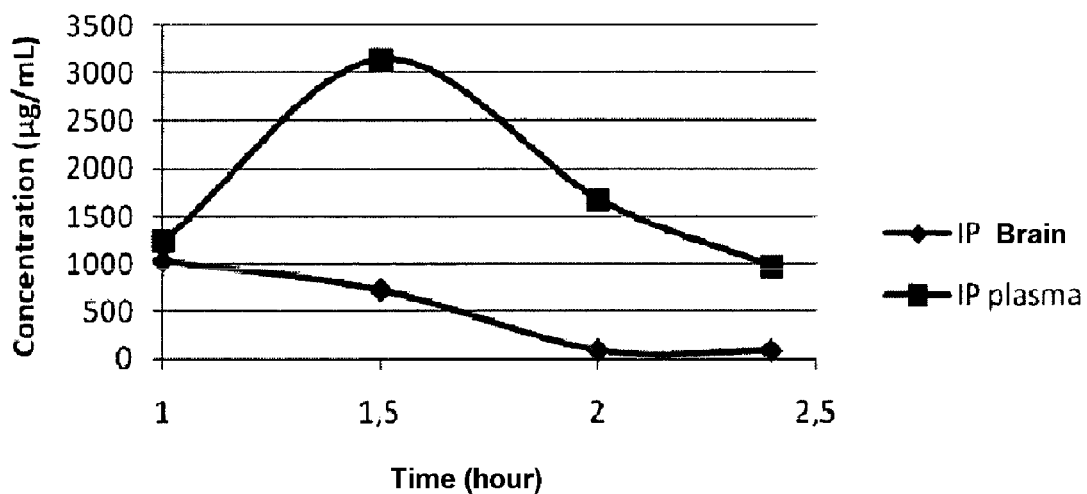

FIG. 8 shows the kinetics in mouse brain and plasma of compound 4bc after IP administration.

Figure 9:
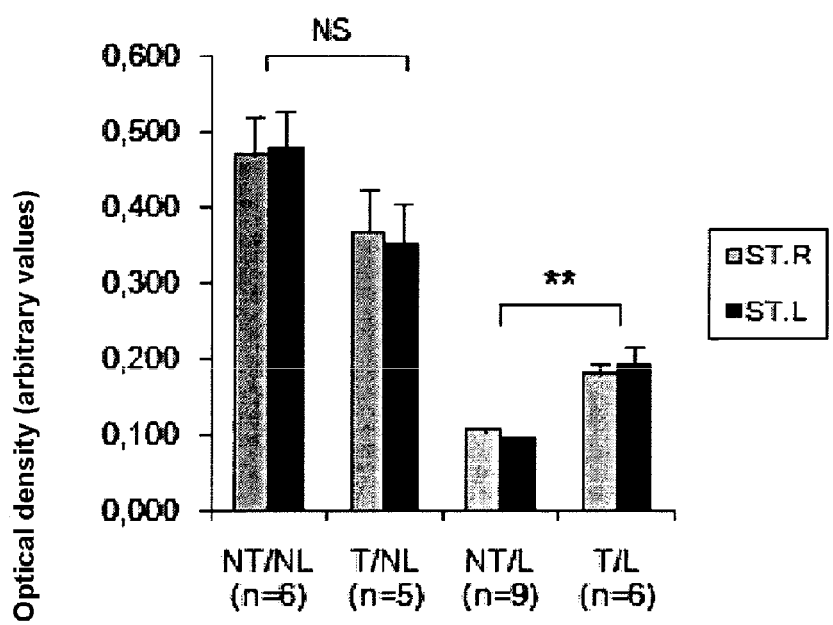

FIG. 9 shows the mean optical density of the right striatum (ST.R) and left striatum (ST.L) of the different mouse groups (NT/NL: not treated/not lesioned; T/NL: treated/not lesioned; NT/L: not treated/lesioned; T/L: treated/lesioned) used in the in vivo study of neuroprotection by compound 4bc administered orally, with regard to a toxin—MPTP—administered intranasally.

Figure 10:
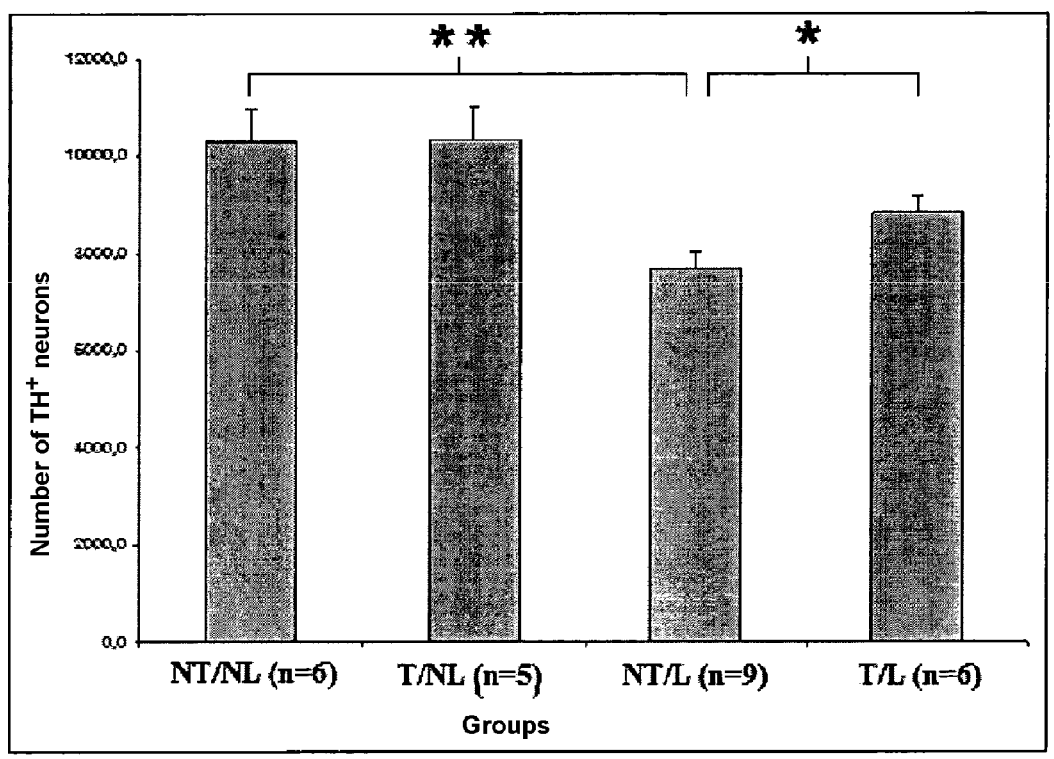

FIG. 10 shows the mean quantity of tyrosine hydroxylase positive (TH$^+$) neurons in the substantia nigra of the different mouse groups (NT/NL: not treated/not lesioned; T/NL: treated/not lesioned; NT/L: not treated/lesioned; T/L: treated/lesioned) used in the in vivo study of neuroprotection by compound 4bc administered orally, with regard to a toxin—MPTP—administered intranasally.

EXAMPLES

The following abbreviations were used in this part.
AMP Adenosine 3',5'-monophosphate
dbcAMP Dibutyryl cyclic adenosine 3',5'-monophosphate
DCM Dichloromethane
DMSO Dimethylsulfoxide
equiv. Equivalent
ESI Electrospray ionization
EtOH$_{abs}$ Absolute ethanol
HPLC High performance liquid chromatography
HPLC—High performance liquid chromatography coupled MS/MS with two mass spectrometries
IR Infrared
NCS N-chloro-succinimide
MPTP 1-methyl-4-phenyl-1,2,3,6-tetrahydropyridine
MRM Multiple Reaction Monitoring
MS Mass spectrum
NMR Nuclear magnetic resonance
RT Room temperature
THF Tetrahydrofuran
UV Ultraviolet The compounds were named as follows:
first suffix=$R_2$
second suffix=$R_1$
with a=H, b=Me, c=Ph, d=n-Bu, e=n-Hex, f=s-Bu, g=t-Bu, h=p-methoxyphenyl, i=m-methoxyphenyl, j=3,4-dimethoxyphenyl, k=3,4,5-trimethoxyphenyl, l=2-naphthyl, m=p-fluorophenyl, n=p-methylphenyl, o=p-chlorophenyl, p=3,4-dichlorophenyl, q=biphenyl.

I. Synthesis of Compounds According to the Invention 1.1. General Procedures

A Hinsberg condensation between 4-nitrophenylene-1,2-diamine 1 and glyoxal 2aa, pyruvaldehyde 2ba or phenylglyoxal 2ca, all commercially available compounds, regioselectively yields 6-nitroquinoxaline 3aa, 2-methyl-6-nitroquinoxaline 3ba or 2-phenyl-6-nitroquinoxaline 3ca. Reducing the nitro function into amine function by stannous chloride (or hydrogen in the presence of palladium on carbon) gives 6-aminoquinoxaline 4aa, 2-methyl-6-aminoquinoxaline 4ba and 2-phenyl-6-aminoquinoxaline 4ca (see Diagram 1).

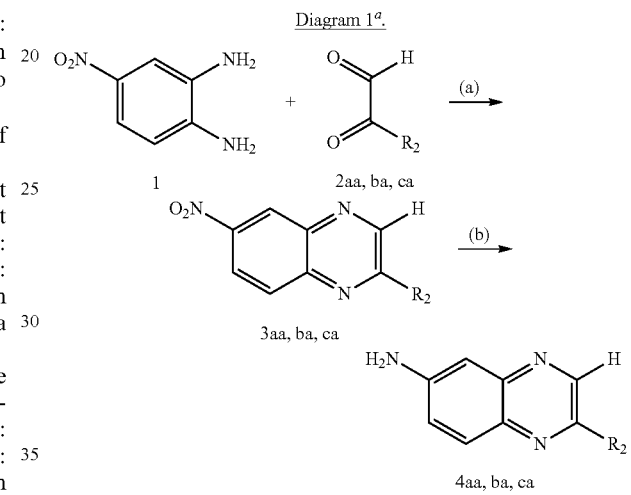

$^a$Reagents and conditions: (a) H$_2$O, reflux. (b) SnCl$_2$, EtOH$_{abs}$, reflux, or H$_2$, Pd/C, 60° C.

Substitutions in positions 2 and 3 of quinoxaline are introduced by a reaction involving organolithium compounds. Actually, the substitution at position 3 of the ring by an organolithium is selective at −78° C. in compounds 4aa, 4ba or 4ca, thus yielding quinoxalines with various substituents at position 3. A second substitution at position 2 of the ring is possible at 0° C. when position 3 is already occupied by a substituent and position 2 is free, yielding non-symmetrical disubstituted quinoxalines. Rearomatization with manganese dioxide yields compounds 4 with various substituents (see diagram 2). It is also possible to obtain disubstituted quinoxaline 4 by conducting a Hinsberg reaction described previously with a diketone instead of ketoaldehyde (see diagram 3).

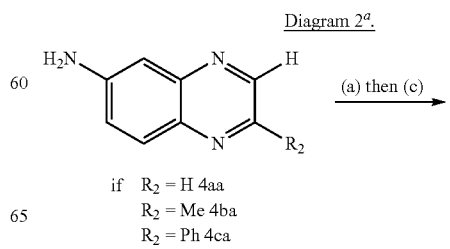

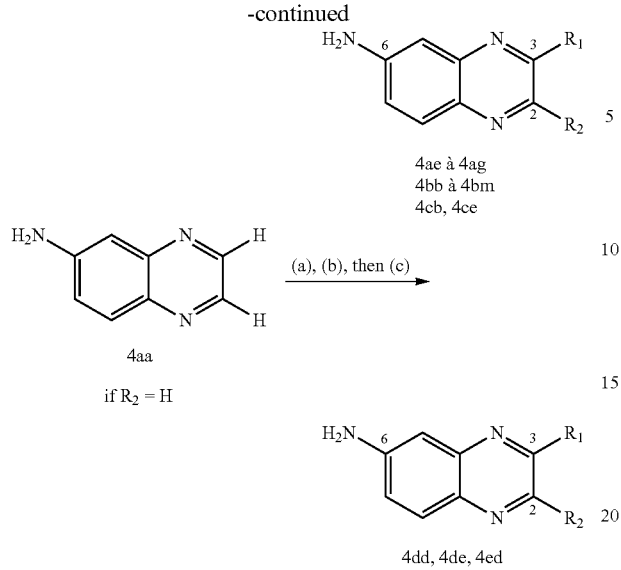
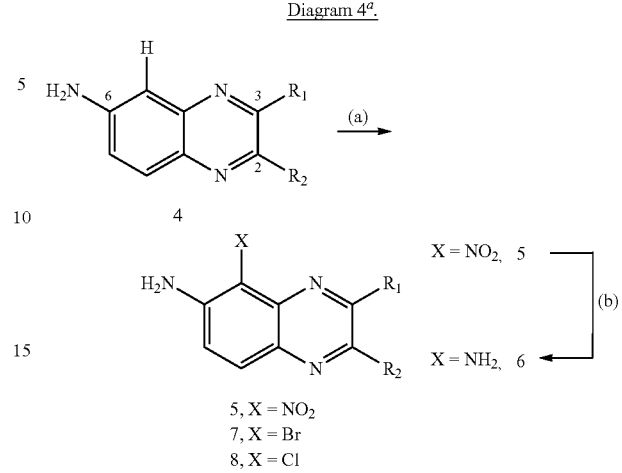

*Reagents and conditions: (a) R₁Li, THF, -78° C. (b) R₂Li, THF, -78° C. then 0° C. (b) MnO₂, CHCl₃, reflux.

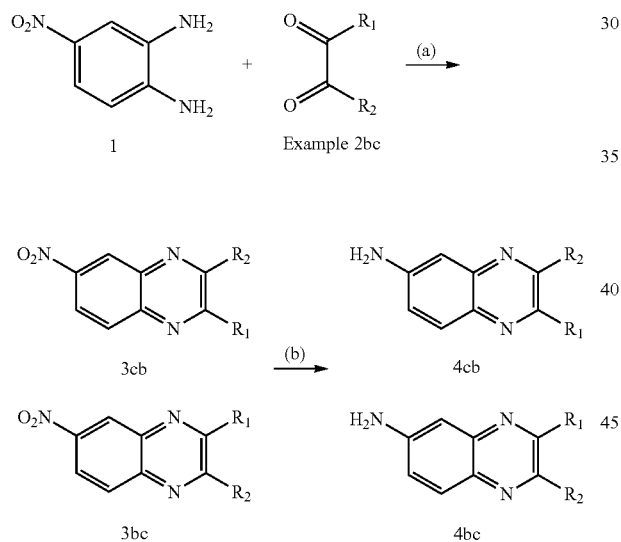

*Reagents and conditions: (a) H₂O, reflux. (b) SnCl₂, EtOH$_{abs}$, reflux, or H₂, Pd/C, 60° C. (ii) Chromatography, isomer separation.

Quinoxalines 4 are selectively substituted at position 5 by aromatic substitution with electrophiles such as the nitronium ion produced with potassium nitrate in sulfuric acid giving nitrated compounds 5, as well as halides such as bromine in acetic acid giving halogenated compounds 7. From nitrated derivatives 5, aminated compounds 6 are obtained by reduction with tin (II) chloride under reflux in absolute ethanol or even under hydrogen atmosphere in the presence of Pd/C at 60° C. (see diagram 4).

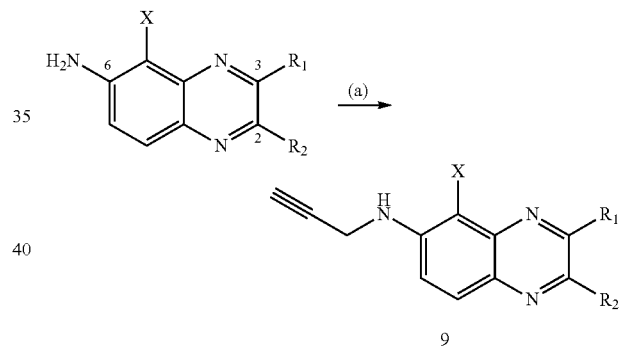

*Reagents and conditions: (a) KNO₃, H₂SO₄, -10° C. or Br₂, AcOH, RT or NCS, DCM, RT (b) SnCl₂, EtOH$_{abs}$, reflux, or H₂, Pd/C, 60° C.

The amine function of 6-amino-quinoxalines can also be substituted by a propargyl group by reacting the quinoxalines with propargyl bromide under basic conditions in DMI at 100° C. (see diagram 5).

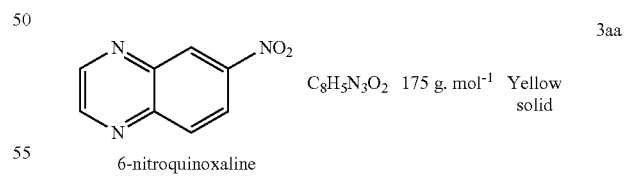

*Reagents and conditions: (a) KI, K₂CO₃, DMI, 100° C.

I.2 Synthesis of Compounds 3

An aqueous solution (30 mL) of commercial 4-nitrophenylene-1,2-diamine (1.53 g, 10 mmol, 1 equiv.) and commercial glyoxal (40% in water) (1.8 mL, 10 mmol, 1 equiv.) was heated under reflux for 4 hours. After cooling, the precipitate was recovered by filtration and washed with water. The solid obtained was oven-dried at 100° C. for 24 h.

Yield: 93% (1.63 g). ¹H NMR (400 MHz, CDCl₃) δ ppm: 8.26 (d, J=9.2 Hz, 1H); 8.52 (dd, J=9.2 Hz, J=2.4 Hz, 1H); 9.01 (s, 3H). ¹³C NMR (50 MHz, CDCl₃) δ ppm: 123.4, 125.9, 131.3, 141.9, 145.3, 147.0, 147.6, 147.9. IR ν cm$^{-1}$: 3090, 3055, 1610, 1585, 1545, 1520, 1490, 1445, 1370, 1345, 1295, 1205, 1190, 1130, 1075, 955, 930, 870, 850, 810, 740. MS (ESI) m/z: 176 ([M+H]$^+$, 23).

3ba

C$_9$H$_7$N$_3$O$_2$  189 g. mol$^{-1}$  Tan solid 2-methyl-6-nitroquinoxaline

An aqueous solution (50 mL) of commercial 4-nitro-phenylene-1,2-diamine (3.06 g, 20 mmol, 1 equiv.) and commercial pyruvic aldehyde (40% in water) (3.6 mL, 20 mmol, 1 equiv.) was heated under reflux for 1.5 hours. After cooling, the precipitate was recovered by filtration and washed with water. The solid obtained was oven-dried at 100° C. for 24 h.

Yield: 90% (3.40 g). $^1$H NMR (400 MHz, CDCl$_3$) δ ppm: 2.82 (s, 3H); 8.10 (d, J=8.4 Hz, 1H); 8.45 (d, J=8.0 Hz, 1H); 8.87 (s, 1H); 8.92 (s, 1H). $^{13}$C NMR (50 MHz, CDCl$_3$) δ ppm: 22.8, 123.3, 125.5, 130.2, 139.7, 144.5, 147.0, 148.1, 157.3. IR ν cm$^{-1}$: 3045, 2955, 1615, 1565, 1520, 1490, 1455, 1390, 1340, 1295, 1210, 1185, 1080, 965, 940, 930, 860, 830, 795, 745, 715. MS (ESI): 190 ([M+H]$^+$, 100).

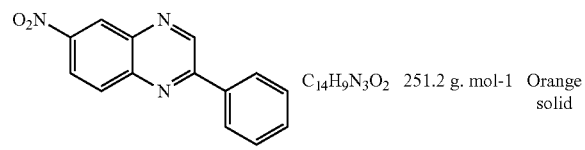

3ca

C$_{14}$H$_9$N$_3$O$_2$  251.2 g. mol-1  Orange solid 6-nitro-2-phenylquinoxaline An aqueous solution (40 mL) of commercial 4-nitro-phenylene-1,2-diamine (1.530 g, 10 mmol, 1 equiv.) and commercial phenylglyoxal monohydrate (1.522 g 10 mmol, 1 equiv.) was heated under reflux for 1 hour. After cooling, the precipitate was recovered by filtration and washed with water. The solid obtained was oven-dried at 100° C. for 24 h.

Yield: 98% (2.455 g). $^1$H NMR (400 MHz, CDCl$_3$) δ ppm: 7.61 (m, 3H), 8.24-8.29 (m, 3H), 8.55 (dd, J=9.3 and 2.3 Hz, 1H), 9.02 (d, J=2.4 Hz, 1H), 9.49 (s, 1H). $^{13}$C NMR (100 MHz, CDCl$_3$) δ ppm: 123.8, 125.6, 127.9 (2C), 129.4 (2C), 131.2, 131.4, 135.6, 140.3, 144.9, 145.5, 147.4, 154.3.

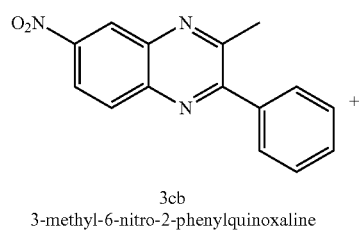

3cb
3-methyl-6-nitro-2-phenylquinoxaline

+

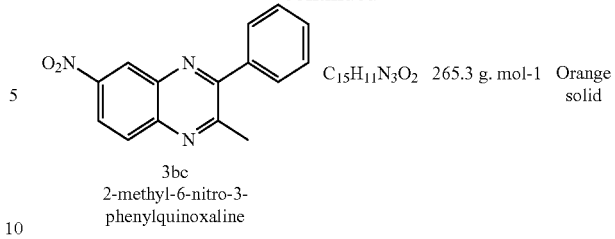

3bc
2-methyl-6-nitro-3-phenylquinoxaline

C$_{15}$H$_{11}$N$_3$O$_2$  265.3 g. mol-1  Orange solid

A water-alcohol solution (20 mL 50:50 isopropanol/water) of commercial 4-nitro-phenylene-1,2-diamine (0.516 g, 3.4 mmol, 1 equiv.) and commercial phenyl-1,2-propane-dione (0.45 mL, 3.4 mmol 1 equiv.) was heated under reflux for 1.5 hours. After addition of 30 mL of water and cooling, the precipitate was recovered by filtration and washed with water. The orange-colored solid obtained was oven-dried at 100° C. for 24 h.

Yield: 93% (834.4 mg).

I.3. Synthesis of Compounds 4

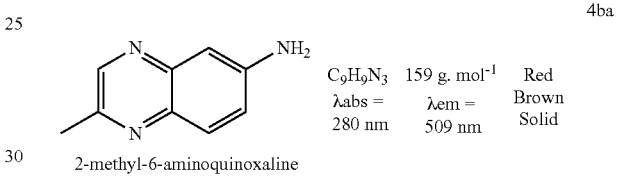

4ba

C$_9$H$_9$N$_3$  159 g. mol$^{-1}$  Red Brown Solid
λabs = 280 nm
λem = 509 nm 2-methyl-6-aminoquinoxaline 318 mg of Pd/C (10% m/m) were added to a solution of compound 3-methyl-6-nitroquinoxaline 3ba (20 mmol, 1 equiv.) in ethanol (100 mL). The reaction was stirred at 60° C. and placed under hydrogen for 4 h. After cooling, the reaction was filtered on Celite and rinsed with ethanol and the filtrate was concentrated under reduced pressure.

Yield: 80% (2.54 g). $^1$H NMR (300 MHz, CDCl$_3$) δ ppm: 2.62 (s, 3H); 4.22 (s, 2H); 7.09-7.11 (m, 2H); 7.73 (d, J=4.2 Hz, 1H); 8.52 (s, 1H). $^{13}$C NMR (75 MHz, CDCl$_3$) δ ppm: 149.3, 147.1, 145.7, 142.5, 141.7, 136.8, 129.4, 121.7, 108.1, 121.8. IR ν cm$^{-1}$: 3330, 3205, 3055, 2920, 1615, 1555, 1500, 1475, 1420, 1365, 1345, 1310, 1230, 1210, 1170, 1130, 1015, 970, 940, 910, 830, 780, 755, 730. MS (ESI) m/z: 160 ([M+H]$^+$, 100).

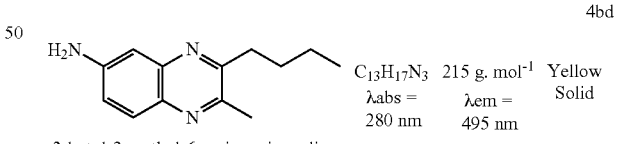

4bd

C$_{13}$H$_{17}$N$_3$  215 g. mol$^{-1}$  Yellow Solid
λabs = 280 nm
λem = 495 nm 3-butyl-2-methyl-6-aminoquinoxaline n-BuLi (1 mL, 2.5 mmol, 1.5 equiv.) was added slowly to a solution of 2-methyl-6-aminoquinoxaline (1 mmol, 1 equiv.) in THF (2 mL), placed under inert nitrogen atmosphere at −78° C. The solution immediately turned dark red. The reaction mixture was stirred at −78° C. for 2.5 hours, hydrolyzed by 3 mL of a saturated NH$_4$Cl solution and then extracted three times with ethyl acetate (3×20 mL). The combined organic phases were then washed with 100 mL of an aqueous saturated NaCl solution, dried on MgSO$_4$, filtered and then concentrated under reduced pressure. The residue obtained was then taken up in CHCl$_3$ (20 mL) and then 430 mg of MnO$_2$ (5 mmol, 5 equiv.) are added. The solution was heated under reflux for 4 hours. The reaction mixture was then hydrolyzed by 2 mL of water, filtered on Celite and then washed with ethyl acetate (30 mL). The organic phase was dried with MgSO$_4$ and then evaporated under reduced pressure. Purification on silica gel in a mixture of cyclohexane and ethyl acetate in a proportion of 80:20 yielded compound 4bd.

Yield: 75% (1.61 g). $^1$H NMR (300 MHz, CDCl$_3$) δ ppm: 0.98 (t, J=7.2 Hz, 3H); 1.47 (m, 2H); 1.77 (m, 2H); 2.90 (t, J=7.8 Hz, 2H); 4.04 (s, 2H); 7.07 (m, 2H); 7.75 (d, J=8.1 Hz, 1H). $^{13}$C NMR (75 MHz, CDCl$_3$) δ ppm: 13.9, 22.3, 22.8, 30.5, 35.7, 108.1, 120.5, 129.1, 135.7, 142.7, 146.9, 148.9, 156.9. IR ν cm$^{-1}$: 3320, 3170, 2955, 2925, 2870, 1655, 1620, 1555, 1500, 1460, 1375, 1345, 1315, 1285, 1250, 1160, 1130, 1105, 1075, 1010, 970, 955, 875, 855, 830, 790, 780, 740, 705. MS (ESI) m/z: 216 ([M+H]$^+$, 100).

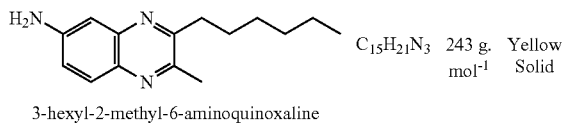

4be
C$_{15}$H$_{21}$N$_3$ 243 g. mol$^{-1}$ Yellow Solid 3-hexyl-2-methyl-6-aminoquinoxaline Preparation method similar to the one used for the synthesis of compound 4bd. Yield: 65% (158 mg). $^1$H NMR (300 MHz, CDCl$_3$) δ ppm: 0.89 (t, J=6.6 Hz, 3H); 1.21 (m, 4H); 1.47 (m, 2H); 1.77 (m, 2H); 2.68 (s, 3H); 2.92 (t, J=8.1 Hz, 2H); 4.05 (s, 2H); 7.06 (m, 2H); 7.77 (d, J=8.4 Hz, 1H). $^{13}$C NMR (75 MHz, CDCl$_3$) δ ppm: 14.0, 22.3, 22.6, 28.4, 29.4, 31.6, 108.2, 120.5, 129.2, 135.7, 142.8, 146.9, 148.8, 156.9. IR ν cm$^{-1}$: 3340, 3225, 2955, 2925, 2855, 2360, 2345, 2145, 2005, 1690, 1620, 1585, 1545, 1500, 1465, 1375, 1345, 1240, 1135, 1080, 1005, 830. MS (ESI) m/z: 244 ([M+H]$^+$, 100).

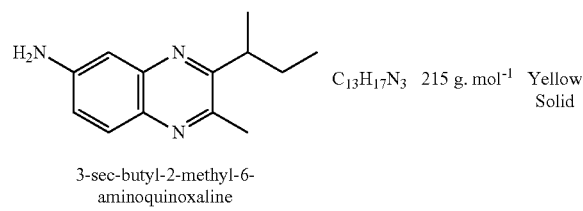

4bf
C$_{13}$H$_{17}$N$_3$ 215 g. mol$^{-1}$ Yellow Solid 3-sec-butyl-2-methyl-6-aminoquinoxaline Preparation method similar to the one used for the synthesis of compound 4bd.

Yield: 65% (140 mg). $^1$H NMR (300 MHz, CDCl$_3$) δ ppm: 0.89 (t, J=7.5 Hz, 3H); 1.32 (d, J=6.9 Hz, 3H); 1.63 (m, 1H); 1.92 (m, 1H); 2.69 (s, 3H); 3.14 (sex, J=6.9 Hz, 1H); 4.02 (s, 2H); 7.09 (m, 2H); 7.74 (d, J=8.7 Hz, 1H). $^{13}$C NMR (75 MHz, CDCl$_3$) δ ppm: 12.3, 19.3, 22.4, 28.9, 38.9, 108.5, 120.5, 129.0, 135.3, 140.6, 146.8, 148.7, 160.7. IR ν cm$^{-1}$: 3345, 3220, 2960, 2925, 2870, 2360, 1620, 1555, 1500, 1460, 1375, 1320, 1235, 1180, 1130, 1075, 1050, 1020, 1000, 910, 855, 830, 730. MS (ESI) m/z: 216 ([M+H]$^+$, 100).

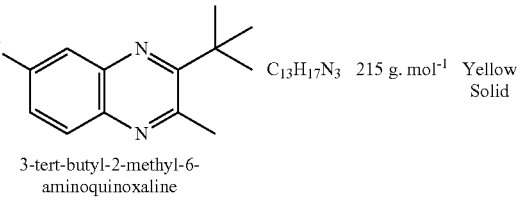

4bg
C$_{13}$H$_{17}$N$_3$ 215 g. mol$^{-1}$ Yellow Solid 3-tert-butyl-2-methyl-6-aminoquinoxaline Preparation method similar to the one used for the synthesis of compound 4bd.

Yield: 25% (54 mg). $^1$H NMR (300 MHz, CDCl$_3$) δ ppm: 1.51 (s, 9H); 2.84 (s, 3H); 4.22 s, 2H); 7.09 (m, 2H); 7.73 (d, J=9.0 Hz, 1H). $^{13}$C NMR (75 MHz, CDCl$_3$) δ ppm: 25.7, 29.4, 108.8, 120.7, 128.7, 134.9, 141.5, 146.8, 148.4, 162.2. IR ν cm$^{-1}$: 3340, 3220, 2965, 2930, 2870, 2360, 1620, 1565, 1545, 1495, 1455, 1410, 1395, 1365, 1325, 1245, 1200, 1130, 1070, 1000, 910, 855, 830, 785, 730. MS (ESI) m/z: 216 ([M+H]$^+$, 100).

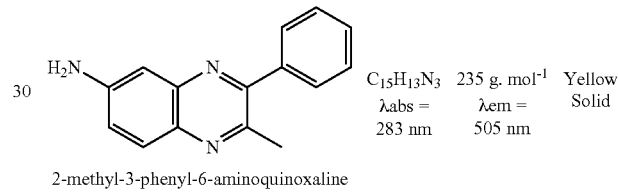

4bc
C$_{15}$H$_{13}$N$_3$ 235 g. mol$^{-1}$ Yellow Solid
λabs = 283 nm    λem = 505 nm 2-methyl-3-phenyl-6-aminoquinoxaline Preparation method similar to the one used for the synthesis of compound 4bd.

Yield: 75% (176 mg). $^1$H NMR (300 MHz, CDCl$_3$) δ ppm: 2.68 (s, 3H); 3.88 (s, 2H); 7.16 (m, 2H); 7.48 (m, 3H); 7.61 (m, 2H); 7.83 (d, J=8.7 Hz, 1H). $^{13}$C NMR (75 MHz, CDCl$_3$) δ ppm: 23.8, 108.4, 121.7, 128.4, 128.7, 128.9, 129.2, 136.2, 139.4, 142.6, 147.3, 148.0, 154.8. IR ν cm$^{-1}$: 3210, 2965, 2925, 2480, 2215, 1965, 1625, 1560, 1515, 1490, 1420, 1380, 1345, 1325, 1255, 1160, 1005, 970, 905, 830, 775, 725. MS (ESI) m/z: 236 ([M+H]$^+$, 100).

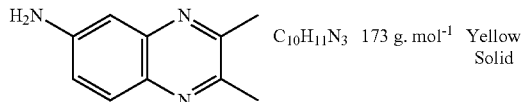

4bb
C$_{10}$H$_{11}$N$_3$ 173 g. mol$^{-1}$ Yellow Solid 2,3-dimethyl-6-aminoquinoxaline Preparation method similar to the one used for the synthesis of compound 4bd.

Yield: 8% (176 mg). $^1$H NMR (200 MHz, CDCl$_3$) δ ppm: 2.58 (s, 3H); 2.59 (s, 3H); 4.11 (s, 2H); 6.98 (m, 2H); 7.67 (d, J=8.4 Hz, 1H). $^{13}$C NMR (75 MHz, CDCl$_3$) ppm: 22.52, 22.95, 107.86, 120.45, 129.08, 135.78, 142.68, 147.04, 149.01, 153.21. IR ν cm$^{-1}$: 680, 728, 793, 829, 913, 949, 996, 1128, 1160, 1243, 1340, 1379, 1445, 1466, 1501, 1560, 1618, 2919, 2947, 2990, 3030, 3208, 3329. MS (ESI) m/z: 174 ([M+H]$^+$, 100).

4aa 6-aminoquinoxaline

C₈H₇N₃  145 g. mol⁻¹  Yellow Solid
λabs = 280 nm  λem = 506 nm

Preparation method similar to the one used for the synthesis of compound 4ba.

Yield: 80% (2.32 g). ¹H NMR (400 MHz, CDCl₃) δ ppm: 4.10 (s, 2H); 7.12 (d, J=2.4 Hz, 1H); 7.15 (dd, J=8.8 Hz, J=2.4 Hz, 1H); 7.84 (d, J=8.8 Hz, 1H); 8.52 (s, 1H); 8.62 (s, 1H). ¹³C NMR (50 MHz, CDCl₃) δ ppm: 148.1, 144.9, 140.9, 137.9, 130.3, 122.0, 107.8. IR ν cm⁻¹: 3395, 3315, 3185, 3055, 1645, 1615, 1545, 1500, 1470, 1435, 1370, 1310, 1225, 1210, 1135, 1030, 960, 860, 815, 765. MS (ESI) m/z: 146 ([M+H]⁺, 100).

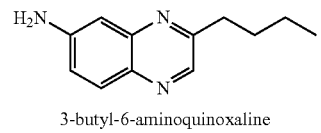

4ad 3-butyl-6-aminoquinoxaline

C₁₂H₁₅N₃  201 g. mol⁻¹  Yellow Solid

Preparation method similar to the one used for the synthesis of compound 4bd.

Yield: 54% (108 mg). ¹H NMR (400 MHz, CDCl₃) δ ppm: 0.93 (t, J=7.2 Hz, 3H); 1.40 (m, 2H); 1.74-1.82 (m, 2H); 2.89 (t, J=7.5 Hz, 2H); 4.17 (s, 2H); 7.08 (m, 2H); 7.81 (d, J=8.1 Hz, 1H); 8.44 (s, 1H). ¹³C NMR (50 MHz, CDCl₃) δ ppm: 13.9, 22.6, 31.7, 36.2, 107.9, 120.7, 130.1, 136.1, 141.8, 144.0, 147.9, 157.7. IR ν cm⁻¹: 3335, 3210, 2955, 2930, 2860, 1620, 1550, 1510, 1465, 1435, 1370, 1275, 1240, 1165, 1130, 1080, 995, 955, 905, 855, 830, 775, 730. MS (ESI) m/z: 202 ([M+H]⁺, 100).

4dd 2,3-dibutyl-6-aminoquinoxaline

C₁₆H₂₃N₃  257 g. mol⁻¹  Yellow Solid

Minor product obtained during the synthesis of compound 4ad.

¹H NMR (200 MHz, CDCl₃) δ ppm: 0.95 (t, J=7.2 Hz, 6H); 1.48 (m, 4H); 1.76 (m, 4H); 2.92 (m, 4H); 4.05 (s, 2H); 7.05 (m, 2H); 7.75 (d, J=8.8 Hz, 1H). ¹³C NMR (50 MHz, CDCl₃) δ ppm: 13.9, 22.9, 31.2, 31.3, 35.2, 34.9, 108.7, 120.5, 129.4, 135.9, 142.6, 146.9, 152.6, 156.6. IR ν cm⁻¹: 730, 830, 862, 962, 1076, 1137, 1173, 1232, 1346, 1375, 1419, 1463, 1499, 1564, 1629, 2870, 2928, 2953, 3197, 3317, 3444. MS (ESI) m/z: 258 ([M+H]⁺, 42).

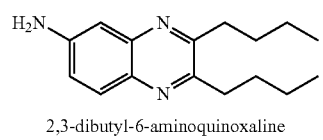

4ae 3-hexyl-6-aminoquinoxaline

C₁₄H₁₉N₃  229 g. mol⁻¹  Yellow solid
λabs = 280 nm  λem = 502 nm

Preparation method similar to the one used for the synthesis of compound 4bd.

Yield: 53% (122 mg). ¹H NMR (400 MHz, CDCl₃) δ ppm: 0.87 (t, J=6.9 Hz, 3H); 1.29 (m, 6H); 1.77 (m, 4H); 2.88 (t, J=7.8 Hz, 2H); 4.14 (s, 2H); 7.09 (m, 2H); 7.80 (d, J=8.7 Hz, 1H); 8.42 (s, 1H). ¹³C NMR (50 MHz, CDCl₃) δ ppm: 14.0, 22.5, 29.1, 29.6, 31.6, 36.5, 108.0, 120.7, 130.0, 136.1, 141.8, 144.0, 147.9, 157.7. IR ν cm⁻¹: 3340, 3215, 2955, 2925, 2855, 2360, 1620, 1550, 1510, 1465, 1370, 1340, 1280, 1235, 1185, 1160, 1135, 1080, 975, 905, 830, 775, 730. MS (ESI) m/z: 230 ([M+H]⁺, 100).

4af 3-sec-butyl-6-aminoquinoxaline

C₁₂H₁₅N₃  201 g. mol⁻¹  Yellow solid

Preparation method similar to the one used for the synthesis of compound 4bd.

Yield: 40% (80 mg). ¹H NMR (300 MHz, CDCl₃) δ ppm: 0.90 (t, J=7.5 Hz, 3H); 1.37 (d, J=7.2 Hz, 3H); 1.73 (m, 1H); 1.88 (m, 1H); 2.96 (m, 1H); 4.12 (s, 2H); 7.09 (m, 2H); 7.84 (d, J=9.6 Hz, 1H); 8.45 (s, 1H). ¹³C NMR (75 MHz, CDCl₃) ppm: 12.1, 19.9, 29.6, 42.1, 108.1, 120.7, 130.0, 136.3, 141.0, 144.0, 147.8, 161.4. IR ν cm⁻¹: 3340, 3215, 2960, 2925, 2875, 2360, 1620, 1545, 1510, 1460, 1430, 1370, 1275, 1250, 1230, 1175, 1130, 1275, 1250, 1230, 1175, 1130, 1085, 1050, 1015, 980, 960, 905, 855, 830, 775, 735. MS (ESI) m/z: 202 ([M+H]⁺, 100).

4ag 3-tert-butyl-6-aminoquinoxaline

C₁₂H₁₅N₃  201 g. mol⁻¹  Yellow solid

Preparation method similar to the one used for the synthesis of compound 4bd.

Yield: 26% (52 mg). ¹H NMR (300 MHz, CDCl₃) δ ppm: 1.44 (s, 9H); 4.21 (s, 2H); 7.05 (m, 1H); 7.78 (d, J=9.3 Hz, 1H); 8.67 (s, 1H). ¹³C NMR (75 MHz, CDCl₃) ppm: 29.6, 36.9, 108.2, 120.7, 127.9, 135.6, 139.1, 143.2, 147.8, 163.6. IR ν cm⁻¹: 3335, 3215, 2960, 1620, 1545, 1505, 1460, 1430, 1365, 1280, 1245, 1200, 1110, 1020, 975, 955, 905, 855, 830, 775, 730. MS (ESI) m/z: 202 ([M+H]⁺, 100).

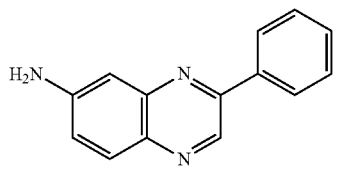

4ac 3-phenyl-6-aminoquinoxaline

C$_{14}$H$_{11}$N$_3$    221 g. mol$^{-1}$    Yellow solid

Preparation method similar to the one used for the synthesis of compound 4bd.

Yield: 28% (62 mg). $^1$H NMR (300 MHz, CDCl$_3$) δ ppm: 4.21 (brs, 2H NH), 7.16 (dd, J=8.9 and 2.5 Hz, 1H), 7.21 (d, J=2.5 Hz, 1H), 7.49-7.57 (m, 3H), 7.89 (d, J=8.9 Hz, 1H), 8.14 (dd, J=7.2 and 1.2 Hz, 2H), 9.04 (s, 1H). $^{13}$C NMR (75 MHz, CDCl$_3$) δ ppm: 107.5, 120.5, 126.5 (2C), 128.0 (2C), 128.8, 129.1, 135.7, 136.3, 138.5, 143.2, 147.2, 151.1. MS (ESI) m/z: 222.2 ([M+H]$^+$, 100). Purity (HPLC/UV 254 nm): 100%.

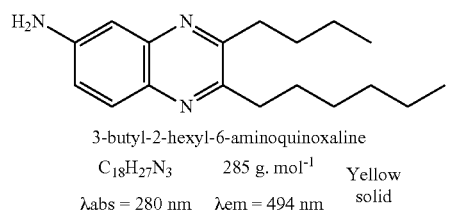

4ed 3-butyl-2-hexyl-6-aminoquinoxaline

C$_{18}$H$_{27}$N$_3$    285 g. mol$^{-1}$    Yellow solid

λabs = 280 nm    λem = 494 nm 1 mL (2.5 mmol, 2.5 equiv.) of 2.5 M n-BuLi is added to a solution of 6-aminoquinoxaline 4aa (1 mmol, 1 equiv.) in THF (2 mL), placed under inert nitrogen atmosphere at −78° C. The solution immediately turned dark red. The mixture was stirred for 2.5 hours. The solution was then placed at 0° C. and 0.8 mL (2 mmol, 2 equiv.) of 2.5 M n-HexLi were immediately added dropwise. The reaction mixture was stirred at 0° C. for 2 hours and then hydrolyzed by 5 mL of an aqueous saturated NH$_4$Cl solution and then extracted with ethyl acetate (3×20 mL). The combined organic phases were then washed with 100 mL of a saturated aqueous NaCl solution, dried on MgSO$_4$, filtered and then concentrated under reduced pressure. The residue obtained was taken up in CHCl$_3$ (20 mL) and then 430 mg of MnO$_2$ (5 mmol, 5 equiv.) were added and the mixture was stirred under reflux for 4 h. The reaction mixture was hydrolyzed by 2 mL of water and then filtered on Celite. The organic phase was dried with MgSO$_4$ and then concentrated under reduced pressure. Purification by silica gel chromatography in a cyclohexane:ethyl acetate mixture in a proportion of 50:50 yielded compound 4ed.

Yield: 49% (140 mg). $^1$H NMR (300 MHz, CDCl$_3$) δ ppm: 0.96 (m, 6H); 1.25 (m, 8H); 1.40 (m, 2H); 1.70 (m, 2H); 2.90 (m, 4H); 4.10 (s, 2H); 7.05 (m, 2H); 7.74 (d, J=9.6 Hz, 1H). $^{13}$C NMR (75 MHz, CDCl$_3$) δ ppm: 13.9, 14.0, 22.5, 29.1, 29.2, 29.3, 29.4, 31.6, 35.1, 35.4, 108.0, 120.5, 129.3, 135.8, 142.5, 146.9, 152.6, 156.6. IR ν cm$^{-1}$: 3335, 3215, 2955, 2855, 1620, 1500, 1465, 1340, 1235, 1135, 1080, 960, 930, 855, 830, 725. MS (ESI) m/z: 286 ([M+H]$^+$, 40).

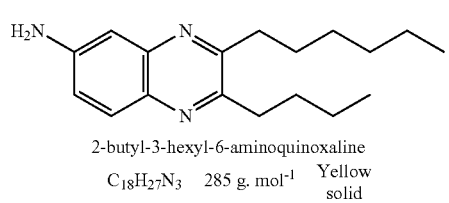

4de 2-butyl-3-hexyl-6-aminoquinoxaline

C$_{18}$H$_{27}$N$_3$    285 g. mol$^{-1}$    Yellow solid

Preparation method similar to the one used for the synthesis of compound 4ed.

Yield: 45% (128 mg). $^1$H NMR (300 MHz, CDCl$_3$) δ ppm: 0.92 (m, 6H); 1.25 (m, 8H); 1.40 (m, 2H); 1.72 (m, 2H); 2.92 (m, 4H); 4.06 (s, 2H); 7.06 (m, 2H); 7.77 (d, J=7.8 Hz, 1H). $^{13}$C NMR (75 MHz, CDCl$_3$) δ ppm: 13.9, 14.0, 22.5, 22.8, 29.0, 29.1, 29.4, 31.6, 35.1, 35.4, 108.0, 120.5, 129.2, 135.8, 142.5, 146.9, 152.5, 156.6. IR ν cm$^{-1}$: 3335, 3215, 2955, 2930, 2860, 1625, 1550, 1465, 1345, 1235, 1170, 1135, 1075, 960, 905, 855, 830, 730. MS (ESI) m/z: 286 ([M+H]$^+$, 100).

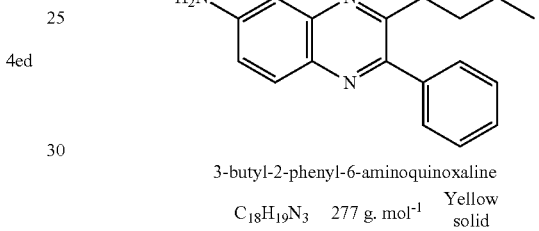

4cd 3-butyl-2-phenyl-6-aminoquinoxaline

C$_{18}$H$_{19}$N$_3$    277 g. mol$^{-1}$    Yellow solid

Preparation method similar to the one used for the synthesis of compound 4ed.

Yield: 32% (88 mg). $^1$H NMR (300 MHz, CDCl$_3$) δ ppm: 0.82 (t, J=7.2 Hz, 3H); 1.25 (m, 4H); 1.67 (t, J=7.8 Hz, 2H); 2.95 (t, J=7.8 Hz, 2H); 4.15 (s, 2H); 7.13 (m, 2H); 7.43-7.58 (m, 5H); 7.88 (d, J=8.7 Hz, 1H). $^{13}$C NMR (75 MHz, CDCL$_3$) δ ppm: 13.7, 22.6, 26.8, 31.3, 35.6, 107.5, 121.1, 128.0, 128.2, 128.3, 128.8, 129.6, 129.7, 130.1, 135.6, 139.5, 143.2, 147.8, 151.1, 156.2. IR ν cm$^{-1}$: 3335, 3215, 3060, 2955, 2925, 2855, 1620, 1580, 1560, 1495, 1460, 1445, 1420, 1345, 1240, 1135, 1075, 1010, 965, 910, 855, 830, 765, 730. MS (ESI) m/z: 278 ([M+H]$^+$, 100).

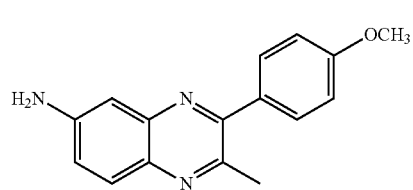

4bh 3-(4-methoxyphenyl)-2-methylquinoxalin-6-amine

C$_{16}$H$_{15}$N$_3$O    265.3 g. mol$^{-1}$    Yellow solid

Ten mL of tert-butyl lithium (1.6 M in pentane, 8 equiv.) were added dropwise at −78° C. to a solution of 4-bromoanisole (8 mmol, 4 equiv.) in anhydrous ether (5 mL), under inert nitrogen atmosphere. After 1 h of stirring at −78° C., a solution of compound 4ba (2 mmol, 1 equiv.) in THF (5 mL) was added dropwise. The reaction mixture was stirred at −78° C. for 2 h, then left to slowly warm up to room temperature.

After 24 h, the reaction medium was hydrolyzed by an aqueous saturated solution of NaHCO$_3$ and then extracted with ethyl acetate. The combined organic phases were then washed with an aqueous saturated NaCl solution, dried on Na$_2$SO$_4$, filtered and evaporated under reduced pressure.

The residue obtained was then taken up in chloroform and then 0.869 g of MnO$_2$ (10 mmol, 5 equiv.) were added. The reaction medium was heated under reflux for 2 h and then left at room temperature for 24 h.

The reaction medium was filtered on Celite and then concentrated under reduced pressure. Purification by silica gel chromatography in a DCM:MeOH mixture in a proportion of 98:2 yielded compound 4bh.

Yield: 34% (168.2 mg). $^1$H NMR (400 MHz, CDCl$_3$) δ ppm: 2.68 (s, 3H); 3.85 (s, 3H); 4.16 (brs, 2H); 7.00 (d, J=8.4 Hz, 2H); 7.09 (d, J=9.1 Hz, 1H); 7.14 (s, 1H); 7.58 (d, J=9.1 Hz, 2H); 7.79 (d, J=9.1 Hz, 1H). $^{13}$C NMR (100 MHz, CDCl$_3$) δ ppm: 23.8, 55.3, 108.3, 113.8 (2C), 121.4, 129.1, 130.3 (2C), 131.8, 135.9, 142.7, 147.3, 148.1, 154.4, 160.0. MS (ESI) m/z: 266.2 ([M+H]$^+$, 100). Purity (HPLC/UV 254 nm): 100%.

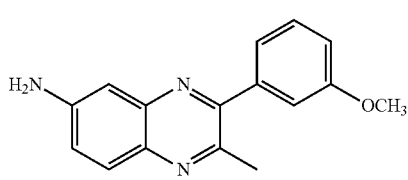

3-(3-methoxyphenyl)-2-methylquinoxalin-6-amine

C$_{16}$H$_{15}$N$_3$O    265.3 g. mol$^{-1}$    Yellow solid

Preparation method similar to the one used for the synthesis of compound 4bh.

Yield: 6% (59.7 mg). $^1$H NMR (300 MHz, CDCl$_3$) δ ppm: 2.70 (s, 3H); 3.88 (s, 3H); 3.90 (brs, 1H, NH) 4.20 (brs, 1H NH), 7.02 (d, J=8.1 Hz, 1H), 7.12-7.23 (m, 4H), 7.42 (td, J=8.1 and 1.5 Hz, 1H), 7.85 (dd, J=8.7 and 1.5 Hz, 1H). $^{13}$C NMR (75 MHz, CDCl$_3$) δ ppm: 23.7, 55.3, 108.3, 114.3, 114.5, 121.2, 121.7, 129.1, 129.4, 136.2, 140.7, 142.6, 147.4, 148.0, 154.6, 159.5. MS (ESI) m/z: 266.2 ([M+H]$^+$, 100). Purity (HPLC/UV 254 nm): 100%.

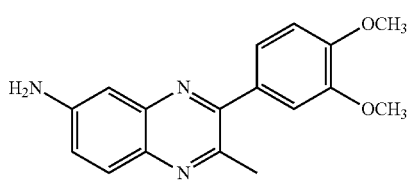

3-(3,4-dimethoxyphenyl)-2-methylquinoxalin-6-amine

C$_{17}$H$_{17}$N$_3$O$_2$    295.3 g. mol$^{-1}$    Yellow solid

Preparation method similar to the one used for the synthesis of compound 4bh.

Yield: 31% (310.0 mg). $^1$H NMR (400 MHz, CDCl$_3$) δ ppm: 2.74 (s, 3H), 3.94 (brs, 2H NH), 3.95 (s, 3H), 3.96 (s, 3H), 6.99 (d, J=8.8 Hz, 1H), 7.17 (d, J=8.8 Hz, 1H), 7.21 (s, 1H), 7.22 (d, J=6.0 Hz, 1H), 7.27 (s, 1H), 7.87 (d, J=8.8 Hz, 1H). $^{13}$C NMR (75 MHz, CDCl$_3$) δ ppm: 23.8, 56.0 (2C), 108.4, 110.9, 112.3, 121.5, 121.7, 129.2, 132.1, 136.1, 142.7, 147.3, 148.2, 148.9, 149.6, 154.5. MS (ESI) m/z: 296.2 ([M+H]$^+$, 100). Purity (HPLC/UV 254 nm): 92%.

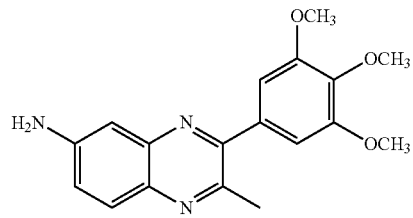

2-methyl-3-(3,4,5-trimethoxyphenyl)quinoxalin-6-amine

C$_{18}$H$_{19}$N$_3$O$_3$    323.3 g. mol$^{-1}$    Yellow solid

Preparation method similar to the one used for the synthesis of compound 4bh.

Yield: 21% (317.4 mg). $^1$H NMR (400 MHz, CDCl$_3$) δ ppm: 2.72 (s, 3H), 3.92 (s, 9H), 4.28 (brs, 2H NH), 6.84 (s, 2H), 7.17 (dd, J=8.8 and 2.4 Hz, 1H), 7.18 (s, 1H), δ 7.83 (d, J=8.1 Hz, 1H). $^{13}$C NMR (100 MHz, CDCl$_3$) δ ppm: 23.7, 56.1 (2C), 60.8, 106.2 (2C), 108.0, 121.7, 129.1, 134.9, 136.1, 138.5, 142.4, 147.5, 147.8, 153.1 (2C), 154.4. MS (ESI) m/z: 326.1 ([M+H]$^+$, 100). 348.2 ([M+Na]$^+$, 100). Purity (HPLC/UV 254 nm): 96%.

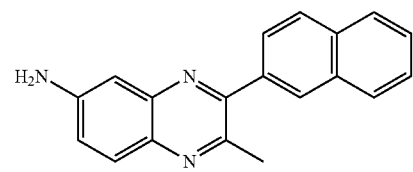

2-methyl-3-(naphthalen-2-yl)quinoxalin-6-amine

C$_{19}$H$_{15}$N$_3$    285.3 g. mol$^{-1}$    Yellow solid

Preparation method similar to the one used for the synthesis of compound 4bh.

Yield: 48% (531.8 mg). $^1$H NMR (400 MHz, CDCl$_3$) δ ppm: 2.74 (s, 3H), 4.14 (brs, 2H NH), 7.16 (dd, J=8.9 Hz and 2.5 Hz, 1H), 7.21 (d, J=2.5 Hz, 1H), 7.52-7.57 (m, 2H), 7.74 (dd, J=8.1 and 8 Hz, 1H), 7.86 (d, J=8.9 Hz, 1H), 7.91 (d, J=9.5 Hz, 1H), 7.92 d, J=9.5 Hz, 1H), 7.97 (d, J=8.9 Hz, 1H), 8.10 (s, 1H). $^{13}$C NMR (100 MHz, CDCl$_3$) δ ppm: 23.9, 108.4, 121.7, 126.4, 126.7 (2C), 127.7, 128.1, 128.4, 128.5, 129.3, 133.1, 133.2, 136.3, 136.9, 142.8, 147.4, 148.3, 154.8. MS (ESI) m/z: 286.2 ([M+H]$^+$, 100). Purity (HPLC/UV 254 nm): 88%.

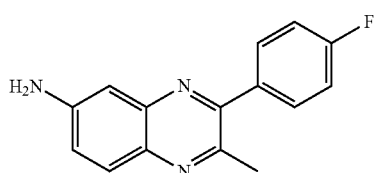

3-(4-fluorophenyl)-2-methylquinoxalin-6-amine

C$_{15}$H$_{12}$FN$_3$    253.2 g. mol$^{-1}$    Yellow solid

Preparation method similar to the one used for the synthesis of compound 4bh.

Yield: 35% (352.2 mg). $^1$H NMR (400 MHz, CDCl$_3$) δ ppm: 2.68 (s, 3H), 3.90 (brs, 2H NH), 7.16-7.21 (m, 4H), 7.61 (d, J=8.4 Hz, 1H), 7.63 (d, J=8.4 Hz, 1H), 7.85 (d, J=9.2 Hz, 1H). $^{13}$C NMR (100 MHz, CDCl$_3$) δ ppm: 23.7, 108.1, 115.5 (d, J=21.5 Hz), 122.0, 129.2, 130.9 (d, J=8.1 Hz), 135.3 (d, J=2.5 Hz), 136.2, 142.6, 147.5, 147.8, 153.6, 163.1 (d, J=250.4 Hz). MS (ESI) m/z: 254.2 ([M+H]$^+$, 100). Purity (HPLC/UV 254 nm): 92%.

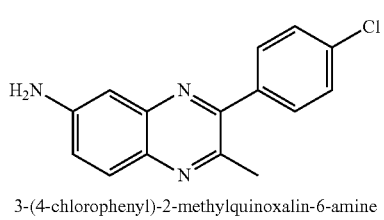

3-(4-chlorophenyl)-2-methylquinoxalin-6-amine

C$_{15}$H$_{12}$ClN$_3$   269.7 g. mol$^{-1}$   Yellow solid

Preparation method similar to the one used for the synthesis of compound 4bh.

Yield: 70% (1.1274 g). $^1$H NMR (300 MHz, CDCl$_3$) δ ppm: 2.67 (s, 3H); 3.85 (s, 3H); 4.16 (brs, 2H); 7.00 (d, J=8.4 Hz, 2H); 7.09 (d, J=9.1 Hz, 1H); 7.14 (s, 1H); 7.58 (d, J=7.9 Hz, 2H); 7.83 (d, J=9.1 Hz, 1H). $^{13}$C NMR (75 MHz, CDCl$_3$) δ ppm: 23.7, 108.2, 122.0, 128.7 (2C), 129.3, 130.4 (2C), 134.9, 136.4, 137.9, 142.7, 147.4, 147.8, 153.5. MS (ESI) m/z: 270.1 ($^{35}$Cl) ([M+H]$^+$, 100). 272.2 ($^{37}$Cl) ([M+H]$^+$, 40).

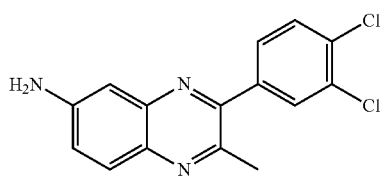

3-(3,4-dichlorophenyl)-2-methylquinoxalin-6-amine

C$_{15}$H$_{11}$Cl$_2$N$_3$   304.2 g. mol$^{-1}$   Yellow solid

Preparation method similar to the one used for the synthesis of compound 4bh.

Yield: 45% (813.9 mg). $^1$H NMR (300 MHz, CDCl$_3$) δ ppm: 2.68 (s, 3H), 4.17 (brs, 2H NH), 7.14 (d, J=2.0 Hz, 1H), 7.18 (dd, J=9.1 and 2.3 Hz, 1H), 7.47 (dd, J=8.4 and 2.0 Hz, 1H), 7.58 (d, J=8.4 Hz, 1H), 7.75 (d, J=2.0 Hz, 1H), 7.83 (d, J=8.9 Hz, 1H). $^{13}$C NMR (75 MHz, CDCl$_3$) δ ppm: 23.7, 108.1, 122.3, 128.3, 129.3, 130.4, 131.1, 132.8, 133.1, 136.5, 139.4, 142.7, 147.4, 147.6, 152.2. MS (ESI) m/z: 304.1 ($^{35}$Cl and $^{35}$Cl) ([M+H]$^+$, 100), 306.1 ($^{35}$Cl and $^{37}$Cl) ([M+H]$^+$, 55).

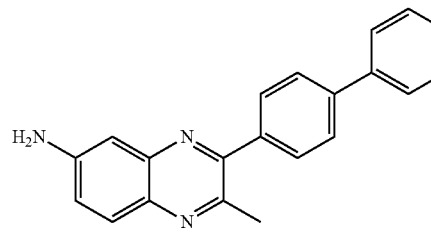

3-(biphenyl)-2-methylquinoxalin-6-amine

C$_{21}$H$_{17}$N$_3$   311.4 g. mol$^{-1}$   Brown solid

Preparation method similar to the one used for the synthesis of compound 4bh.

Yield: 30% (219.3 mg). $^1$H NMR (300 MHz, CDCl$_3$) δ ppm: 2.77 (s, 3H), 4.23 (brs, 2H NH), 7.12 (dd, J=8.7 and 1.8, 1H), 7.18 (d, J=1.8, 1H), 7.38 (t, J=7.5, 1H), 7.47 (t, J=7.5, 2H), 7.66 (d, J=7.5, 2H), 7.71 (m, 4H), 7.84 (d, J=8.7, 1H). $^{13}$C NMR (75 MHz, CDCl$_3$) δ ppm: 23.7, 108.1, 121.7, 127.0 (4C), 127.5, 128.8 (2C), 129.0, 129.3 (2C), 136.0, 138.2, 140.4, 141.4, 142.7, 147.4, 147.9, 154.3. MS (ESI) m/z: 312.2 ([M+H]%, 100).

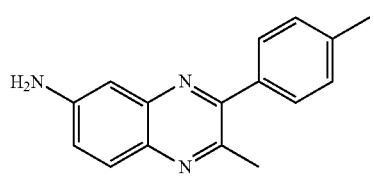

2-methyl-3-ρ-tolylquinoxalin-6-amine

C$_{16}$H$_{15}$N$_3$   249.3 g. mol$^{-1}$   Yellow solid

Preparation method similar to the one used for the synthesis of compound 4bh.

Yield: 56% (851.7 mg). $^1$H NMR (300 MHz, CDCl$_3$) δ ppm: 2.45 (s, 3H), 2.72 (s, 3H), 4.28 (brs, 2H NH), 7.12 (dd, J=8.9 and 2.1 Hz, 1H), 7.20 (d, J=2.1 Hz, 1H), 7.32 (d, J=7.6 Hz, 2H), 7.56 (d, J=7.6 Hz, 2H), 7.84 (d, J=8.9 Hz, 1H). $^{13}$C NMR (75 MHz, CDCl$_3$) δ ppm: 21.2, 23.7, 108.0, 121.5, 128.7 (2C), 128.9 (3C), 135.9, 136.4, 138.5, 142.6, 147.3, 147.9, 154.6. MS (ESI) m/z: 250.2 ([M+H]%, 100).

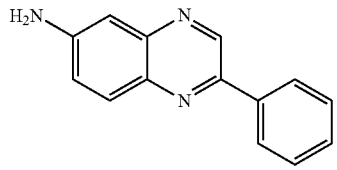

2-phenylquinoxalin-6-amine

C$_{14}$H$_{11}$N$_3$   221.2 g. mol-1   Yellow solid 245 mg of Pd/C (10% m/m) were added to a solution of compound 3ca (9.8 mmol, 1 equiv.) in ethanol (150 mL).

The reaction was stirred at 60° C. and placed under hydrogen for 24 h. After cooling, the reaction was filtered on Celite and then rinsed with ethanol. The filtrate was then concentrated under reduced pressure.

Purification by silica gel chromatography in a DCM:MeOH mixture in a proportion of 98:2 yielded compound 4ca (major compound) and compound 4ac (minor compound: 4% (79.5 mg)).

Yield: 21% (453.3 mg). $^1$H NMR (400 MHz, CDCl$_3$) δ ppm: 3.99 (brs, 2H NH), 7.17 (brs, 1H), 7.18 (dd, J=8.9 and 2.6 Hz, 1H), 7.45 (tt, J=7.4 and 1.6 Hz, 1H), 7.52 (td, J=7.4 and 1.6 Hz, 2H), 7.9 (d, J=8.9 Hz, 1H), 8.11 (dd, J=7.3 and 1.6 Hz, 2H), 9.15 (s, 1H). $^{13}$C NMR (100 MHz, CDCl$_3$) δ ppm: 107.8, 122.2, 126.8 (2C), 128.9 (2C), 129.2, 130.5, 137.1 (2C), 143.2 (2C), 147.7, 148.1. MS (ESI) m/z: 222.2 ([M+H]$^+$, 100). Purity (HPLC/UV 254 nm): 100%.

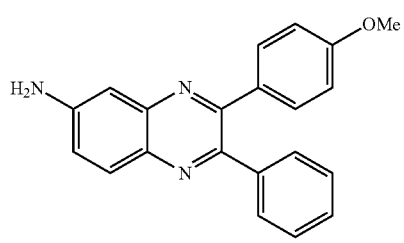

4ch 3-(4-methoxyphenyl)-2-phenylquinoxalin-6-amine

C$_{21}$H$_{17}$N$_3$O   327.4 g. mol$^{-1}$   Yellow solid

Preparation method similar to the one used for the synthesis of compound 4bh but from compound 4ca.

Yield: 2% (8.3 mg HPLC prep). $^1$H NMR (300 MHz, CDCl$_3$) δ ppm: 3.63 (brs, 2H NH), 3.81 (s, 3H), 6.83 (d, J=8.8 Hz, 2H), 7.16 (dd, J=8.8 and 2.1 Hz, 1H), 7.22 (d, J=2.2 Hz, 1H), 7.32 (m, 3H), 7.44 (d, J=8.8 Hz, 2H), 7.46-7.49 (m, 2H), 7.94 (d, J=8.9 Hz, 1H). $^{13}$C NMR (75 MHz, CDCl$_3$) δ ppm: 55.3, 107.9, 113.6 (2C), 121.7, 128.1, 128.2 (2C), 129.7 (2C), 130.2, 131.3 (2C), 131.7, 136.1, 139.7, 143.0, 148.0, 149.6, 152.9, 160.0. MS (ESI) m/z: 328.2 ([M+H]$^+$, 100).

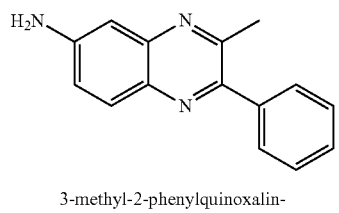

4cb 3-methyl-2-phenylquinoxalin-6-amine

C$_{15}$H$_{13}$N$_3$   235.3 g. mol-1   Yellow solid 80 mg of Pd/C (10% m/m) were added to a solution of compound 3cb and 3bc (3 mmol) in ethanol (100 mL). The reaction was stirred at 60° C. and placed under hydrogen for 4 h. After cooling, the reaction was filtered on Celite and rinsed with ethanol and the filtrate was concentrated under reduced pressure Purification by silica gel chromatography in a DCM:MeOH mixture in a proportion of 98:2 yielded compound 4cb (minor compound) and compound 4bc (major compound). (NMR ratio (1:3)).

Yield: 33% on NMR (3 mg isolated). $^1$H NMR (300 MHz, CDCl$_3$) δ ppm: 2.70 (s, 3H), 4.18 (brs, 2H NH), 7.12 (s, 1H), 7.13 (dd, J=2.5 and 8.2 Hz, 1H), 7.45-7.43 (m, 3H), 7.62 (dd, J=7.6 and 2.0 Hz, 2H), 7.89 (dd, J=8.2 and 1.1 Hz, 1H). $^{13}$C NMR (75 MHz, CDCl$_3$) δ ppm: 24.1, 107.2, 121.1, 128.3 (3C), 128.9 (2C), 130.1, 135.8, 139.3, 143.0, 147.9, 150.8, 152.3.

I.4. Synthesis of Compounds 5

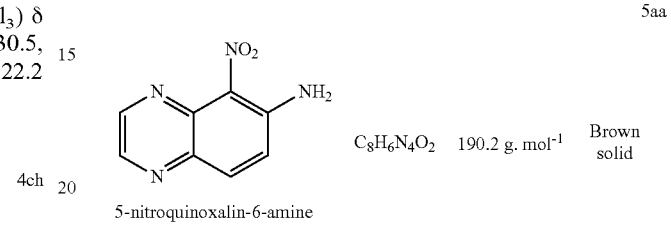

5aa 5-nitroquinoxalin-6-amine

C$_8$H$_6$N$_4$O$_2$   190.2 g. mol$^{-1}$   Brown solid

KNO$_3$ (1.25 equiv.) was slowly added to a solution of compound 4aa (1 equiv.) in sulfuric acid (20 mL, d=1.83) at a temperature below −10° C. The solution was stirred at this temperature for 1 h and then placed in an ice water bath and left overnight. The reaction mixture was poured over a water-ice mixture, neutralized by addition of NH$_4$OH (d=0.9) and then extracted with AcOEt. The organic phase was washed with a solution of NaCl, dried on MgSO$_4$ and then concentrated under reduced pressure. Silica column flash chromatography purification yielded desired compound 5aa.

Yield: 30.5% (over 2 steps, from compound 3aa without intermediate purification). $^1$H NMR (200 MHz, DMSO) δ ppm: 7.31 (s, 2H), 7.42 (d, J=9.4 Hz, 1H), 7.90 (d, J=9.4 Hz, 1H), 7.63 (d, J=2.2 Hz, 1H), 8.76 (d, J=2.0 Hz, 1H). $^{13}$C NMR (50 MHz, DMSO) δ ppm: 145.46, 144.29, 141.18, 138.06, 135.33, 133.12, 125.72, 123.82.

IR ν cm$^{-1}$: 3383, 3293, 3200, 3086, 2924, 2851, 1629, 1560, 1544, 1506, 1479, 1463, 1425, 1364, 1342, 1283, 1265, 1214, 1150, 1118, 1053, 1017, 892, 867, 837, 804, 793, 751. MS (ESI): 191 ([M+H]$^+$, 20).

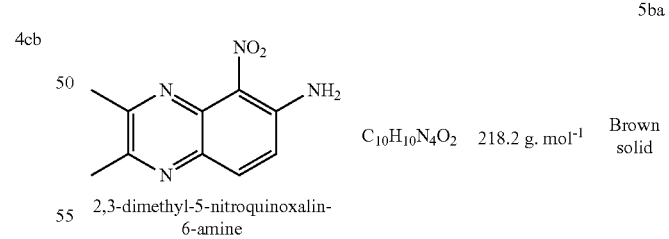

5ba 2,3-dimethyl-5-nitroquinoxalin-6-amine

C$_{10}$H$_{10}$N$_4$O$_2$   218.2 g. mol$^{-1}$   Brown solid

Preparation method similar to the one used for the synthesis of compound 5aa.

Yield: 23.3%. $^1$H NMR (200 MHz, DMSO) δ ppm: 2.55 (s, 3H), 2.56 (s, 3H), 6.96 (s, 2H), 7.27 (d, J=9.2 Hz, 1H), 7.76 (d, J=9.4 Hz, 1H). $^{13}$C NMR (50 MHz, DMSO) δ ppm: 154.11, 149.34, 142.99, 135.61, 133.00, 132.05, 126.28, 121.75, 22.68, 21.80. IR ν cm$^{-1}$: 3459, 3336, 3200, 2920, 1630, 1548, 1508, 1481, 1457, 1427, 1381, 1361, 1350, 1285, 1255, 1211, 1168, 1044, 992, 954, 835, 797, 744, 687, 674. MS (ESI) m/z: 219 ([M+H]$^+$, 15).

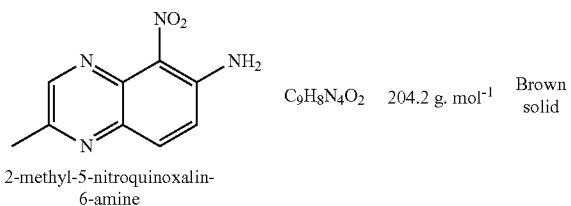

2-methyl-5-nitroquinoxalin-6-amine

C$_9$H$_8$N$_4$O$_2$   204.2 g. mol$^{-1}$   Brown solid

Preparation method similar to the one used for the synthesis of compound 5aa.

Yield: 27.9%. $^1$H NMR (200 MHz, DMSO) δ ppm: 2.59 (s, 3H), 7.16 (s, 2H), 7.38 (d, J=9.4 Hz, 1H), 7.82 (d, J=9.4 Hz, 1H), 8.69 (s, 1H). $^{13}$C NMR (50 MHz, DMSO) δ ppm: 154.57, 149.76, 145.98, 143.45, 134.31, 132.53, 125.96, 123.44, 21.11. IR ν cm$^{-1}$: 3450, 3328, 3178, 1635, 1557, 1544, 1512, 1476, 1420, 1376, 1341, 1269, 1218, 1200, 1148, 1035, 1014, 949, 909, 833, 817, 799, 768. MS (ESI) m/z: 227 ([M+Na]$^+$, 75).

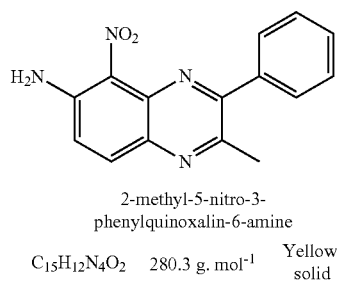

2-methyl-5-nitro-3-phenylquinoxalin-6-amine

C$_{15}$H$_{12}$N$_4$O$_2$   280.3 g. mol$^{-1}$   Yellow solid

Preparation method similar to the one used for the synthesis of compound 5aa.

Yield: 20% (121.2 mg). $^1$H NMR (300 MHz, CDCl$_3$) δ ppm: 2.74 (s, 3H), 6.08 (brs, 2H NH), 7.11 (d, J=9.5 Hz, 1H), 7.42-7.52 (m, 3H), 7.75 (d, J=6.6 Hz, 2H), 7.83 (d, J=9.2 Hz, 1H). $^{13}$C NMR (75 MHz, CDCl$_3$) δ ppm: 23.7, 122.5, 126.5, 128.4 (2C), 129.3, 129.4 (2C), 133.8, 134.7, 136.9, 138.3, 144.2, 148.9, 154.8. MS (ESI) m/z: 281.1 ([M+H]$^+$, 50), 303.1 ([M+Na]$^+$, 85), 583.2 ([2M+Na]$^+$, 100).

I.5. Synthesis of Compounds 6

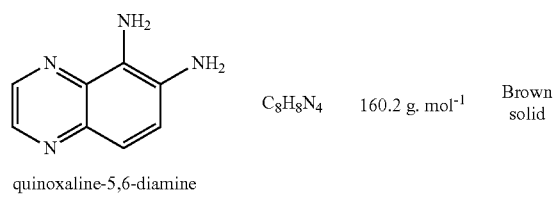

quinoxaline-5,6-diamine

C$_8$H$_8$N$_4$   160.2 g. mol$^{-1}$   Brown solid

SnCl$_2$ (5 equiv.) is added to a solution of compound 5aa (1 equiv.) in absolute EtOH (40 mL). The reaction mixture is refluxed for 42 to 68 h under N$_2$, then basified (pH=8) by addition of NaHCO$_3$. After filtering the filtrate on Celite and adding water, it was extracted with AcOEt. The organic phase was washed with water, dried on MgSO$_4$ and then concentrated under reduced pressure. Silica gel column flash chromatography purification yielded desired compound 6aa.

Yield: 75.0%. Starting with 4-nitro-phenylene-1,2 diamine without intermediate purification, the yield was 30.0% (over 3 steps).

$^1$H NMR (200 MHz, DMSO) δ ppm: 5.20 (s, 4H), 7.17 d, J=8.8 Hz, 1H), 7.25 (d, J=8.8 Hz, 1H), 8.49 (d, J=1.8 Hz, 1H), 8.57 (d, J=1.8 Hz, 1H). $^{13}$C NMR (50 MHz, DMSO) δ ppm: 141.83, 140.06, 136.88, 132.97, 132.42, 125.95, 121.79, 116.36. IR ν cm$^{-1}$: 3379, 3306, 3225, 1610, 1570, 1542, 1505, 1483, 1420, 1367, 1322, 1269, 1233, 1174, 1120, 1073, 1035, 908, 856, 827, 807, 779, 667. MS (ESI) m/z: 161 ([M+H]$^+$, 100).

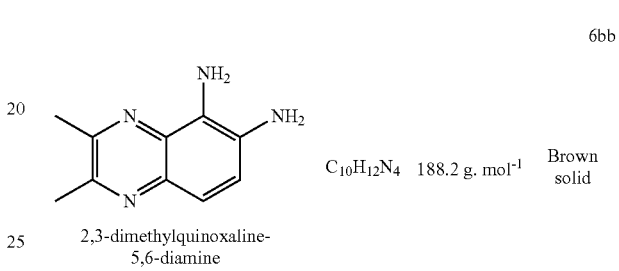

2,3-dimethylquinoxaline-5,6-diamine

C$_{10}$H$_{12}$N$_4$   188.2 g. mol$^{-1}$   Brown solid

Preparation method similar to the one used for the synthesis of compound 6aa.

Yield: 7.9% (over 2 steps, starting from compound 4bb without intermediate purification). $^1$H NMR (200 MHz, CDCl$_3$) δ ppm: 2.64 (s, 3H), 2.66 (s, 3H), 3.96 (s, 4H), 7.10 (d, J=8.8 Hz, 7.32 (d, J=8.8 Hz, 1H). $^{13}$C NMR (50 MHz, CDCl$_3$) δ ppm: 150.85, 149.64, 131.74, 127.44, 118.16, 23.08, 22.71. IR ν cm$^{-1}$: 3440, 3355, 3177, 2917, 1651, 1615, 1571, 1501, 1477, 1441, 1408, 1377, 1344, 1291, 1257, 1202, 1143, 999, 935, 820, 785, 733. MS (ESI) m/z: 189 ([M+H]$^+$, 100).

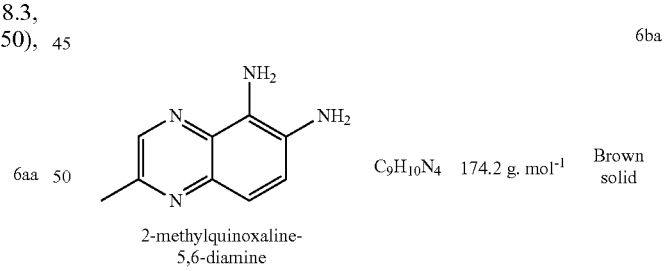

2-methylquinoxaline-5,6-diamine

C$_9$H$_{10}$N$_4$   174.2 g. mol$^{-1}$   Brown solid

Preparation method similar to the one used for the synthesis of compound 6aa.

Yield: 42.6%. $^1$H NMR (200 MHz, DMSO) δ ppm: 2.56 (s, 3H), 5.12 (s, 4H), 7.07 (d, J=8.6 Hz, 1H), 7.19 (d, J=8.8 Hz, 1H), 8.50 (s, 1H). $^{13}$C NMR (50 MHz, DMSO) δ ppm: 148.06, 142.31, 135.86, 131.86, 130.56, 126.36, 121.47, 115.29, 21.38. IR ν cm$^{-1}$: 3380, 3280, 3218, 2918, 2852, 1671, 1613, 1571, 1497, 1478, 1420, 1355, 1309, 1296, 1267, 1238, 1172, 1115, 1066, 1014, 953, 903, 816, 784, 708, 683. MS (ESI): 175 ([M+H]$^+$, 100).

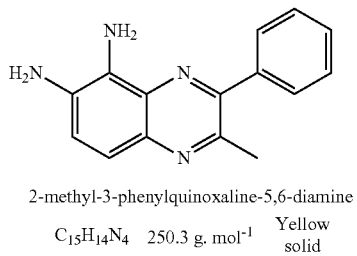

2-methyl-3-phenylquinoxaline-5,6-diamine $C_{15}H_{14}N_4$  250.3 g. mol$^{-1}$  Yellow solid Preparation method similar to the one used for the synthesis of compound 6aa.

Yield: 90% (10 mg). $^1$H NMR (300 MHz, CDCl$_3$) δ ppm: 2.73 (s, 3H), 3.78-4.30 (2 brs, 4H), 7.23 (d, J=8.6 Hz, 1H), 7.43 (d, J=8.6 Hz, 1H), 7.48-7.55 (m, 3H), 7.69 (dd, J=8.1 and 1.9 Hz, 2H). $^{13}$C NMR (75 MHz, CDCl$_3$) δ ppm: 24.0, 118.1, 122.1, 127.9, 128.3 (2C), 128.7, 129.2 (2C), 132.0, 132.4, 136.7, 139.6, 148.6, 152.1. MS (ESI) m/z: 251.2 ([M+H]%, 80).

I.6. Synthesis of Compounds 7

7aa

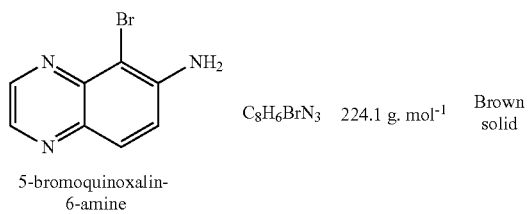

5-bromoquinoxalin-6-amine $C_8H_6BrN_3$  224.1 g. mol$^{-1}$  Brown solid

A solution of bromine (14.4 mmol, 0.74 mL) in 10 mL of glacial acetic acid was slowly added to a solution of compound 4aa (14.2) mmol) in acetic acid (15 mL) at a temperature close to 15° C. A reddish orange solid appeared. The reaction mixture was stirred for 1 h, hydrolyzed and then basified with a 1 N solution of NaOH. The reaction mixture was then extracted with ethyl acetate (200 mL×3), dried on Na$_2$SO$_4$ and then concentrated under reduced pressure to give 2.9918 g of a brown solid.

Yield: 94.0%. $^1$H NMR (400 MHz, CDCl$_3$) δ ppm: 4.80 (s, 2H), 7.24 (d, J=9.2 Hz, 1H), 7.81 (d, J=9.2 Hz, 1H), 8.56 (d, J=1.6 Hz, 1H), 8.76 (d, J=1.6 Hz, 1H). $^{13}$C NMR (50 MHz, CDCl$_3$) δ ppm: 145.91, 145.11, 142.08, 141.04, 138.56, 129.30, 121.27, 102.66. IR ν cm$^{-1}$: 3458, 3305, 3185, 3049, 1619, 1541, 1495, 1460, 1422, 1373, 1326, 1270, 1218, 1181, 1142, 1044, 974, 957, 861, 829, 788. MS (ESI) m/z: 224 ([M+H]$^+$, 80), 226 ([M+H]%, 75).

7bc

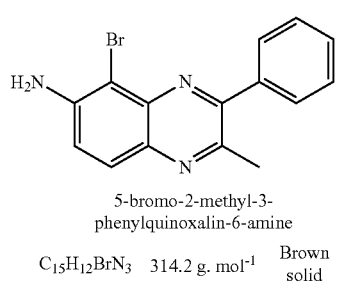

5-bromo-2-methyl-3-phenylquinoxalin-6-amine $C_{15}H_{12}BrN_3$  314.2 g. mol$^{-1}$  Brown solid Preparation method similar to the one used for the synthesis of compound 7aa.

Yield: 90% (385.2 mg). $^1$H NMR (300 MHz, CDCl$_3$) δ ppm: 2.73 (s, 3H), 4.83 (brs, 2H NH), 7.13 (d, J=8.7 Hz, 1H), 7.46 (m, 3H), 7.73 (m, 3H). $^{13}$C NMR (75 MHz, CDCl$_3$) δ ppm: 23.3, 102.9, 120.9, 127.4, 128.2 (2C), 128.8, 129.3 (2C), 135.7, 138.6, 140.0, 145.3, 147.7, 154.5. MS (ESI) m/z: 314 ($^{79}$Br) and 316 ($^{81}$Br) ([M+H]$^+$, 70), 336 ($^{79}$Br) and 338 ($^{81}$Br) ([M+Na]$^+$, 80), 651 ([2M+Na]$^+$, 100).

I.7. Synthesis of Compounds 8

8bc

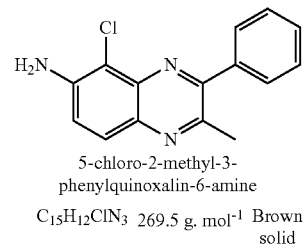

5-chloro-2-methyl-3-phenylquinoxalin-6-amine $C_{15}H_{12}ClN_3$  269.5 g. mol$^{-1}$  Brown solid 118 mg of N-chlorosuccinimide (1.07 mmol, 1.2 equiv.) were added to a solution of compound 4bc (208 mg, 0.89 mmol, 1 equiv.) in anhydrous dichloromethane at room temperature. The reaction medium was then refluxed with CH$_2$Cl$_2$ overnight. After cooling, the reaction mixture was hydrolyzed by a 5% NaOH solution and then extracted three times with CH$_2$Cl$_2$. The organic phases were collected, washed with a saturated NaCl solution, dried on Na$_2$SO$_4$ and then concentrated under reduced pressure to give 279 mg of the desired product.

Yield: 99% (279 mg). $^1$H NMR (400 MHz, CDCl$_3$) δ ppm: 2.73 (s, 3H), 4.60 (brs, 2H NH), 7.19 (d, J=9.2 Hz, 1H), 7.48 (m, 3H), 7.71 (dd, J=8.6 and 1.3 Hz, 2H), 7.45 (d, J=9.2 Hz, 1H). $^{13}$C NMR (100 MHz, CDCl$_3$) δ ppm: 23.7, 111.1, 120.8, 127.3, 128.3 (2C), 128.9, 129.3 (2C), 136.4, 139.0, 139.1, 143.6, 148.3, 154.6.

I.8. Synthesis of Compounds 9

9bc 2-methyl-3-phenyl-N-(prop-2-ynyl)quinoxalin-6-amine $C_{18}H_{15}N_3$  273.4 g. mol$^{-1}$  Yellow solid 118 mg of K$_2$CO$_3$ (0.85 mmol, 1 equiv.), 141 mg of KI (0.85 mmol, 1 equiv.) and 0.19 mL of propargyl bromide (1.7 mmol, 2 equiv.) were added to a solution of compound 4bc (200 mg, 0.85 mmol, 1 equiv.) in anhydrous dimethylformamide. The reaction mixture was then heated to 100° C. for 24 h. After cooling, the reaction medium was hydrolyzed by a saturated K$_2$CO$_3$ solution, and then extracted 3 times with ethyl acetate. The organic phases were collected, washed with a saturated NaCl solution, dried on Na$_2$SO$_4$ and then concentrated under reduced pressure. Purification by silica gel chromatography in a cyclohexane:ethyl acetate mixture in proportions of 7:3 and then 6:4 yielded compound 9bc (major compound, 90.1 mg) and the dialkylated compound (minor compound, 14 mg, not described).

Yield: 40% (90.1 mg). $^1$H NMR (400 MHz, CDCl$_3$) δ ppm: 2.23 (t, J=2.4 Hz, 1H), 2.67 (s, 3H), 4.01 (brs, 2H), 4.56 (brs, 1H, NH), 7.09 (dd, J=2.6 and 8.8 Hz, 1H), 7.12 (d, J=2.6 Hz, 1H), 7.43-7.50 (m, 3H), 7.61 (dd, J=1.6 and 8.8 Hz, 2H), 7.81 (d, J=8.8 Hz, 1H). $^{13}$C NMR (100 MHz, CDCl$_3$) δ ppm: 23.6, 33.3, 71.7, 79.9, 105.2, 121.6, 128.3 (2C), 128.6, 128.8 (2C), 128.9, 136.3, 139.4, 142.8, 147.3, 147.9, 154.6. MS (ESI) m/z: 274.2 ([M+H]$^+$, 100). Purity (HPLC/UV 260 nm): 100%.

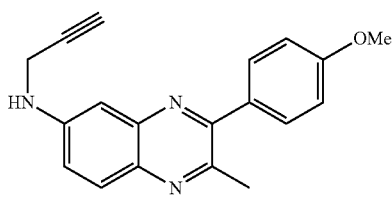

9bh 3-(4-methoxyphenyl)-2-methyl-N-(prop-2-ynyl)quinoxalin-6-amine

C$_{19}$H$_{17}$N$_3$O   303.4 g. mol$^{-1}$   Yellow solid

Preparation method similar to the one used for the synthesis of compound 9bc.

Yield: 71% (280.0 mg). MS (ESI) m/z: 304.3 ([M+H]$^+$, 100). Purity (HPLC/UV 260 nm): 100%.

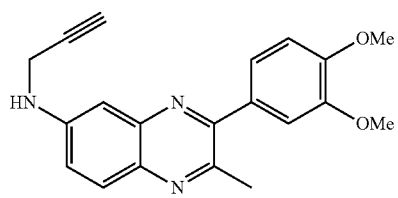

9bj 3-(3,4-dimethoxyphenyl)-2-methyl-N-(prop-2-ynyl)quinoxalin-6-amine

C$_{20}$H$_{19}$N$_3$O$_2$   333.4 g. mol$^{-1}$   Yellow solid

Preparation method similar to the one used for the synthesis of compound 9bc.

Yield: 47% (29.6 mg). MS (ESI) m/z: 334.2 ([M+H]$^+$, 100). Purity (HPLC/UV 260 nm): 84%.

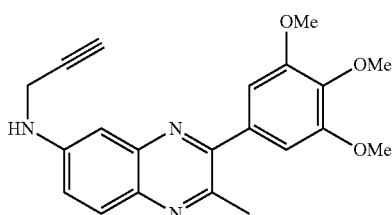

9bk 2-methyl-N-(prop-2-ynyl)-3-(3,4,5-trimethoxyphenyl)quinoxalin-6-amine

C$_{21}$H$_{21}$N$_3$O$_3$   363.4 g. mol$^{-1}$   Yellow solid

Preparation method similar to the one used for the synthesis of compound 9bc.

Yield: 42% (118.7 mg). MS (ESI) m/z: 364.2 ([M+H]$^+$, 60) and 749.3 [2M+Na]$^+$, 100). Purity (HPLC/UV 260 nm): 92%.

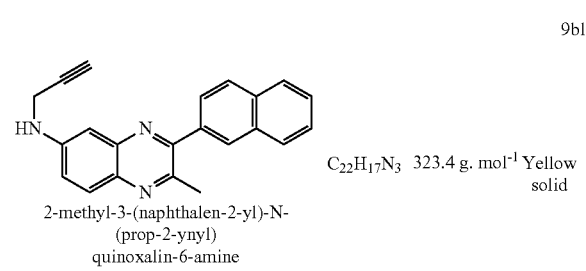 [SMILES: "C22H17N3" ; C#CCNc1ccc2nc(C)c(-c3ccc4ccccc4c3)nc2c1]

9bl 2-methyl-3-(naphthalen-2-yl)-N-(prop-2-ynyl)quinoxalin-6-amine

C$_{22}$H$_{17}$N$_3$   323.4 g. mol$^{-1}$   Yellow solid

Preparation method similar to the one used for the synthesis of compound 9bc.

Yield: 28% (80.5 mg). MS (ESI) m/z: 324.2 ([M+H]$^+$, 100). Purity (HPLC/UV 220 nm): 90%.

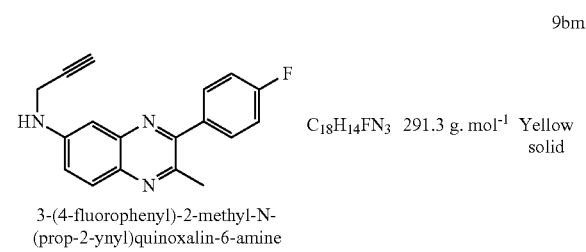 [SMILES: "C18H14FN3" ; C#CCNc1ccc2nc(C)c(-c3ccc(F)cc3)nc2c1]

9bm 3-(4-fluorophenyl)-2-methyl-N-(prop-2-ynyl)quinoxalin-6-amine

C$_{18}$H$_{14}$FN$_3$   291.3 g. mol$^{-1}$   Yellow solid

Preparation method similar to the one used for the synthesis of compound 9bc.

Yield: 28% (74 mg). $^1$H NMR (300 MHz, CDCl$_3$) δ ppm: 2.26 (t, J=2.4 Hz, 1H), 2.69 (s, 3H), 4.06 (brs, 2H), 4.38 (brs, 1H, NH), 7.12-7.15 (m, 2H), 7.20 (t, J=8.8 Hz, 2H), 7.61-7.65 (m, 2H), 7.84 (d, J=8.8 Hz, 1H). $^{13}$C NMR (100 MHz, CDCl$_3$) δ ppm: 23.8, 33.5, 71.9, 79.9, 105.3, 115.4, 115.6, 121.8, 129.1, 130.8, 130.9, 136.5, 139.4, 142.9, 147.4, 147.9, 153.7, 164.3. MS (ESI) m/z: 292.2 ([M+H]$^+$, 100). Purity (HPLC/UV 260 nm): 94%.

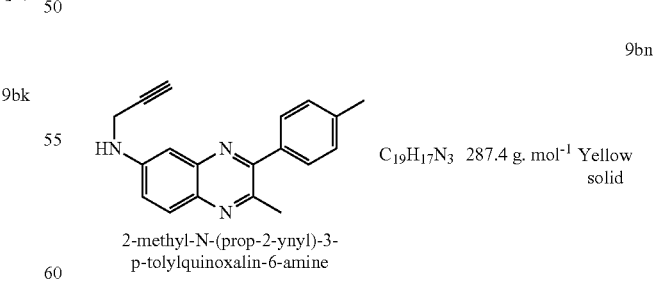

9bn 2-methyl-N-(prop-2-ynyl)-3-p-tolylquinoxalin-6-amine

C$_{19}$H$_{17}$N$_3$   287.4 g. mol$^{-1}$   Yellow solid

Preparation method similar to the one used for the synthesis of compound 9bc.

Yield: 40% (207.0 mg). MS (ESI) m/z: 288.2 ([M+H]$^+$, 100).

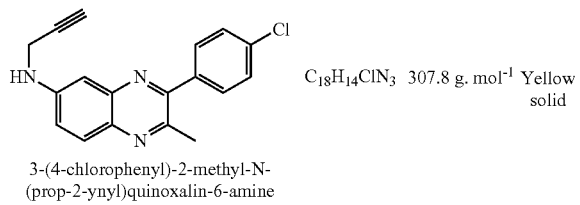

9bo $C_{18}H_{14}ClN_3$ 307.8 g. mol$^{-1}$ Yellow solid 3-(4-chlorophenyl)-2-methyl-N-(prop-2-ynyl)quinoxalin-6-amine Preparation method similar to the one used for the synthesis of compound 9bc.

Yield: 34% (160 mg). MS (ESI) m/z: 308.2 ([M+H]$^+$, 25) and 310.1 ([M+H]$^+$, 7.5). Purity (HPLC/UV 274 nm): 95%.

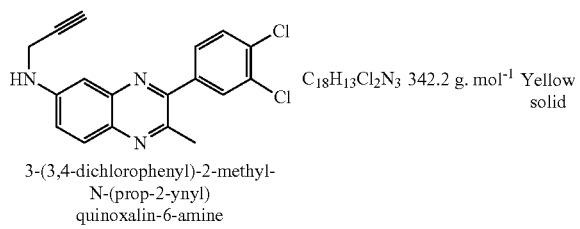

9bp $C_{18}H_{13}Cl_2N_3$ 342.2 g. mol$^{-1}$ Yellow solid 3-(3,4-dichlorophenyl)-2-methyl-N-(prop-2-ynyl)quinoxalin-6-amine Preparation method similar to the one used for the synthesis of compound 9bc.

Yield: 50% (196.0 mg). MS (ESI) m/z: 242.1 ([M+H]$^+$, 100) and 344.1 ([M+H]$^+$, 50). Purity (HPLC/UV 264 nm): 94%.

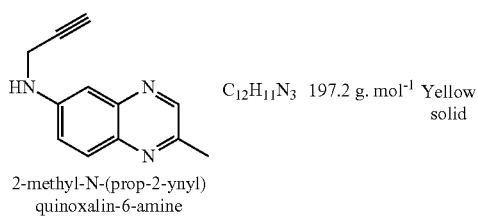

9ba $C_{12}H_{11}N_3$ 197.2 g. mol$^{-1}$ Yellow solid 2-methyl-N-(prop-2-ynyl)quinoxalin-6-amine Preparation method similar to the one used for the synthesis of compound 9bc.

Yield: 41% (2.570 g). MS (ESI) m/z: 198.2 ([M+H]$^+$, 100). Purity (HPLC/UV 220 nm): 94%.

II. Biological Evaluation

The aminoquinoxalines were then evaluated for their neuroprotective and neural differentiating (or neuritogenic) properties.

II.1 Effect of the Compounds on Dopaminergic Neuron Neuroprotection and Differentiation in Primary Culture in a Spontaneous Degeneration Model.

II. 1.1 Structure-Activity Relationship and Determination of the Effective Concentration (EC50)

Quinoxaline derivatives were tested on a dopaminergic neuron spontaneous degeneration model in culture according to the protocol described in the article by F. Schmidt et al. PLoS ONE 2009, 4(7) e2615 ("Chemicals Possessing a Neurotrophin-Like Activity on Dopaminergic Neurons in Primary Culture"). This model consists of culturing rat embryo ventral midbrain. This part of the brain in culture contains a proportion of dopaminergic neurons of 5% of the total neurons; the other neurons are mainly GABAergic. These cultures are also composed of glial cells, i.e., astrocytes, oligodendrocytes and microglia. These cultures are characterized by progressive neuron death. The neuroprotective effect of compounds according to the invention was evaluated by counting dopaminergic neurons (TH$^+$) labeled by tyrosine hydroxylase immunohistochemistry (TH) after 8 days of culture. Thus, for example, compounds 4aa, 4ba, 4ad, 4bd, 4bc and 4ed were evaluated at 1 nM, 10 nM, 100 nM and 1 μM and compared to the activity of dibutyryl-cyclic AMP (dbcAMP) at 200 μm.

TABLE 1

Activity of certain aminoquinoxaline derivatives at 100 nM on the survival of fetal dopaminergic neurons in culture.

| Compound (100 nM) | R$_1$ | R$_2$ | TH+ neurons in % of control ± SEM[a] | Diff in % of control ± SEM |
|---|---|---|---|---|
| control | | | 100 +/− 1.9% | 100 +/− 5.6% |
| dbcAMP | | | 149.9 +/− 3.6% | 333 +/− 8.7% |
| 4ad | n-Bu | H | 101.0 +/− 4.1% | 118.4 +/− 9.0% |
| 4bd | n-Bu | CH$_3$ | 120.6 +/− 5.4% | 102.5 +/− 4.6% |
| 4bc | Ph | CH$_3$ | 140.4 +/− 4.1% | 142.1 +/− 3.3% |
| 4ed | n-Bu | n-Hex | 114.6 +/− 5.9% | 104.3 +/− 9.5% |

[a]Standard error of the mean. The data are expressed in percentage of the negative control value (mean ± SEM).

The results show a particularly extensive activity of compound 4bc with a survival percentage nearly equal to the one induced by dbcAMP. A particularly interesting activity of compounds substituted in position 2 of the quinoxaline ring by an aromatic motif is also observed.

Quinoxaline derivatives have also been tested on a dopaminergic neuron spontaneous degeneration model in culture according to a protocol slightly different from the one previously described. This second protocol is described in the article by Mourlevat, P. P. Michel et al. *Molecular Pharmacology* 2003, 64:578-586 ("Prevention of Dopaminergic Neuronal Death by Cyclic AMP in Mixed Neuronal/Glial Mesencephalic Cultures Requires the Repression of Presumptive Astrocytes"). The neuroprotective effect of compounds according to the invention was evaluated by counting dopaminergic neurons (TH$^+$) labeled by tyrosine hydroxylase (TH) immunohistochemistry after 10 days of culture. Compounds according to the invention were evaluated at 50 μM except compound 4bc which was assessed at 100 μM. They were compared to the activity of dibutyryl-cyclic AMP (dbcAMP) at 1 mM.

TABLE 2

Activity of certain aminoquinoxaline derivatives at 50 or 100 μM on the survival of fetal dopaminergic neurons in culture.

[Structure: quinoxaline with $R_0HN$ at position 7, X at position 8, and R groups at positions 2 and 3]

| Compound (50 μM) | $R_1$ | $R_2$ | $R_0$ | X | TH+ neurons in % of control ± Std. Err.[a] |
|---|---|---|---|---|---|
| control | | | | | 100 ± 4% |
| dbcAMP | | | | | 241 ± 9% |
| 4bc* | Ph | $CH_3$ | H | H | 139 ± 11% |
| 4ch | 4-OMe—Ph | Ph | H | H | 130 ± 10% |
| 4ac | Ph | H | H | H | 189 ± 11% |
| 9bc | Ph | $CH_3$ | $CH_2C≡CH$ | H | 174 ± 15% |
| 9bm | 4-F—Ph | $CH_3$ | $CH_2C≡CH$ | H | 166 ± 15% |
| 7bc | Ph | $CH_3$ | H | Br | 153 ± 12% |
| 8bc | Ph | $CH_3$ | H | Cl | 129 ± 8% |

[a]Standard error. The data are expressed in percentage of the negative control value (mean of one experiment conducted in triplicate ± Std. Err.).
*Effect at 100 μM.

II.1.2 Neuritogenic Effect of Compounds According to the Invention

To assess the neuritogenic activity of compounds according to the invention, neurite outgrowth per cell was quantified using the Neurite Outgrowth software developed by Xplora Nova. At least 60 neurons per condition were photographed and studied. The results obtained with compound 4bc are shown in FIG. 1.

Figure 1:
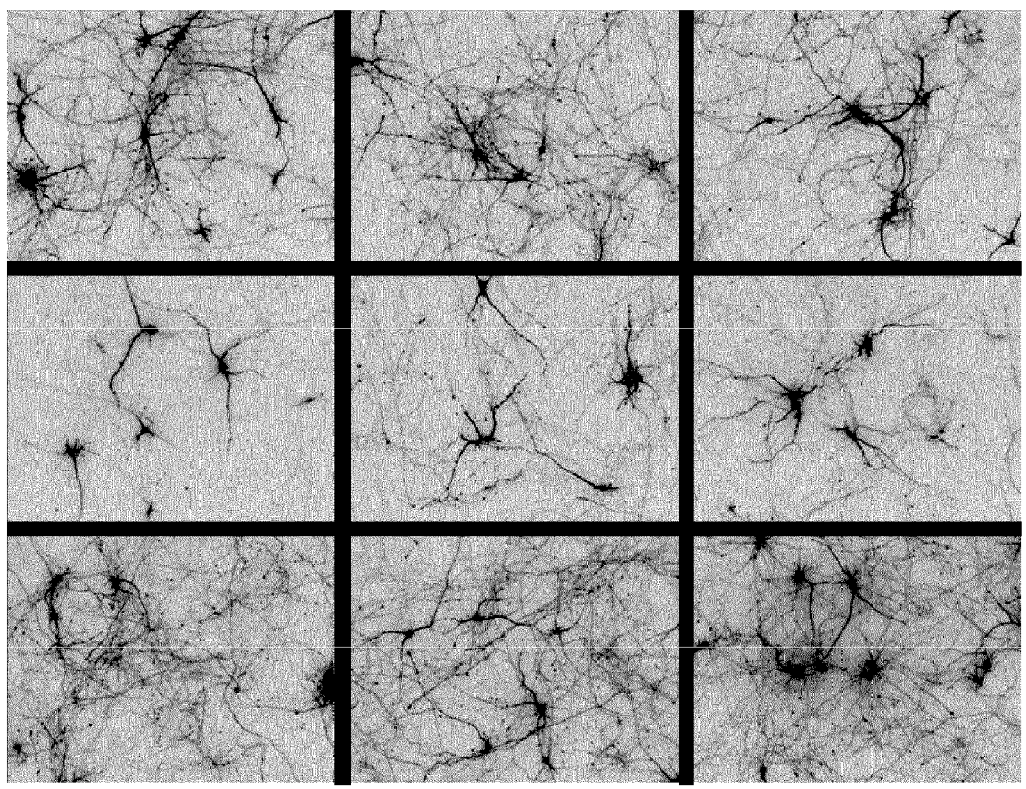
FIG. 1 shows images of untreated cultures (control B), or cultures treated with compound 4bc at 100 nM (A) or with dbcAMP at 200 µM (C), whose dopaminergic neurons are immunolabeled by recognition of tyrosine hydroxylase.

The images shown in FIG. 1 (taken at a magnification of 20× and reversed using image processing software) show either untreated cultures (control B), or culture treated with compound 4bc at 100 nM (A) or with dbcAMP at 200 μM (C), whose dopaminergic neurons are immunolabeled by recognition of tyrosine hydroxylase. A significant increase with regard to the negative control for $TH^+$ neuron differentiation is observed.

This compound 4bc, active on dopaminergic neuron survival, also shows activity on their differentiation, with neurons having longer and more numerous neurite extensions (i.e., axons and dendrites together).

II.2. Study of the Passage of the Blood-Brain Barrier of Compound 4bc
II.2.1. Materials and Methods
Animals:

Male Rj Orl: SWISS, mice, approximately 5 weeks old and weighing between 20 and 24 g at arrival (R Janvier Breeding Center, France) were kept in the animal room at constant temperature (22±1° C.) and controlled humidity (55±20%), with a 12-hour light/dark cycle (8:00 a.m.-8:00 p.m.). During the acclimation and study period, the mice had free access to food and water. All the experiments were conducted in compliance with the conditions of decree 2001-464 of May 29, 2001 relative to animal experimentation.

Treatments:

Two treatment modes were used: intraperitoneal (IP) administration for 1 or 2 days or oral or per os administration for 5 days.

Intraperitoneal Treatment (IP)

The solution of compound 4bc to be injected at a concentration of 7.0 g/L was prepared in a carrier containing 10% Tween 20+20% DMSO+70% 0.9% NaCl in water.

Three animal groups were created:
- mice who received the carrier by IP at 10 mL/kg (Group V, n=2),
- mice treated with compound 4bc by IP at 70 mg/kg and at 10 mL/kg (Group T, n=6),
- one untreated mouse that was used as a positive control during analysis.

Treated mice T2 and T3 received treatments as follows:

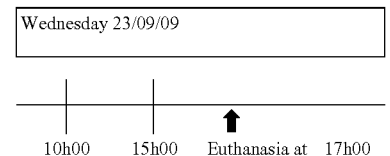

Treated mice T1, T4, T5 and T6 as well as the mice receiving the carrier V1 and V2 received the treatments/carriers as follows:

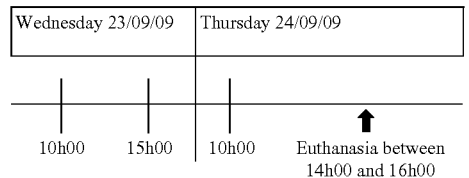

Oral (Per os) Treatment

The solution of compound 4bc at the concentration of 15.0 g/L to be administered was prepared in the following carrier: 0.5% Tween 80+99.5% carboxymethyl cellulose at 1%, in 0.9% NaCl in water.

Three groups were created:
- mice who received the carrier orally at 10 mL/kg (Group V, n=4),
- mice treated with compound 4bc orally at 150 mg/kg and at 10 mL/kg (Group T, n=6),
- control mice who received no treatment (n=2).

All the mice were treated or received the carrier twice daily for 4 days. On the $5^{th}$ day, a last treatment was administered and the animals were euthanized between 4:00 a.m. and 6:40 a.m. after this last treatment according to the following plan:

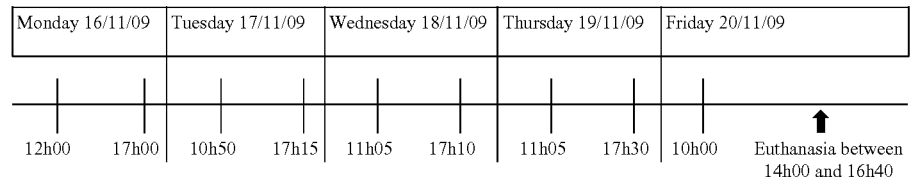

Euthanasia and Dissection:

The mice were anesthetized by an injection of 0.1 mL of a 6% sodium pentobarbital solution and then the mice were infused to eliminate the compound present in the plasma with a 0.9% NaCl solution containing heparin (200 µL of heparin choay to 5000 IU/mL in one liter of 0.9% NaCl). Each animal was infused with a minimum of 50 mL of this solution. The mouse was then decerebrated and the cerebellum, brainstem and olfactory bulbs were removed by dissection.

For the IP study, the brain was dissected into two parts (right and left hemisphere).

Figure 2:
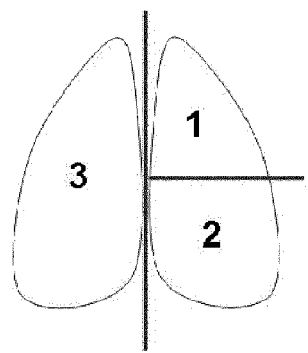
FIG. 2 shows a diagram of the dissection of a mouse brain into 3 parts.

For the per os study, the brain was dissected into 3 parts according to the diagram shown in FIG. 2.

The various parts of the brain were frozen in isopentane at −30° C. for one minute and then stored separately at −80° C.

Extraction Method:

Each mouse brain sample treated with compound 4bc was weighed, placed in MeOH (100 µl MeOH per 10 mg of brain tissue) and then mixed by sonication. The suspensions thus obtained were centrifuged at 14,000 g for 7 minutes at 4° C. for IP or at 27,000 g for 10 minutes, at 4° C. for oral administration. The supernatants, diluted by half in MeOH, were transferred into HPLC vials for analysis of the presence of compound 4bc by HPLC-MS/MS.

Note that in order to store samples for future analyses, only the mouse brain parts 1 treated per os were extracted and analyzes. However, brain parts 1 and 2 of mice T2 and T4 were extracted to verify that compound 4bc is not preferentially distributed into one of these two parts.

All the samples were stored at −4° C. before and during the analyses.

The extracts were analyzed under the same conditions, however the IP and per os extracts were analyzed on different days.

Positive and Negative Controls:

The brain of a mouse that received only the carrier, used in the IP study, was used as the negative control. The brain of a mouse that was not treated, used in the IP study, was used as the positive control.

Each sample was weighed, placed in MeOH (100 µl of MeOH per 10 mg of brain tissue) and 10 or 20 µl of the solution of compound 4bc at 7 g/L were added to the left hemisphere or the right hemisphere of the control mouse. Everything was vortexed and then mixed by sonication. The suspensions thus obtained were centrifuged at 14,000 g for 7 minutes at 4° C. The supernatants, diluted by one fifth in MeOH, were transferred into HPLC vials for analysis of the presence of compound 4bc by HPLC-MS/MS.

Preparation of the Range of Compound 4bc

A stock solution of compound 4bc was prepared extemporaneously in MeOH at a concentration of 1.0 mg/mL. All the other solutions were prepared by dilution of this stock solution in MeOH and then stored at −4° C.

Instrumentation and Conditions for Analysis of Compound 4bc:

Detection and quantification, based on peak area, were done by HPLC-MS/MS in MRM mode.

The HPLC system was composed of a Dionex Ultimate 3000 pump equipped with a Dionex WPS-3000PL automatic sample injector. The mass spectrometer used is a Water-Micromass Quattro Ultima equipped with an electrospray ionization source and a triple quadrupole analyzer. Data was acquired and analyzed by Masslynx 3.5.

Liquid chromatography was performed in isocratic mode with a Nucleodur™ (Macherey-Nagel) C18, 125×2.1 mm column with a particle size of 5.0 µm. The mobile phase was composed of a mixture of two phases A and B, in a proportion of 30/70. Phase A was composed of 1% acetic acid in water (v/v). Phase B was composed of 1% acetic acid in MeOH (v/v). The flow rate was set at 0.2 mL/min; the injection volume was 5 µl.

The mass spectrometer was connected to the HPLC system by using an electrospray ionization source. A switching valve was programmed before injection of the sample for rinsing and equilibration of the capillary, so as to prevent any accumulation of salt in the source capillary. The capillary voltage was set at 4000 V and the cone voltage at 80 V; the source temperature was set at 120° C.; the desolvation gas ($N_2$) was set at a flow rate of 529 and the temperature at 350° C. The mass spectra were obtained in positive mode. The parameters were optimized to obtain the maximum molecular ion ($[M+H]^+$) at m/z 236.41, corresponding to compound 4bc. Collision was done by argon and the energy was set at 30 eV in MS/MS mode for detecting mass transitions: m/z 236.41→117.08; 236.41→131.10 and 236.41→158.27.

The calibration curve was created from a standard range comprising 9 concentrations (100 µg/mL; 10 µg/mL; 1 µg/mL; 0.5 µg/mL; 0.1 µg/mL; 20 µg/mL; 4 µg/mL; 0.8 µg/mL and 0.16 µg/mL).

II.2.2. Results

Toxicity of Compound 4bc:

The animals were weighed every day throughout the sub-chronic study in order to monitor their general condition. Animal weights were considered a good indicator of general health since a compound's toxicity is known to be characterized by loss of bodyweight over time.

Figure 3:
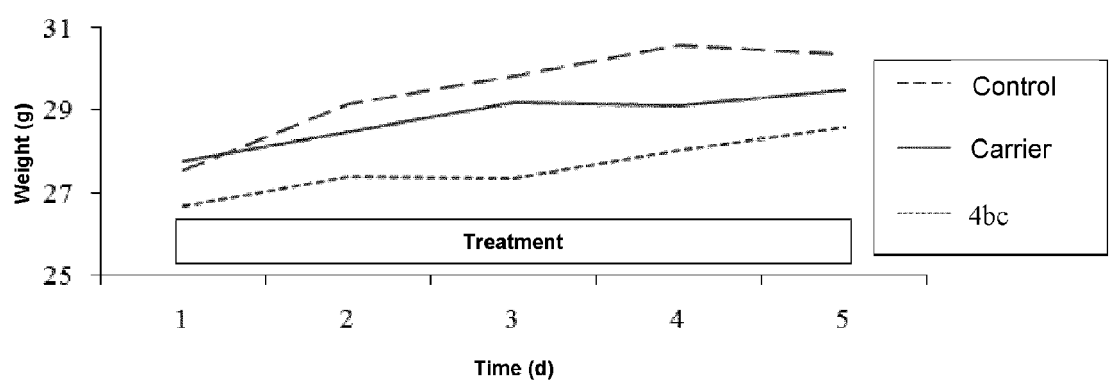
FIG. 3 shows a diagram representing the mean weight (g) of mice of a same group as a function of time (d) during per os treatment for untreated mice, mice who received the carrier or mice who received compound 4bc at 300 mg/kg/day.

FIG. 3 shows the mean of the mice weights of a same group as a function of time during per os treatment (untreated mice, those that received the carrier or those that received compound 4bc in an amount of 300 mg/kg/day).

Per os Study:

The animal weight gain was linear over the experiment, reflecting a good general condition of the animals and an absence of significant toxicity of the compound.

IP Study:

Monitoring mouse weight in the IP study has no value given the short duration of the experiment (1 or 2 days).

Validation of the HPLC MS/MS Method:

IP Route:

The area of the HPLC peaks was a function of the concentration of compound 4bc in the range of 20 ng/mL to 100.00 µg/mL with a correlation coefficient $R^2$ equal to 0.9999. The limit of detection was 4 ng/ml with an S/N (signal-to-noise) ratio of 3:1. The retention time for compound 4bc was 3.3 minutes; the acquisition period was 8 minutes.

Per os Route:

The HPLC peak area was a function of the concentration of compound 4bc in the range of 4 to 1000.00 ng/mL with a correlation coefficient $R^2$ equal to 0.9999. The limit of detection was 0.8 ng/mL with an S/N (signal-to-noise) ratio of 3:1. The retention time for compound 4bc was 3.7 minutes; the acquisition period was 8 minutes.

Concentration of Compound 4bc in Brain and Plasma Extracts.

IP Route:

Compound 4bc was not detectable in the brain extract of the mouse that received the carrier (negative control) and was 0.18 µg/mL and 0.42 µg/mL in the positive controls (control mouse+10 or 20 µL of compound 4bc at 7 mg/mL). Compound 4bc was quantified in the brains of the mice treated by IP and euthanized 2 h after the last treatment at the mean concentration of 8.83 μg/mL±0.92 SEM (n=3).

Figure 4:
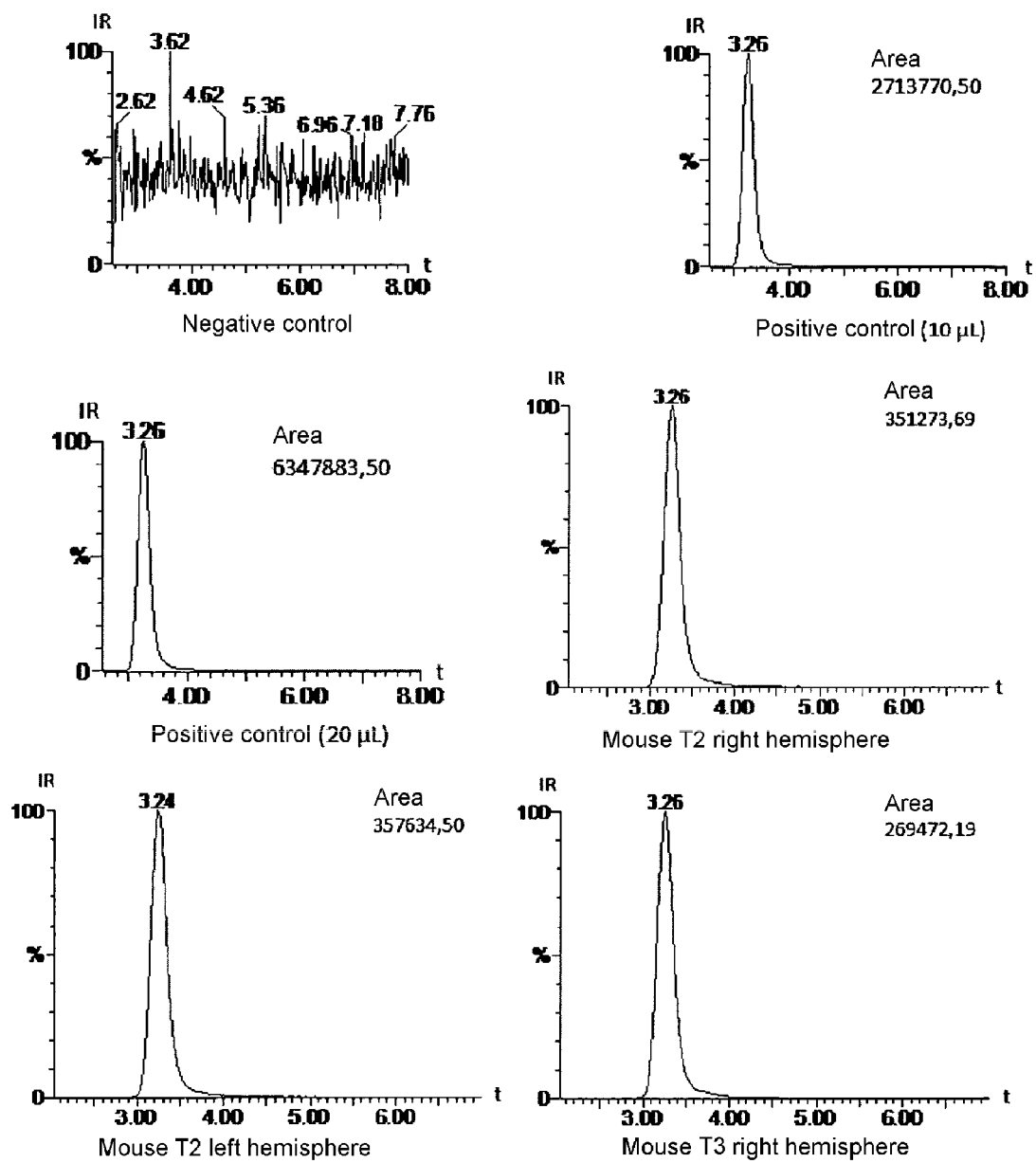
FIG. 4 shows chromatograms (x-axis: time (min); y-axis: relative intensity (%)) obtained by HPLC-MS/MS from brain extracts of different mice of the IP study to quantify compound 4bc.

The chromatograms obtained are shown in in FIG. 4.

Note that the extracts were stored at 4° C. for several days corresponding to the total duration of the analyses. In order to prevent any error related to degradation of the compound, the last sample of a series analyzed during a day was reanalyzed the next day and used as the standard.

IP Route, Final Analysis of the Extracts:

Compound 4bc was quantified in the old brain extracts of the mice treated by IP and euthanized 2 h after the last treatment at the mean concentration of 1.39 μg/mL±0.09 SEM (n=4). These brain extracts were stored for 40 days at 4° C. Compound 4bc was detectable in the old brain extracts of mice treated IP and euthanized between 4 and 6 h after the last treatment (n=8).

Figure 5:
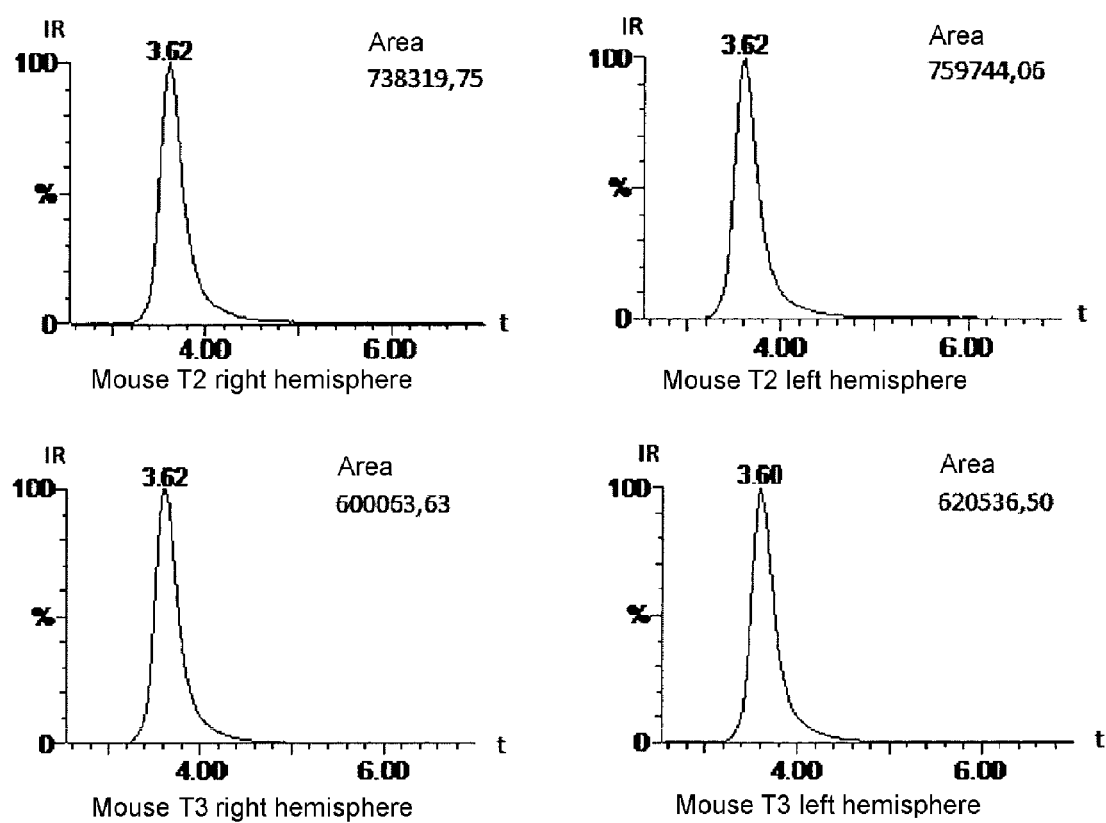
FIG. 5 shows chromatograms x-axis: time (min); y-axis: relative intensity (%)) obtained by HPLC-MS/MS from brain extracts of different mice of the IP study euthanized 2 h after the last treatment, the extracts being kept for 40 days at 4° C. before analysis to quantify compound 4bc.

The chromatograms obtained are shown in FIG. 5 for the brain extracts of mice euthanized 2 h after the last treatment and in FIG. 6 for the brain extracts of mice euthanized between 4 and 6 h after the last treatment; the extracts were stored for 40 days at 4° C. before analysis in both cases.

Per os Route:

Compound 4bc was undetectable in all the brain samples of mice treated per os as shown by the chromatograms obtained in FIG. 7. However, it appears that this result is due to the fact that the mice were euthanized too long after the last treatment. A new study described below therefore had to be conducted so as to examine the influence of time before euthanasia on the concentration of compound 4bc in brain extracts.

Study of the Influence of Time Before Euthanasia on the Concentration of Compound 4bc:

This study was done on C57BL\6J (instead of RjOrl: SWISS) mice treated with compound 4bc by IP or per os.

IP Route

Mice treated by IP route received a treatment of 70 mg/kg to mL/kg of a solution of compound 4bc over 2 days comprising 2 IP injections the first day and 1 IP injection the second day. The results obtained are shown in the following table.

| Time of euthanasia after the last treatment | Brain extract concentration | Plasma concentration |
|---|---|---|
| approximately 1 h | 1 μg/mL | 1.2 μg/mL |
| approximately 1 h 30 min | 0.74 μg/mL | 3.1 μg/mL |
| approximately 1 h 55 min | 0.1 μg/mL | 1.7 μg/mL |
| approximately 2 h 20 min | 0.09 μg/mL | not measured |

The kinetics in mouse brain and plasma of compound 4bc after IP administration are also shown in FIG. 8.

Another study was done in rats treated by IP. These rats received a treatment of 20 or 45 mg/kg at 10 mL/kg of a solution of compound 4bc over 2 days comprising 2 IP injections the first day and 1 IP injection the second day. The results obtained are shown in the following table.

| Treatment | Time of euthanasia after the last treatment | Brain extract concentration | Plasma concentration |
|---|---|---|---|
| 45 mg/kg at 10 mL/kg of compound 4bc | approximately 1 h | 5.1 μg/mL | not measured |
| 20 mg/kg at 10 mL/kg of compound 4bc | approximately 3 h | 0.1 μg/mL | 0.4 μg/mL |

Per os Route

Mice treated per os received a treatment of 150 mg/kg to 10 mL/kg of a solution of compound 4bc over 5 days comprising twice daily administrations for 4 days and a once daily administration the last day. The results obtained are shown in the following table.

| Time of euthanasia after the last treatment | Brain extract concentration | Plasma concentration |
|---|---|---|
| approximately 1 h | 2.2 μg/mL | 11.6 μg/mL |
| approximately 1 h 30 min | 0.2 μg/mL | 0.7 μg/mL |
| approximately 2 h | 0.1 μg/mL | 0.04 μg/mL |
| approximately 2 h 25 min | 0.05 μg/mL | 0.4 μg/mL |

CONCLUSION

Compound 4bc is therefore clearly detectable and quantifiable in all the samples (brain and plasma) whether by IP or per os.

II.2.3. Discussion and Conclusion

Compound 4bc is able to cross the blood brain barrier in vivo after intraperitoneal administration. The brain extracts of animals treated by IP and euthanized between 4 and 6 hours are 2000 times less concentrated in compound 4bc than the extracts of animals treated by IP and euthanized after 2 h post-treatment. The extracts analyzed later, of brains of animals treated by IP and euthanized at 2 h, have a mean value approximately 6 times lower than the one previously calculated (ratio of the means of the concentrations of the same extracts analyzed at the 10 week interval). Since this variation is negligible compared to the ratio of 2000 observed between the extracts of animal brains treated by IP and euthanized at different times, it can be concluded that compound 4bc is eliminated quickly from the brain over time.

Compound 4bc was undetectable in the brains of animals treated by oral administration and euthanized at least 6 hours after the last treatment. However, given the fast clearance of compound 4bc after IP treatment, this result is probably due to too long a waiting time before the last treatment and euthanasia.

A second oral study confirmed this hypothesis. Indeed, when euthanasia was done 1 h after the last administration, the compound was detected in comparable quantities whether administration was IP or per os (1 μg/mL vs. 2.2 μg/mL).

Compound 4bc is able to cross the mouse or rat blood-brain barrier in vivo after oral administration without adverse reactions at a dose of 300 mg/kg/day over a 5-day treatment.

II.3. Study of the Efficacy of Compound 4bc on an Animal Model of Parkinson's Disease The goal of this study is to test by an in vitro study the neuroprotective activity of compound 4bc administered orally to a mouse after it is poisoned by intranasal administration of MPTP. The food intake and weight of the animals were also compared to a control group. The densitometric analysis of striatal fibers and count of dopaminergic cell bodies in the substantia nigra, after immunohistochemical marking of tyrosine hydroxylase enabled quantifying the neuroprotective effect of the compound.

II.3.1. Materials and Methods

Treatment:

30 male C57BL\6J mice aged 3 months (supplier: Janvier Breeding Center) were used during this study.

Compound 4bc was administered orally at a dose of 150 mg/kg to 10 mL/kg, twice daily for two days, and then 75 mg/kg once daily. The carrier was composed of 0.5% Tween 80+99.5% carboxymethylcellulose (at 1% in water). A curved rigid tube connected to a 1 mL Terumo syringe was used for administration.

MPTP, a toxin specific for dopaminergic neurons was administered intranasally. One mg (10 µl) of MPTP/HCl (Sigma) dissolved in a 0.9% NaCl solution was delivered per nostril with a 3-minute interval between the two nostrils. Both nostrils were injected once daily for 4 days.

The study was thus conducted according to the following protocol:
  Co-treatment with MPTP and compound 4bc: day 1 to day 4
  Post-treatment with compound 4bc (once daily for 6 days): day 5 to day 10
  Euthanasia: day 11

Four groups of mice were formed: (T=treated with compound 4bc, NT=not treated, L=lesioned with MPTP, NL=not lesioned with MPTP),
  mice who received the carrier orally at 10 mL/kg (Group NT/NL, n=6),
  mice treated with compound 4bc orally at 150 mg/kg and at 10 mL/kg twice daily for 2 days and then at 75 mg/kg and at 10 mL/kg once daily for 7 days (Group T/NL, n=6),
  mice who received the MPTP by IN administration at 10 mL/kg (Group NT/L, n=9),
  mice treated with MPTP by IN (intranasal) administration and who were treated orally with compound 4bc at 150 mg/kg and at 10 mL/kg twice daily for 2 days and then at 75 mg/kg and at 10 mL/kg once daily for 7 days (Group NT/L, n=9), Immunohistochemistry:

The eleventh day, the animals were anesthetized, infused (0.9% NaCl then 4% paraformaldehyde) and then euthanized. The brains were then extracted and post-fixed for 2 h in a 4% formaldehyde solution then cryoprotected in 30% sucrose for one day. Finally, these brains were frozen and thin slices were made with a freezing microtome.

To quantify the neuroprotective capacity of compound 4bc, an immunohistochemistry study was done on floating brain slices. Two brain anatomic structures were analyzed: the striatum (20 µm slices, 10 levels) and the substantia nigra (20 µm slices, 7 levels).

Tyrosine hydroxylase (TH) was chosen as a biological marker to evaluate the optical density of dopaminergic fibers in the striatum and the number of dopaminergic neurons in the substantia nigra of each animal.

II.3.2. Results

The results obtained are shown in FIGS. 9 and 10.

The following abbreviations were used in these two figures.
  ST.R: right striatum,
  ST.L: left striatum,
  **: significant difference ($p<0.01$),
  *: significant difference ($p<0.05$), and
  NS: not significant ($p>0.05$), The statistical values were obtained by means of a non-parametric test comparing the means of two different groups (Mann-Whitney test). These results show that compound 4bc has a significant neuroprotective activity on dopaminergic fibers in vivo. The mild toxicity observed in animals who received only treatment by compound 4bc was not significant.

The invention claimed is:

1. A method for the treatment of Parkinson's disease comprising the administration to a patient in need thereof of an effective quantity of a compound of formula (I) below:

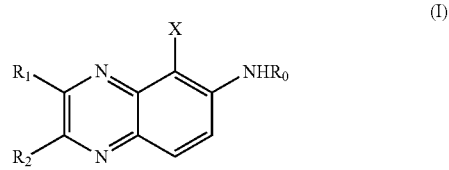

or a pharmaceutically acceptable salt thereof, a stereoisomer thereof or a mixture of stereoisomers thereof in any proportions, wherein:
  X represents a hydrogen atom, a halogen atom, an $NO_2$ group or an $NH_2$ group,
  $R_0$ represents H or —$CH_2$—C≡H, and
  $R_1$ and $R_2$ each represent, independently of one another, a hydrogen atom; a saturated or unsaturated, linear or branched hydrocarbon chain comprising 1 to 10 carbon atoms; or an optionally substituted aryl group.

2. The method according to claim 1, wherein the mixture of stereoisomers is a mixture of enantiomers.

3. The method according to claim 2, wherein the mixture of enantiomers is a racemic mixture.

4. The method according to claim 1, wherein X represents a hydrogen atom, a bromine atom, an $NH_2$ group or an $NO_2$ group.

5. The method according to claim 1, wherein X represents a hydrogen atom.

6. The method according to claim 1, wherein $R_0$ represents H.

7. The method according to claim 1, wherein $R_1$ and $R_2$ each represent, independently of one another, a hydrogen atom; a saturated or unsaturated, linear or branched hydrocarbon chain comprising 1 to 10 carbon atoms; or an aryl group optionally substituted by one or more groups selected from the group consisting of a halogen atom, ($C_1$-$C_6$)alkyl, ($C_1$-$C_6$)alkoxy, aryl, $N_3$, $NO_2$, $NH_2$ and —NH—(($C_1$-$C_6$)alkyl).

8. The method according to claim 1, wherein $R_1$ and $R_2$ each represent, independently of one another, a hydrogen atom; a saturated or unsaturated, linear or branched hydrocarbon chain comprising 1 to 10 carbon atoms; or an aryl group optionally substituted by one or more groups selected from the group consisting of a halogen atom, ($C_1$-$C_6$)alkyl, ($C_1$-$C_6$)alkoxy, aryl, $NH_2$ and —NH—(($C_1$-$C_6$)alkyl).

9. The method according to claim 1, wherein $R_1$ and $R_2$ each represent, independently of one another, a hydrogen atom; a saturated or unsaturated, linear or branched hydrocarbon chain comprising 1 to 10 carbon atoms; or an aryl group optionally substituted by one or more groups selected from the group consisting of a halogen atom, $(C_1$-$C_6)$alkyl, $(C_1$-$C_6)$alkoxy and aryl.

10. The method according to claim 1, wherein $R_1$ and $R_2$ each represent, independently of one another, a hydrogen atom, a $(C_1$-$C_6)$alkyl group, or an optionally substituted aryl group.

11. The method according to claim 1, wherein $R_1$ and $R_2$ each represent, independently of one another, a hydrogen atom, a $(C_1$-$C_6)$alkyl group, or an optionally substituted phenyl group.

12. The method according to claim 1, wherein $R_1$ represents an aryl group optionally substituted by one or more groups selected from the group consisting of a halogen atom, $(C_1$-$C_6)$alkyl, $(C_1$-$C_6)$alkoxy, aryl, $N_3$, $NO_2$, $NH_2$ and —NH—$((C_1$-$C_6)$alkyl).

13. The method according to claim 1, wherein $R_1$ represents a phenyl group optionally substituted by one or more groups selected from the group consisting of a halogen atom, $(C_1$-$C_6)$alkyl, $(C_1$-$C_6)$alkoxy, aryl, $N_3$, $NO_2$, $NH_2$ and —NH—$((C_1$-$C_6)$alkyl).

14. The method according to claim 1, wherein $R_1$ represents a phenyl group optionally substituted by one or more groups selected from the group consisting of a halogen atom, $(C_1$-$C_6)$alkyl, $(C_1$-$C_6)$alkoxy, aryl, $NH_2$ and —NH—$((C_1$-$C_6)$alkyl).

15. The method according to claim 1, wherein $R_1$ represents a phenyl group optionally substituted by one or more groups selected from the group consisting of a halogen atom, $(C_1$-$C_6)$alkyl, $(C_1$-$C_6)$alkoxy and aryl.

16. The method according to claim 1, wherein the compound of formula (I) is selected from the group consisting of the following compounds:

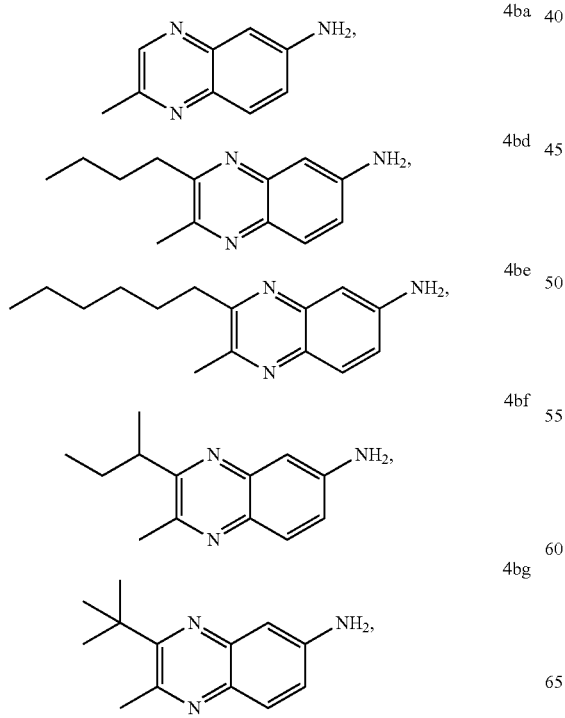

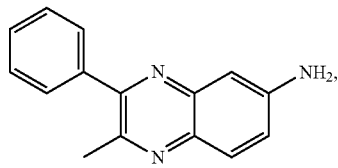
4bc

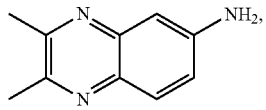
4bb

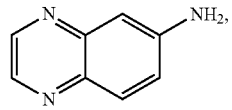
4aa

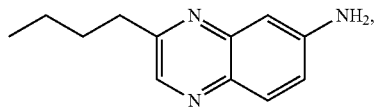
4ad

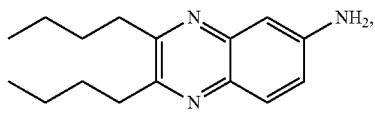
4dd

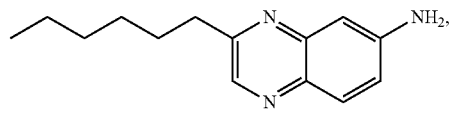
4ae

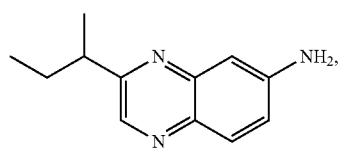
4af

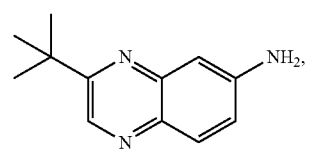
4ag

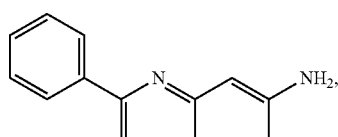
4ac

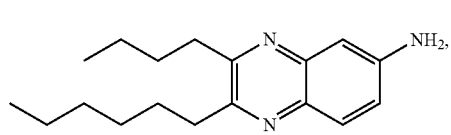
4ed

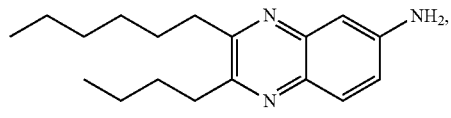
4de

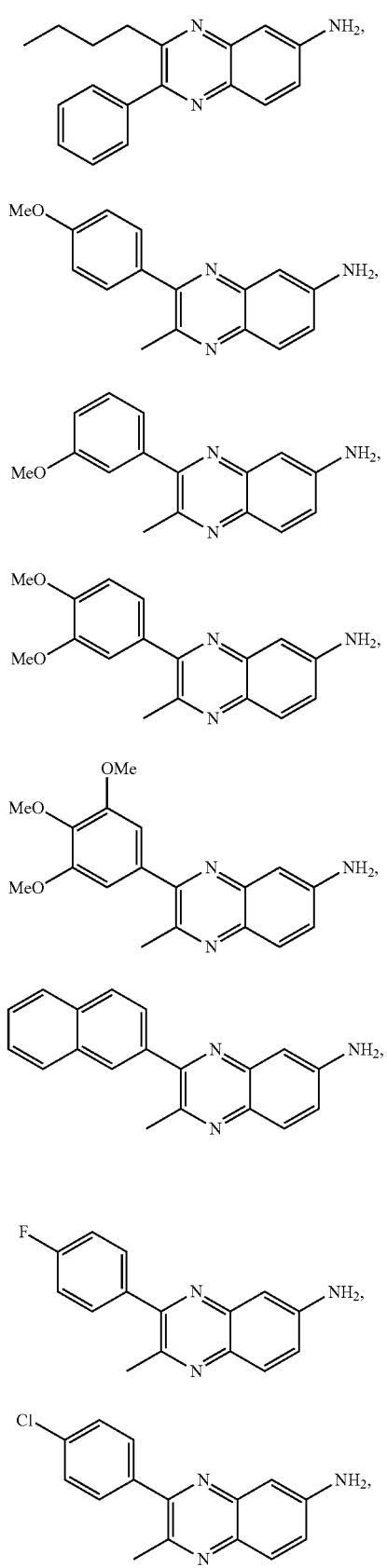
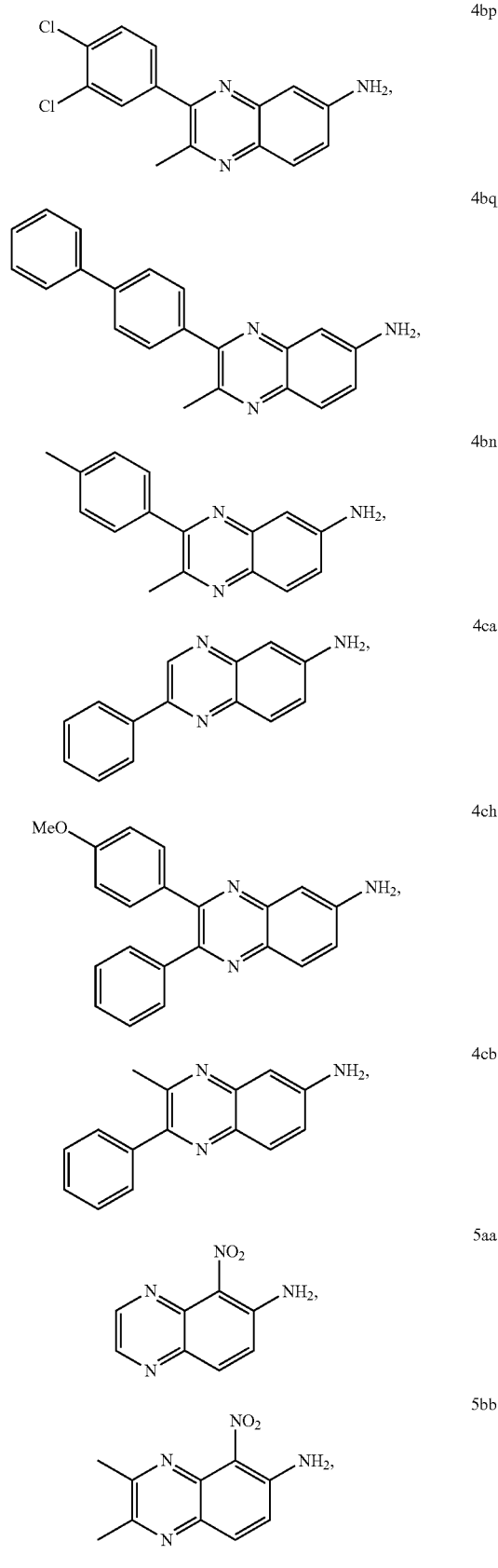

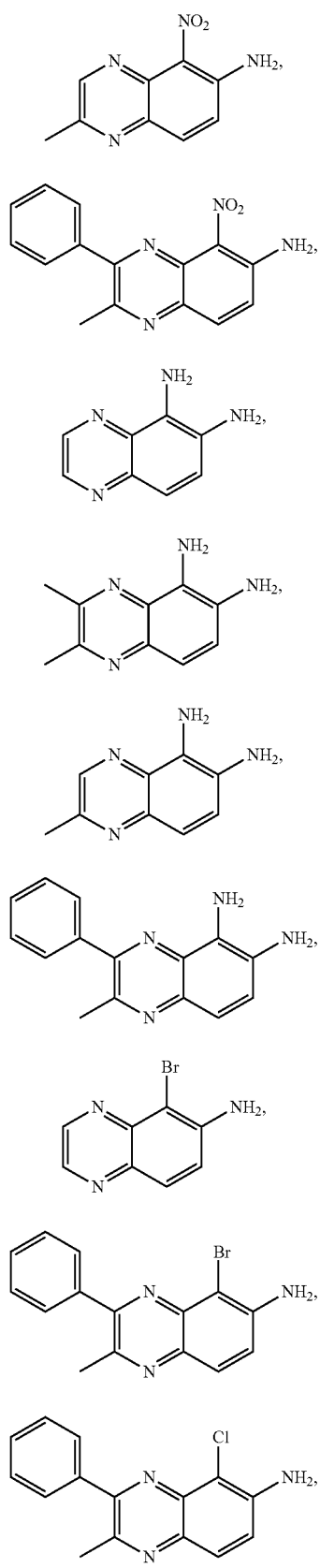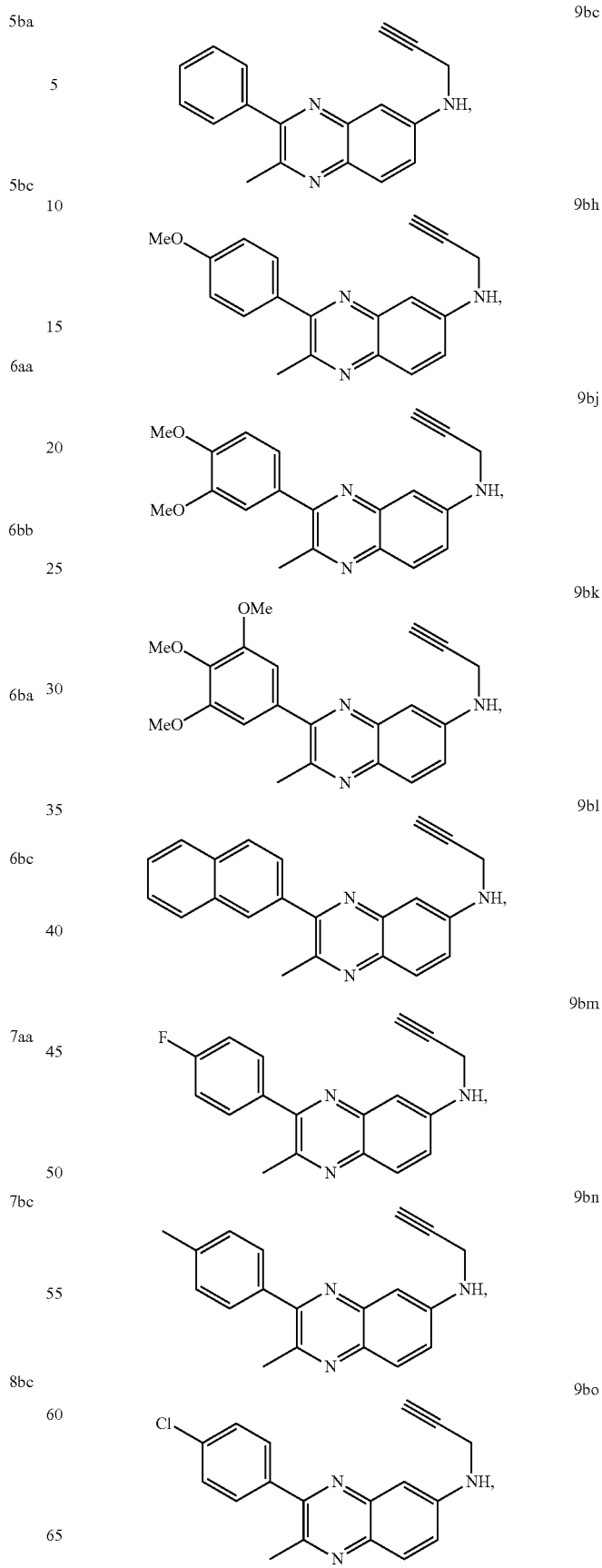

-continued

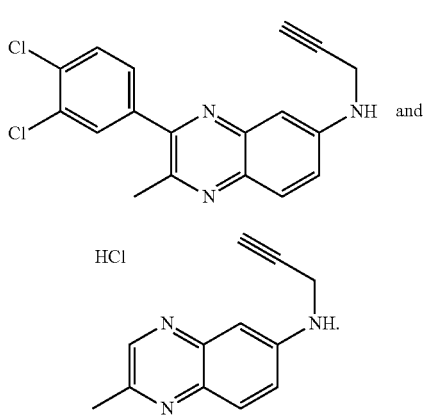

9bp

9ba

17. A method for the treatment of Parkinson's disease comprising the administration to a patient in need thereof of an effective quantity of a compound of formula (I) below:

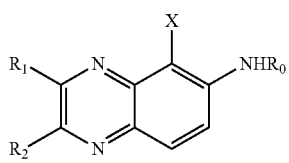
(I)

or a pharmaceutically acceptable salt thereof, a stereoisomer thereof or a mixture of stereoisomers thereof in any proportions,
wherein:
X represents a hydrogen atom, a halogen atom, an $NO_2$ group or an $NH_2$ group,
$R_0$ represents H or —$CH_2$—C≡H, and
$R_1$ and $R_2$ each represent, independently of one another, a hydrogen atom; a $(C_1-C_6)$alkyl group; or an aryl group optionally substituted by one or more groups selected from the group consisting of a halogen atom, $(C_1-C_6)$alkyl, $(C_1-C_6)$alkoxy, aryl, $N_3$, $NO_2$, $NH_2$ and —NH—$((C_1-C_6)$alkyl).

18. The method according to claim 17, wherein $R_1$ and $R_2$ each represent, independently of one another, a hydrogen atom; a $(C_1-C_6)$alkyl group; or an aryl group optionally substituted by one or more groups selected from the group consisting of a halogen atom, $(C_1-C_6)$alkyl, $(C_1-C_6)$alkoxy, aryl, $NH_2$ and —NH—$((C_1-C_6)$alkyl).

19. The method according to claim 17, wherein $R_1$ and $R_2$ each represent, independently of one another, a hydrogen atom; a $(C_1-C_6)$alkyl group; or an aryl group optionally substituted by one or more groups selected from the group consisting of a halogen atom, $(C_1-C_6)$alkyl, $(C_1-C_6)$alkoxy and aryl.

20. A method for the treatment of Parkinson's disease comprising the administration to a patient in need thereof of an effective quantity of a compound of formula (I) below:

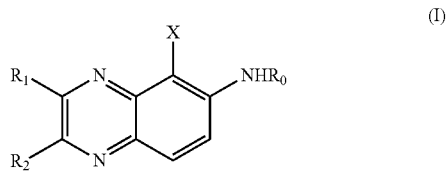
(I)

or a pharmaceutically acceptable salt thereof, a stereoisomer thereof or a mixture of stereoisomers thereof in any proportions,
wherein:
X represents a hydrogen atom, a halogen atom, an $NO_2$ group or an $NH_2$ group,
$R_0$ represents H or —$CH_2$—C≡H, and
$R_1$ and $R_2$ each represent, independently of one another, a hydrogen atom; a $(C_1-C_6)$alkyl group; or a phenyl group optionally substituted by one or more groups selected from the group consisting of a halogen atom, $(C_1-C_6)$alkyl, $(C_1-C_6)$alkoxy, aryl, $N_3$, $NO_2$, $NH_2$ and —NH—$((C_1-C_6)$alkyl).

21. The method according to claim 20, wherein $R_1$ and $R_2$ each represent, independently of one another, a hydrogen atom; a $(C_1-C_6)$alkyl group; or a phenyl optionally substituted by one or more groups selected from the group consisting of a halogen atom, $(C_1-C_6)$alkyl, $(C_1-C_6)$alkoxy, aryl, $NH_2$ and —NH—$((C_1-C_6)$alkyl).

22. The method according to claim 20, wherein $R_1$ and $R_2$ each represent, independently of one another, a hydrogen atom; a $(C_1-C_6)$alkyl group; or a phenyl group optionally substituted by one or more groups selected from the group consisting of a halogen atom, $(C_1-C_6)$alkyl, $(C_1-C_6)$alkoxy and aryl.

* * * * *